US008268302B2

(12) United States Patent
Weiss et al.

(10) Patent No.: US 8,268,302 B2
(45) Date of Patent: Sep. 18, 2012

(54) CULTURES, PRODUCTS AND METHODS USING UMBILICAL CORD MATRIX CELLS

(75) Inventors: Mark L. Weiss, Manhattan, KS (US); Daryl L. Troyer, Manhattan, KS (US); Duane Davis, Westmoreland, KS (US); Kathy E. Mitchell, Columbia, MD (US)

(73) Assignee: Kansas State University Research Foundation, Manhattan, KS (US)

( * ) Notice: Subject to any disclaimer, the term of this patent is extended or adjusted under 35 U.S.C. 154(b) by 46 days.

(21) Appl. No.: 12/773,427

(22) Filed: May 4, 2010

(65) Prior Publication Data

US 2010/0284978 A1 Nov. 11, 2010

Related U.S. Application Data

(63) Continuation of application No. 10/647,361, filed on Aug. 25, 2003, now Pat. No. 7,736,892, which is a continuation-in-part of application No. 10/083,779, filed on Feb. 25, 2002, now abandoned.

(51) Int. Cl.
*A01N 63/00* (2006.01)
*A01N 65/00* (2009.01)
*C12N 5/00* (2006.01)
*C12N 5/02* (2006.01)

(52) U.S. Cl. .................. 424/93.1; 424/93.21; 435/325

(58) Field of Classification Search ............... 424/93.1, 424/93.21; 435/325
See application file for complete search history.

(56) References Cited

U.S. PATENT DOCUMENTS

| 5,639,618 | A | 6/1997 | Gay |
| 5,843,780 | A | 12/1998 | Thomson |
| 5,919,702 | A | 7/1999 | Purchio et al. |
| 5,993,387 | A | 11/1999 | Moore et al. |
| 6,087,113 | A | 7/2000 | Caplan et al. |
| 6,107,543 | A | 8/2000 | Sims et al. |
| 6,127,135 | A | 10/2000 | Hill et al. |
| 6,194,635 | B1 | 2/2001 | Anderson et al. |
| 6,200,806 | B1 | 3/2001 | Thomson |
| 6,235,970 | B1 | 5/2001 | Stice et al. |
| 6,258,998 | B1 | 7/2001 | Damiani et al. |
| 6,271,436 | B1 | 8/2001 | Piedrahita et al. |
| 2003/0161818 | A1 | 8/2003 | Weiss |
| 2005/0054098 | A1 | 3/2005 | Mistry |

FOREIGN PATENT DOCUMENTS

| WO | WO 95/02040 | 1/1995 |
| WO | WO 98/17791 A | 4/1998 |
| WO | WO 98/017791 A | 4/1998 |
| WO | 2007/059084 | 5/2007 |
| WO | 2008/116160 | 9/2008 |

OTHER PUBLICATIONS

Battey et al. Regenerative Medicine. Department of Health and Human Services. Chapter 8, Aug. 2006. </info/scireport/2006report.htm>.*
NIH. Stem Cells: Scientific Progress and Future Research Directions. Chapter 10, pp. 93-98. Department of Health and Human Services. Jun. 2001. </info/scireport/2001report>.*
Zwaka et al. Regenerative Medicine. Department of Health and Human Services. Chapter 4, pp. 45-52, Aug. 2006. </info/scireport/2006report.htm>.*
Wang et al. J. Neuroimmune Pharmacol., 2: 243-250, 2007.*
Lindvall et al. NeuroRX, 1(4): 382-393, 2004.*
Langston. Journal of Clin. Invest., 115(1): 23-25, 2005.*
Dunnett et al. Neuroscience, 2: 365-369, 2001.*
Mendez et al J. of Neuroscience, 16(220: 7216-7227, 1996.*
Went, Philip TH., et al.; "Prevalence of KIT Expression in Human Tumors"; Journal of Clinical Oncology (Nov. 15, 2004); vol. 22, No. 22, pp. 4514-4522.
Hochediinger, Konrad, et al.; "Ectopic Expression of Oct-4 Blocks Progenitor-Cell Differentiation and Causes Dysplasia in Epithelial Tissues"; Cell (May 6, 2005); vol. 121, pp. 465-477.
Gerecht-Nir, Sharon, et al.; "Vascular Gene Expression and Phenotypic Correlation During Differentiation of Human Embryonic Stem Cells"; Developmental Dynamics (2005); vol. 232, pp. 487-497.
Mitchell, Kathy E., et al.; "Wharton's Jelly Mesenchymal Cells form Neurona and Glia"; Mo. Biol. of the Cell, 12 (Suppl.), p. 365A, Abstract 2006, from the 41st Annual Meeting of the American Society for Cell Biology, Dec. 8-12, 2001, publicly available Nov. 2001.
Thomson, James AL., et al.; "Embryonic Stem Cell Lines Derived from Human Blastocysts"; Science (Nov. 6, 1998); vol. 282, pp. 1145-1147.
Hoffman, Lisa A., et al.; "Characterization and culture of human embryonic stem cells;" Nature Biotechnology (Jun. 2005); vol. 23, No. 6, pp. 699-708.
Kaufman, Dan S., et al.; "Hematopoietic colony-forming cells derived from human embryonic stem cells"; PNAS (Sep. 11, 2001); vol. 98, No. 19, pp. 10716-10721.
Robertson, "Teratocarcinomas and embryonic stems cells a practical approach" Embryo-derived stem cells, pp. 72-112. Weiss et al, "Human umbilical cord matrix stem cells: preliminary characterization and effect of transplantation in a rodent model of Parkinson's disease" Stem Cells, 2006, 24:781-792.
Romanowicz et al, Activities of Some Glycosaminoglycan-Degrading Enzymes in Wharton's Jelly and Their Alternation in EPH-Gestosis (Pre-Eclampsia) Biology of the Neonate, 1999; 76: pp. 144-152.
Doetschman et al, The in vitro development of blastocyst-derived embryonic stem cell lines: formation of visceral yolk sac, blood islands and myocardium, Journal of Embryology and Experimental Morphology, vol. 87 (1985) pp. 27-45.
Lanza et al, "Extension of Cell Life-Span and Telomere Length in Animals Clones from Senescent Somatic Cells" Science, vol. 288, Apr. 28, 2000, pp. 665-669.
"Stem Cells: A Primer" National Institutes of Health, May 2000 (6 PGS).

(Continued)

*Primary Examiner* — Thaian N Ton
(74) *Attorney, Agent, or Firm* — Casimir Jones SC

(57) ABSTRACT

Stem cells from human sources can have a variety of useful applications in disease treatment and biotechnology. More particularly the umbilical cord matrix cell cultures of the invention have a variety of totipotent, pluripotent, or multipotent cells for a variety of end uses from a non-controversial, universally available, species-specific source. The technology can have application to any amniotic animal, including agricultural and laboratory animals and humans. The invention relates to isolating the stem cells, culturing the stem cells, maintaining the stem cells, transforming the stem cells into useful cell types using genetic or other transformation technologies, stem cell and tissue banking and using untransformed or transformed cells in disease treatment.

2 Claims, 30 Drawing Sheets

OTHER PUBLICATIONS

Robertson, "Teratocarcinomas and embryonic stems cells a practical approach" Embryo-derived stem cells, pp. 72-112, 1987.

Issaragrisil et al, "Brief Report: Transplantation of Cord-Blood Stem Cells into a Patient with Severe Thalassemia" The New England Journal of Medicine, Feb. 9, 1995) pp. 367-369.

Evans et al, "Establishment in culture of pluripotential cells from mouse embryos" Nature, vol. 292 (Jul. 9, 1981) pp. 154-156.

Weiss et al, "Transplantation of porcine umbilical cord matrix cells into the rat brain," Exp Neur (2003) 182: 288-99.

Romanov et al, "Searching for Alternative Sources of Postnatal Human Mesenchymal Stem Cells: Candidate MSC-Like Cells from Umbilical Cord," Stem Cells (2003) 21(1): 105-10.

Mitchell et al, "Matrix Cells from Wharton's Jelly Form Neurons and Glia." Stem Cells, (2003) 21: 50-60.

* cited by examiner

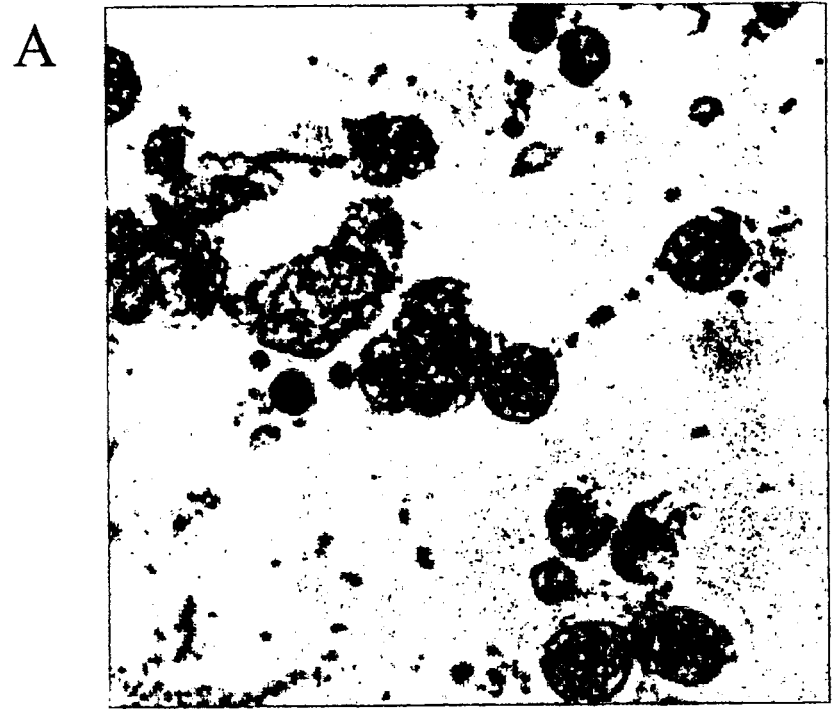
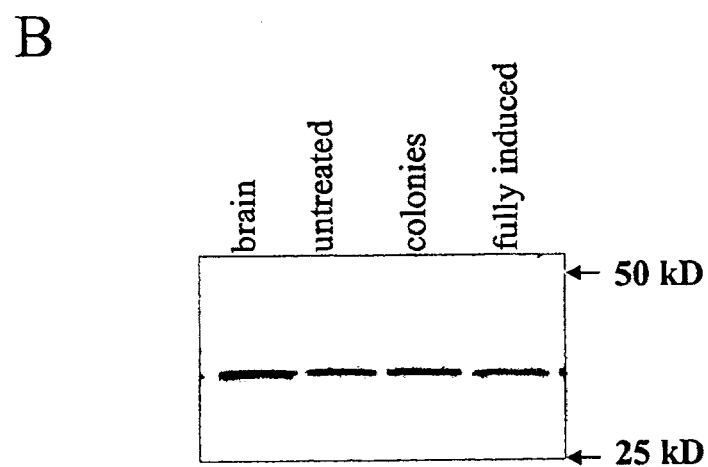
FIG. 6 A-B

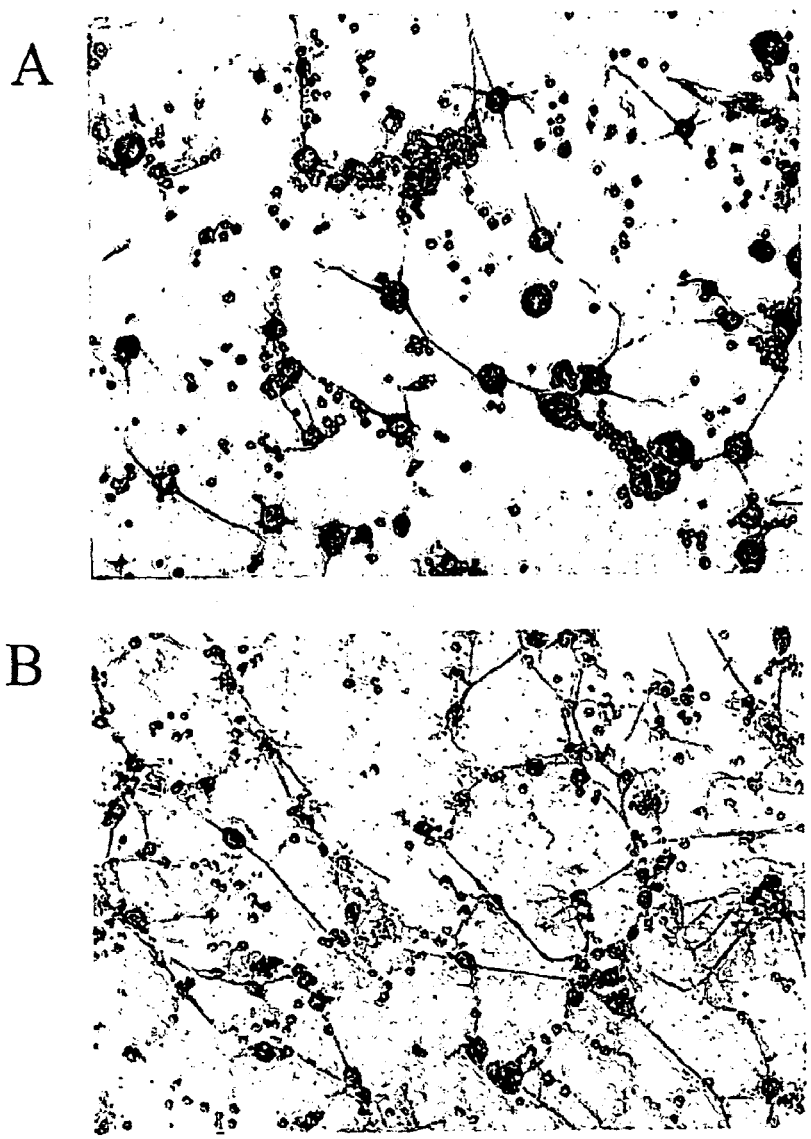
FIG. 7 A-B

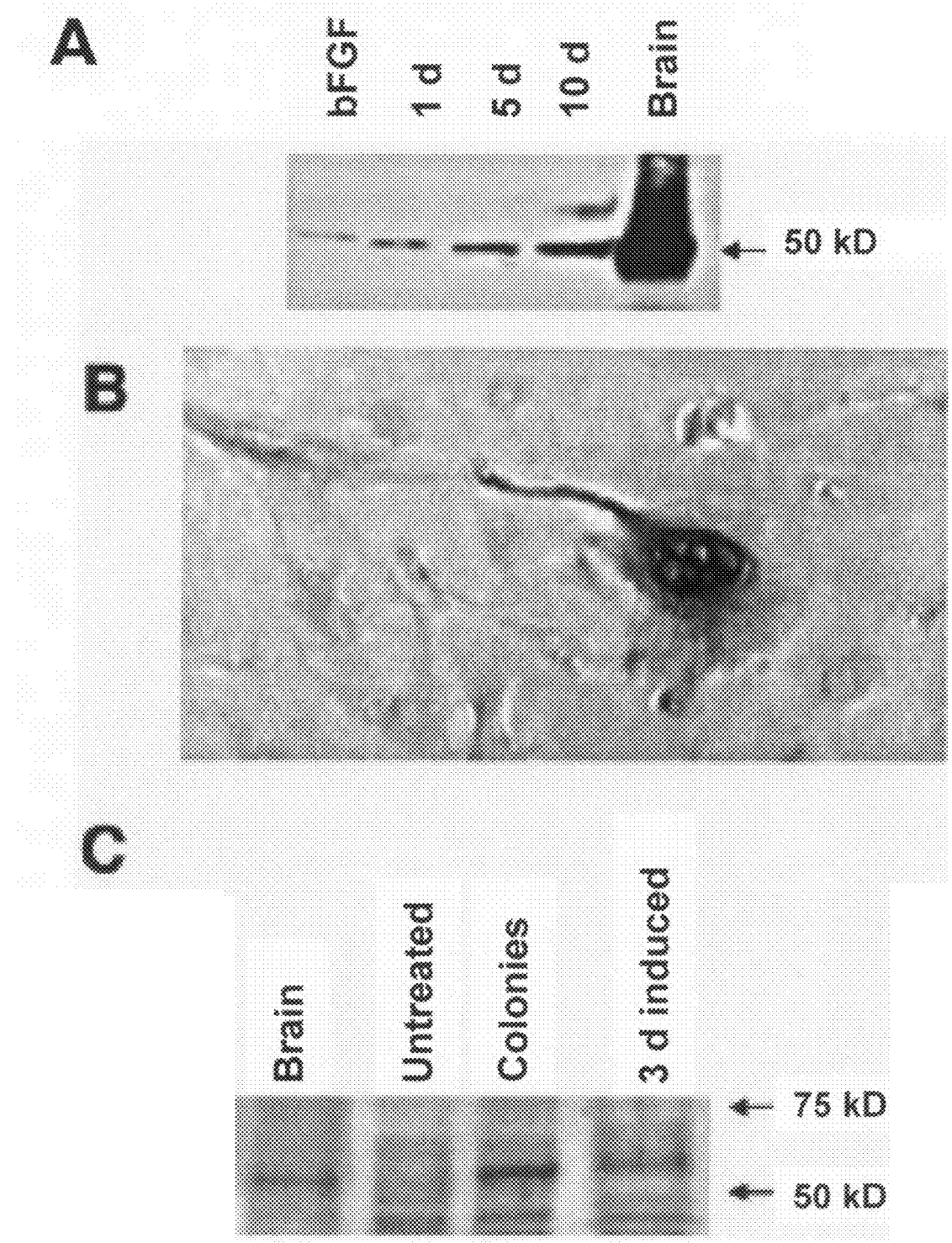
FIG. 8 A-C

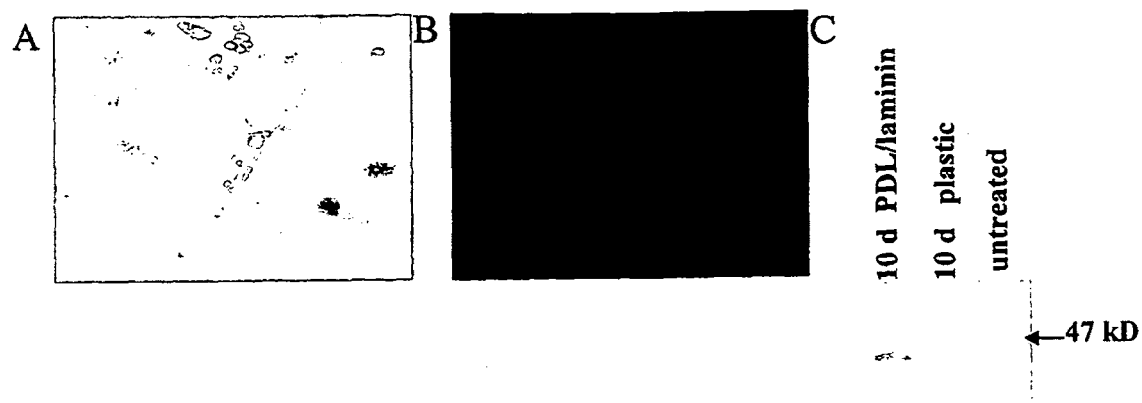
FIG. 9 A-C

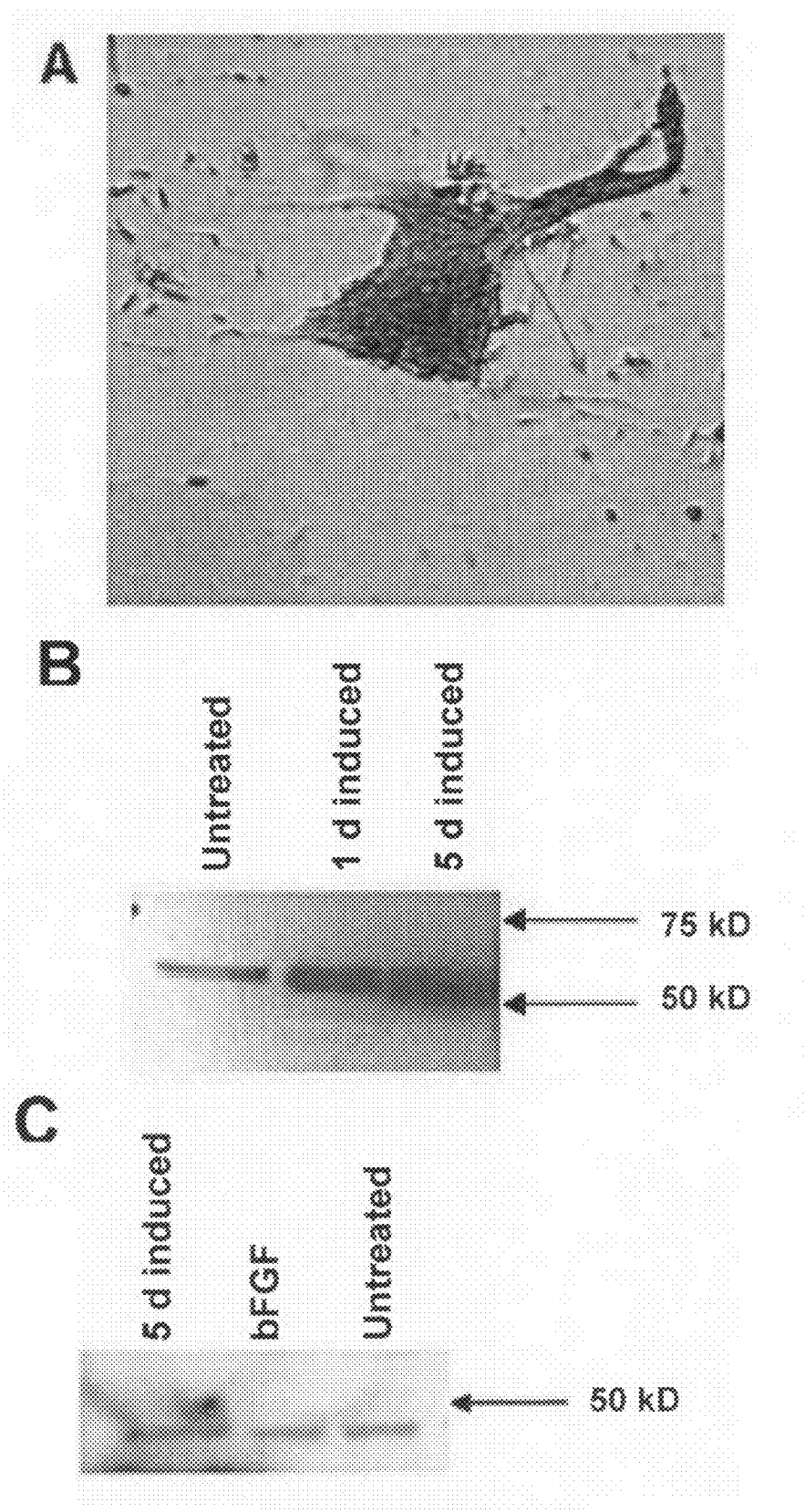
FIG. 10 A-C

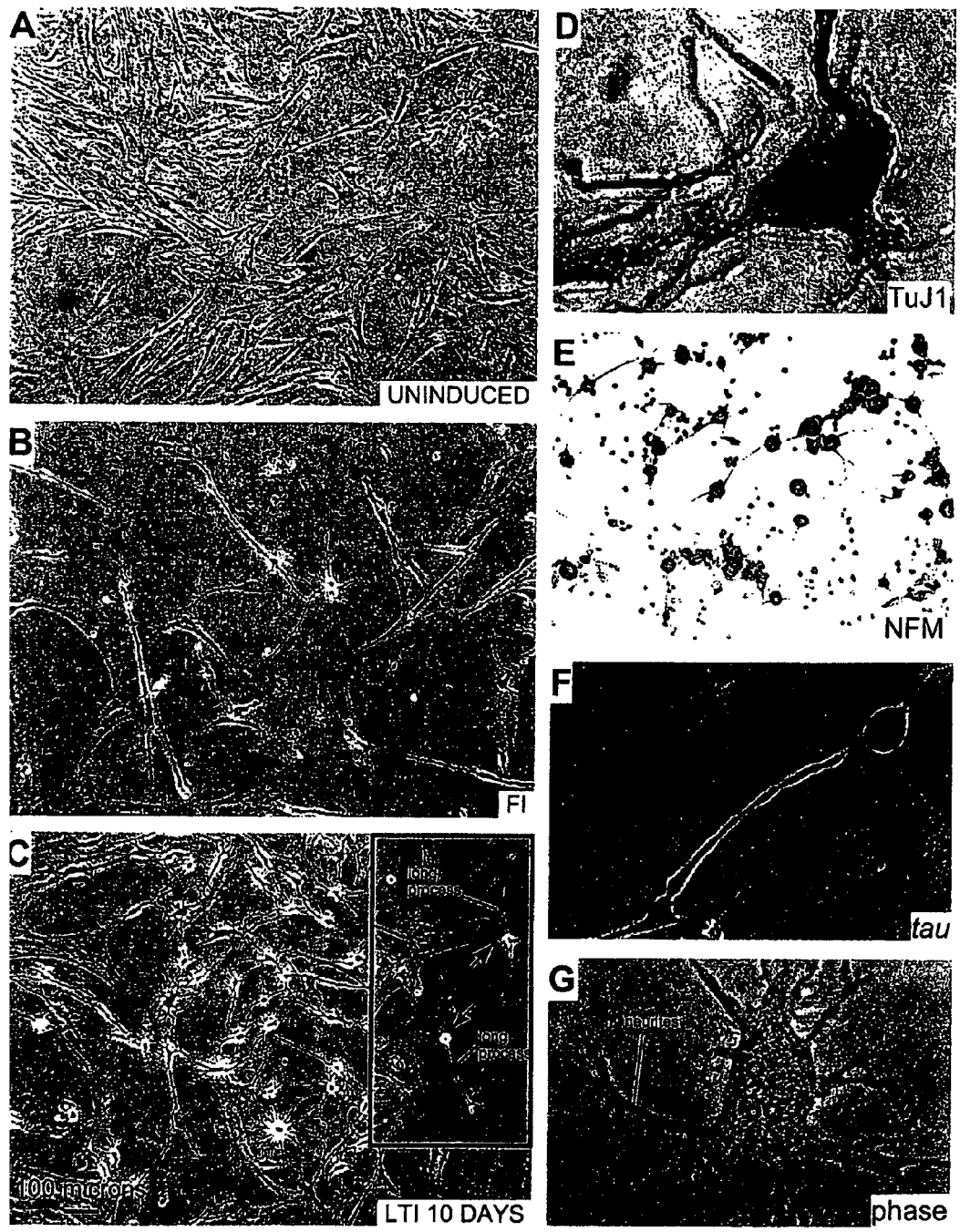
FIG. 18 A-G

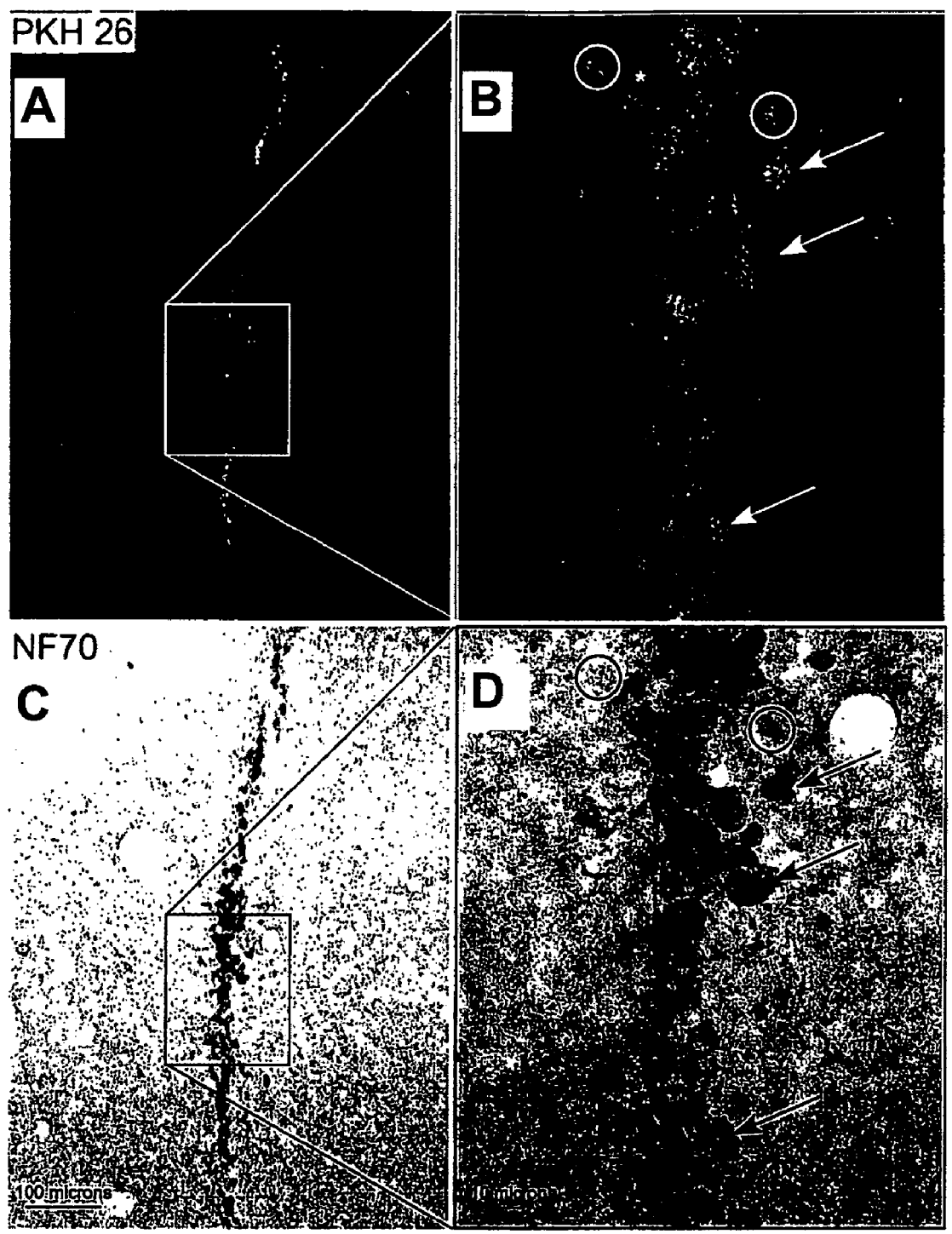
FIG. 19 A-D

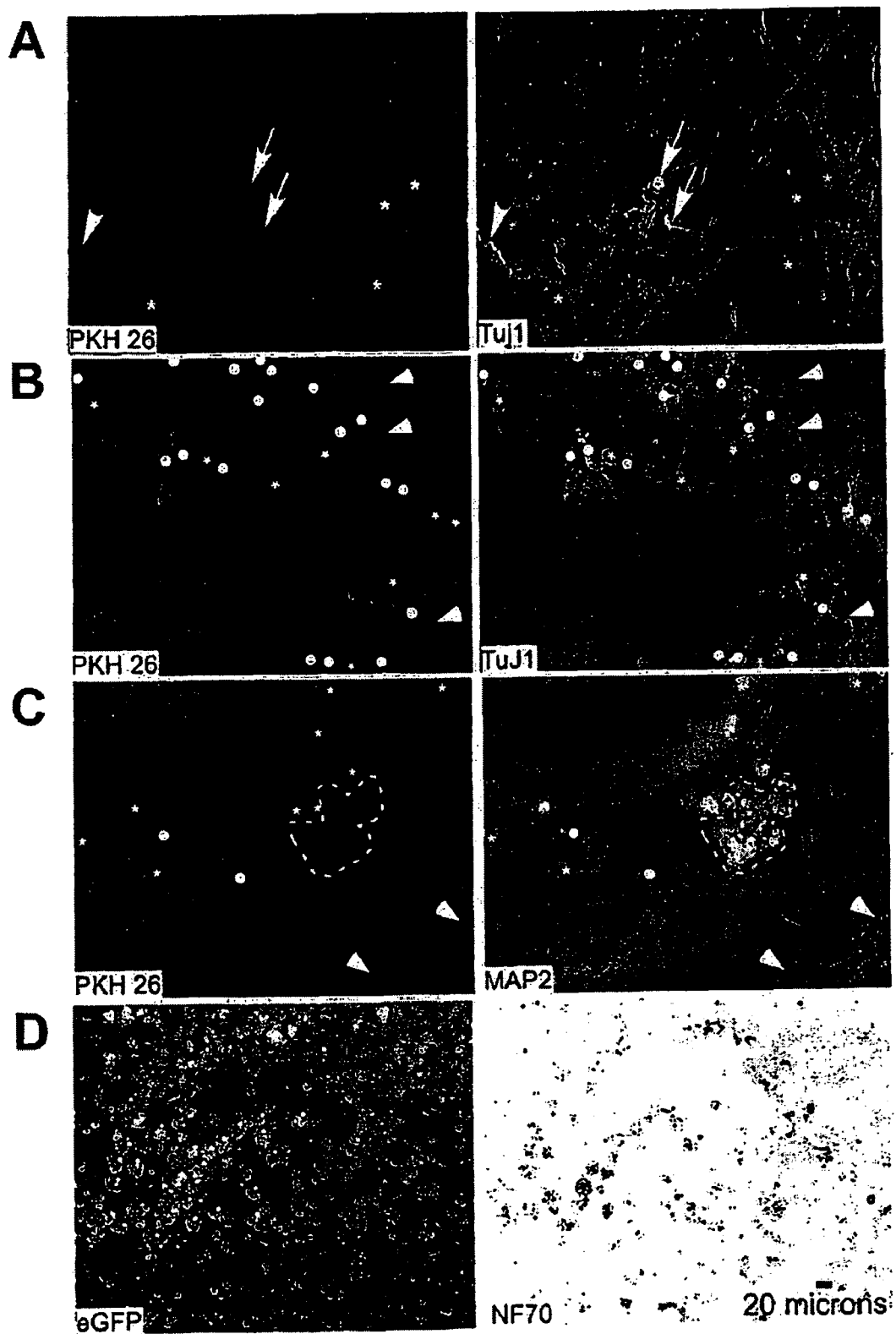
FIG. 20 A-D

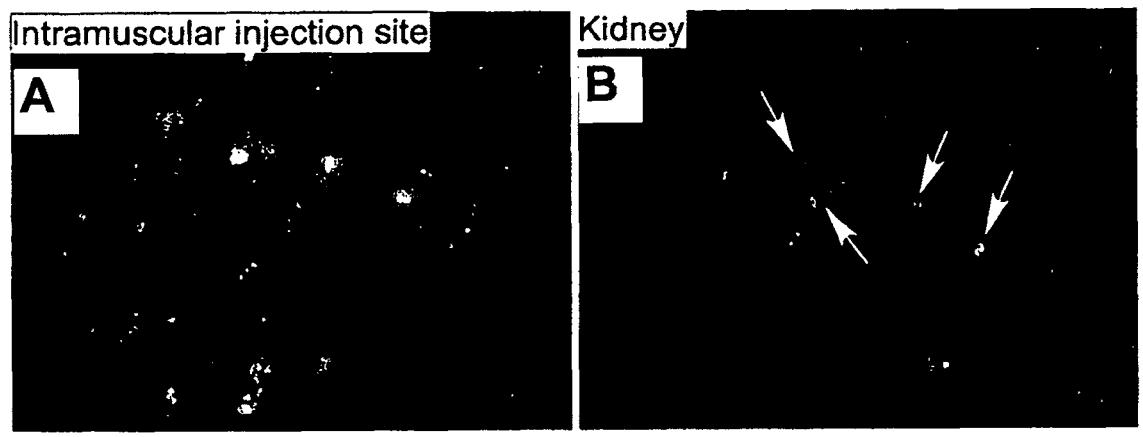
FIG. 21 A-B

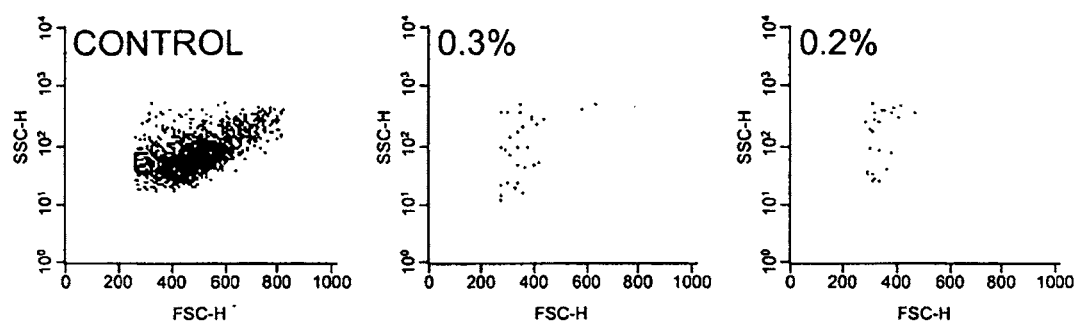
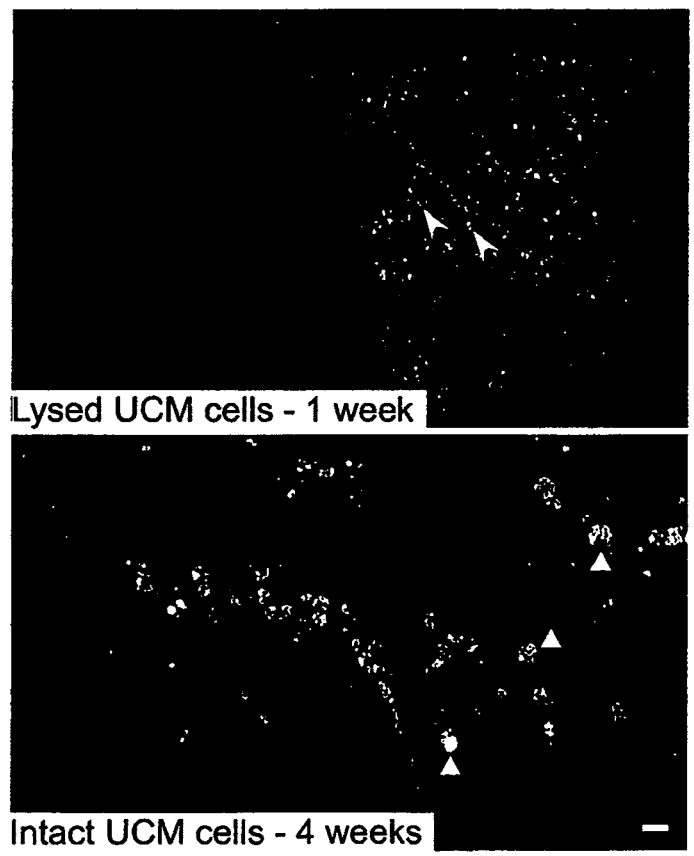
FIG. 22 A-B

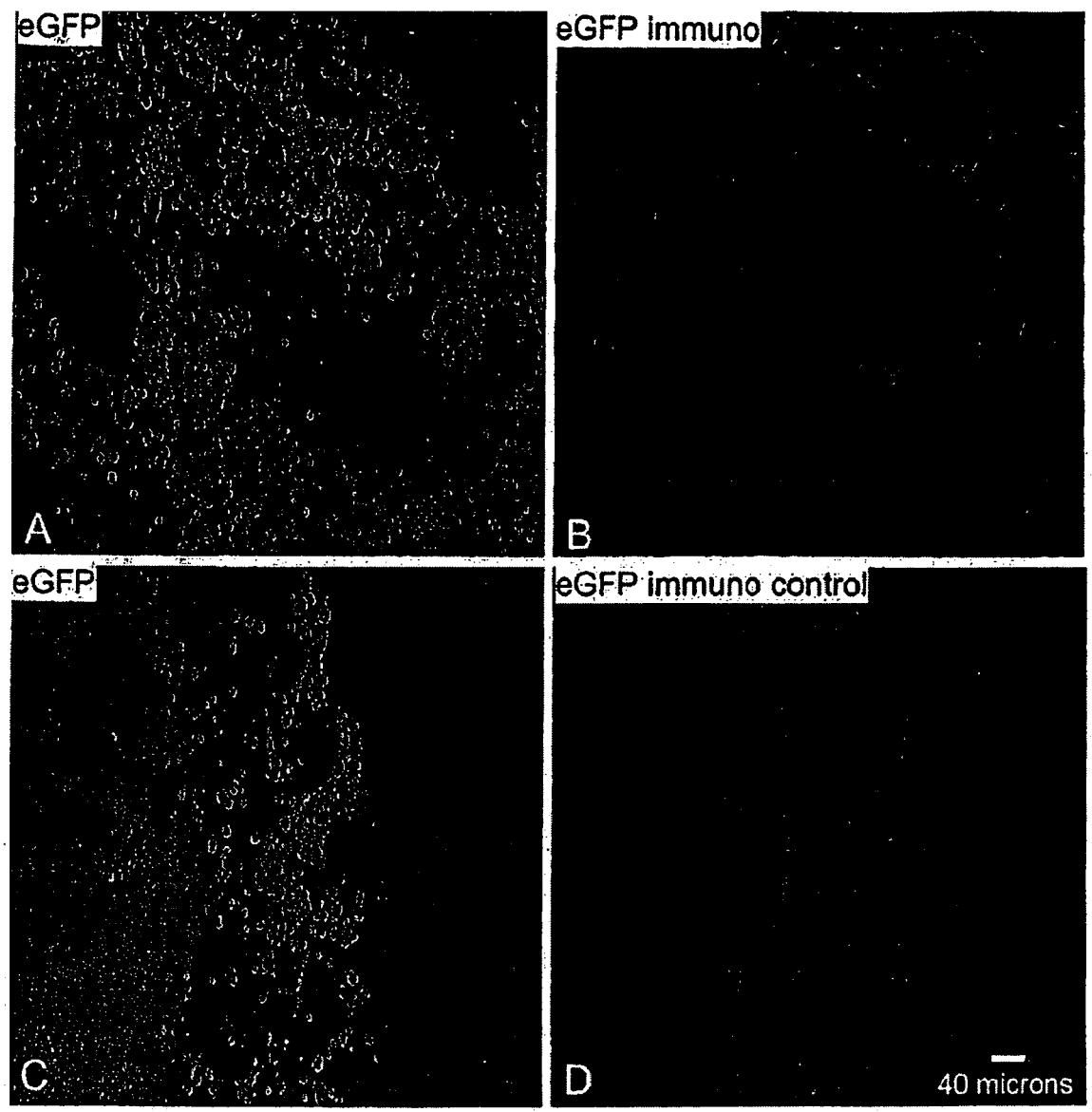
FIG. 23 A-D

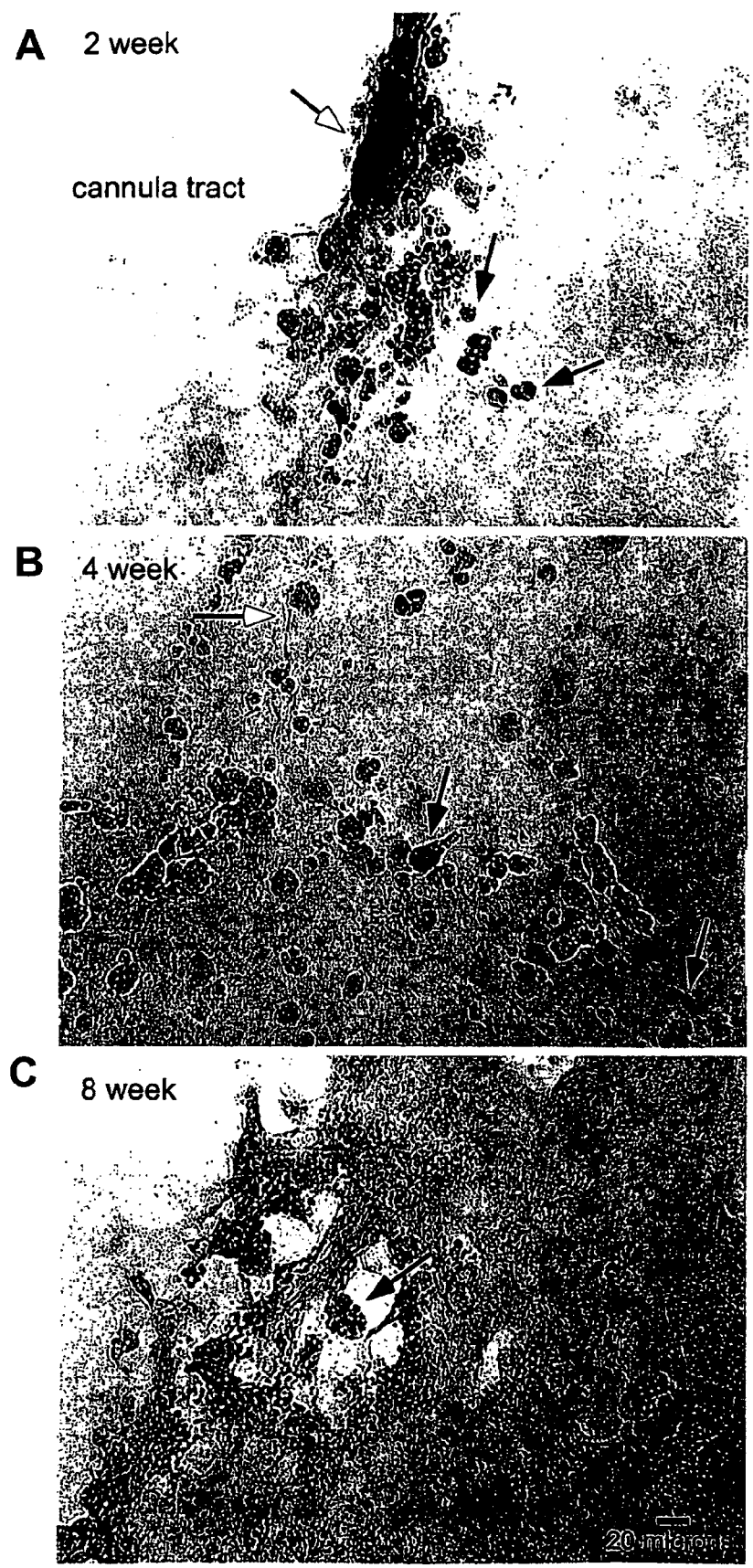
FIG. 24 A-C

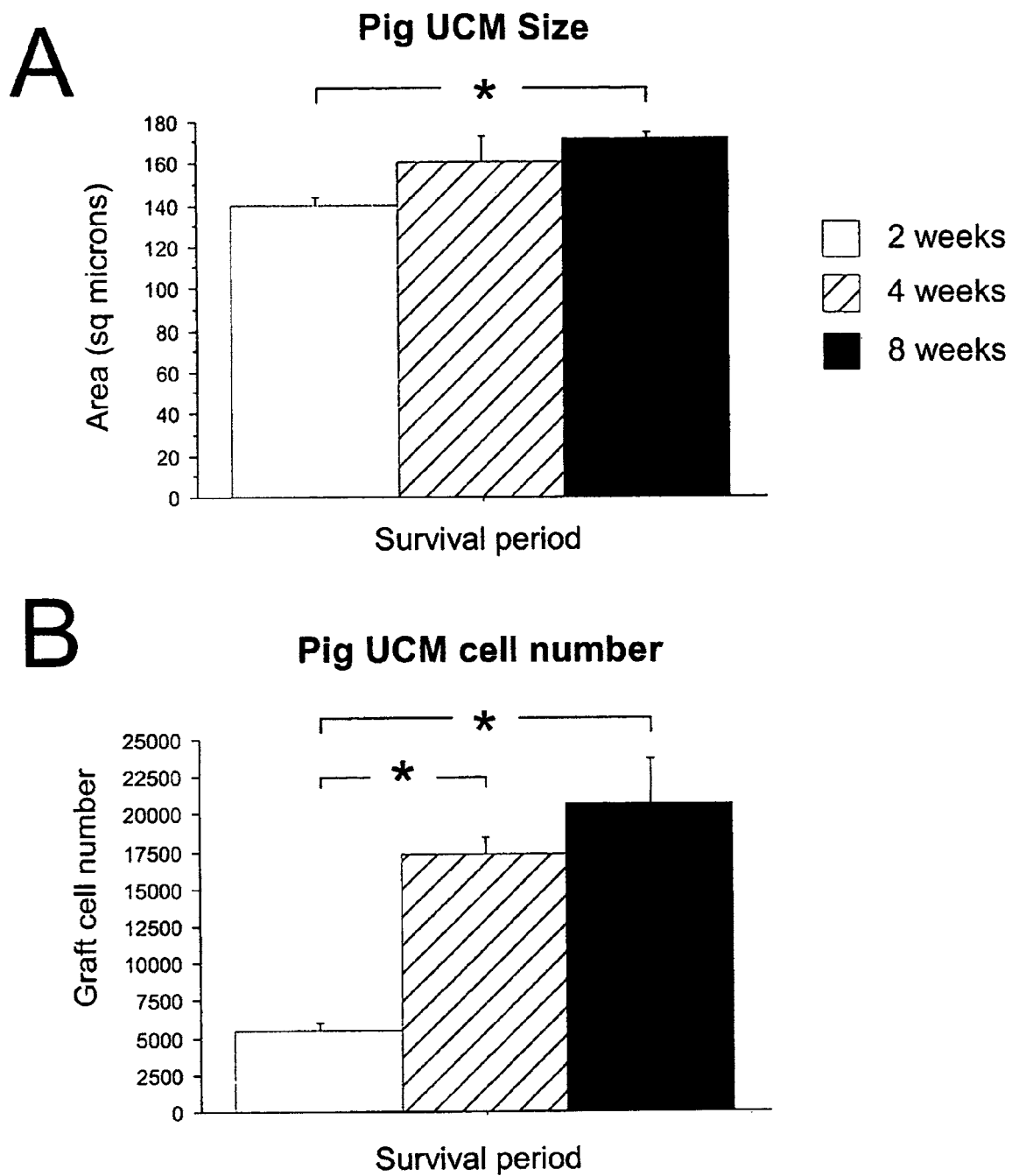
FIG. 27 A-B

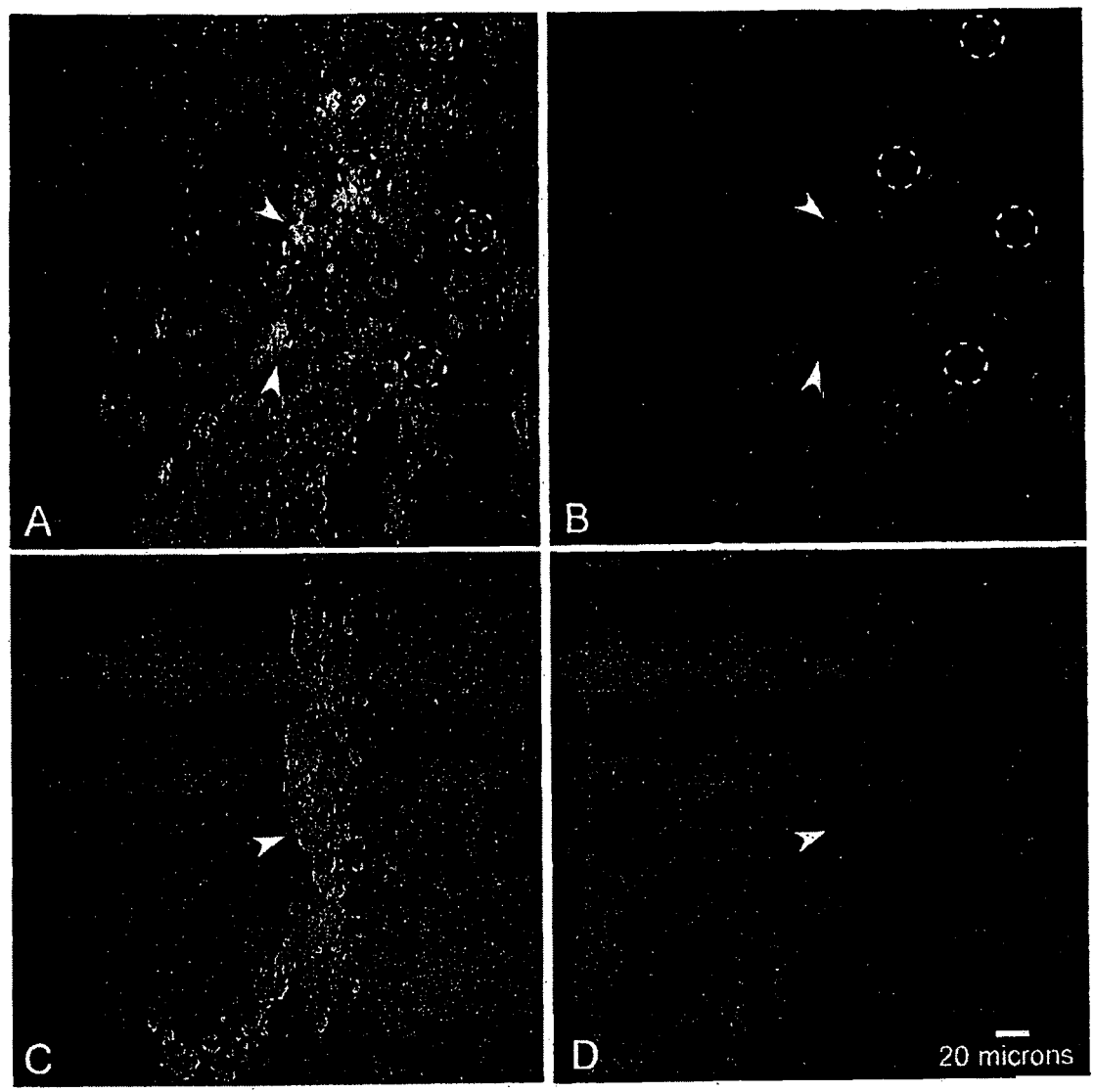
FIG. 28 A-D

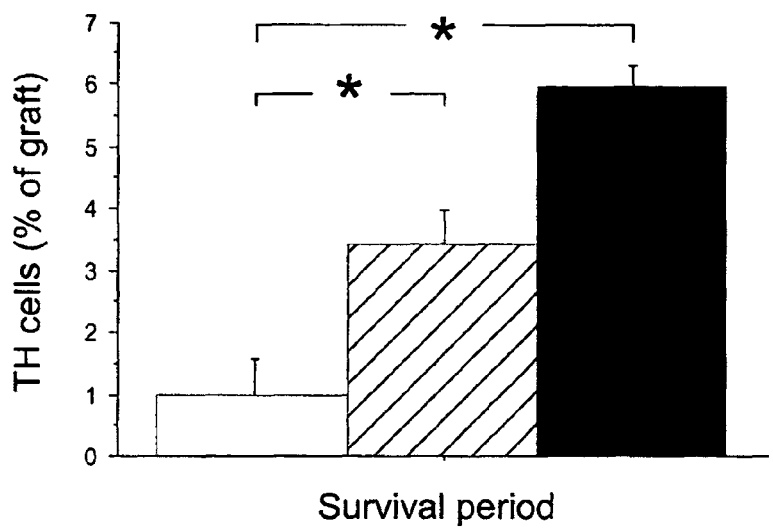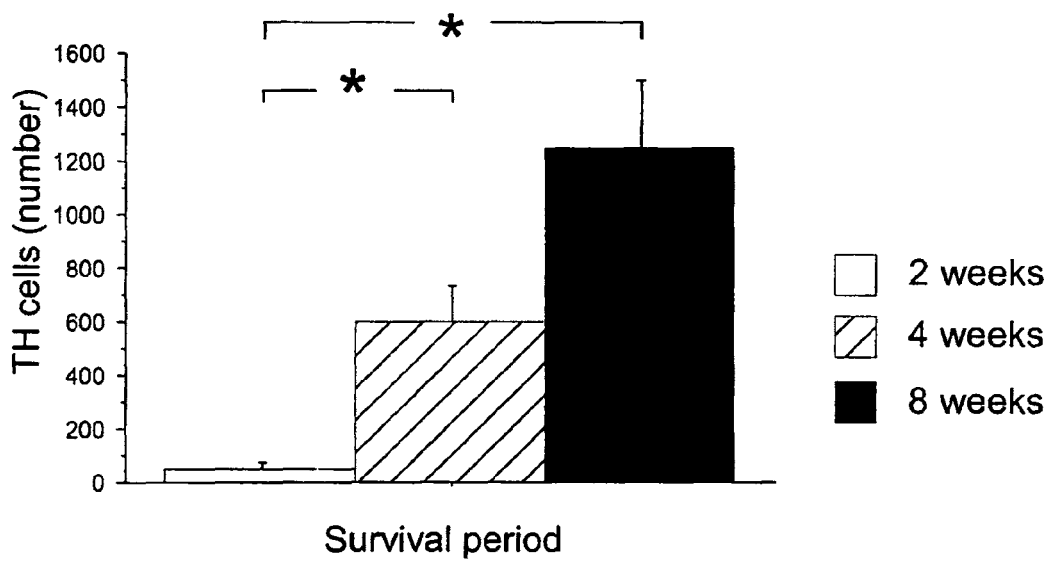
FIG. 29 A-B

CULTURES, PRODUCTS AND METHODS USING UMBILICAL CORD MATRIX CELLS

CROSS REFERENCE TO RELATED APPLICATION

This application is a continuation of application Ser. No. 10/647,361, filed: Aug. 25, 2003, now U.S. Pat. No. 7,736,892 which is a continuation-in-part of U.S. patent application Ser. No. 10/083,779, filed: Feb. 25, 2002, now abandoned, each of which are herein incorporated by reference in their entirety.

This invention was made with U.S. Government support under grant number 5RO1NS034160 awarded by the National Institutes of Health. The Government has certain rights to the invention.

FIELD OF THE INVENTION

The invention relates to the isolation and use of stem cells from amniote species (potentially any animal with an umbilical cord, including humans). More particularly the invention relates to obtaining stem cells that are at least multipotent and may be totipotent or nearly totipotent and are envisaged to have a variety of end uses. The cells are derived from a readily available source that is not controversial in humans or other animal applications. The invention also may be useful for providing a species-specific feeder cell layer or conditioned media for propagating embryonic stem cells. Invention relates to isolating the stem cells, culturing the stem cells, transforming the stem cells into useful cell types using genetic or other transformation technologies, and using untransformed or transformed cells in placental mammalian, human or animal disease treatment and related biotechnology.

BACKGROUND OF THE INVENTION

Stem Cells

Following fertilization of an egg by a sperm, a single cell is created that has the potential to form an entire differentiated multi-cellular organism including every differentiated cell type and tissue found in the body. This initial fertilized cell, with total potential is characterized as totipotent. Such totipotent cells have the capacity to differentiate into extra-embryonic membranes and tissues, embryonic tissues and organs. After several cycles (5 to 7 in most species) of cell division, these totipotent cells begin to specialize forming a hollow sphere of cells, the blastocyst. The inner cell mass of the blastocyst is composed of stem cells described as pluripotent because they can give rise to many types of cells that will constitute most of the tissues of an organism (not including some placental tissues etc.). Multipotent stem cells are more specialized giving rise to a succession of mature functional cells. The multipotent stem cell can give rise to hematopoietic, mesenchymal or neuroectodermal cell lines.

Totipotent Cells

Pluripotent Stem Cell

Multipotent Stem Cell

Committed Cell Lineages

Characteristics of Useful Pluripotent Stem Cells

True pluripotent stem cells should: (i) be capable of indefinite proliferation in vitro in an undifferentiated state; (ii) maintain a normal karyotype through prolonged culture; and (iii) maintain the potential to differentiate to derivatives of all three embryonic germ layers (endoderm, mesoderm, and ectoderm) even after prolonged culture. Strong evidence of these required properties have been published only for rodent embryonic stem cells (ES cells) and embryonic germ cells (EG cells) including mouse (Evans & Kaufman, Nature 292: 154-156, 1981; Martin, Proc Natl Acad Sci USA 78: 7634-7638, 1981) hamster (Doetschman et al. Dev Biol 127: 224-227, 1988), and rat (Iannaccone et al. Dev Biol 163: 288-292, 1994), and less conclusively for rabbit ES cells (Giles et al. Mol Reprod Dev 36: 130-138, 1993; Graves & Moreadith, Mol Reprod Dev 36: 424-433, 1993). However, only established stem cell lines from the rat (Iannaccone, et al., 1994, supra) and the mouse (Bradley, et al., Nature 309: 255-256, 1984) have been reported to participate in normal development in chimeras.

Stem Cells—Methods of Isolation

(a) Non-Human

U.S. Pat. No. 5,843,780 discloses a purified preparation of non-human primate embryonic stem cells comprising the steps of isolating a primate blastocyst, isolating cells from the inner cellular mass (ICM) of the blastocyst, plating the ICM cells on a fibroblast layer (wherein ICM-derived cell masses are formed) removing an ICM-derived cell mass and dissociating the mass into dissociated cells, replating the dissociated cells on embryonic feeder cells and selecting colonies with compact morphology containing cells with a high nucleus/cytoplasm ratio, and prominent nucleoli. The cells of the selected colonies are then cultured.

U.S. Pat. No. 6,107,543 is directed to a method for isolating cultured totipotent stem cells from domestic animals and to a process for the culture of isolated, totipotent stem cells from domestic animals that allows retrieval of large populations of stem cells and maintenance of both pluripotent cells and totipotent cells in culture. The embryonic stem cells are derived from the inner cell mass or earlier stages (i.e., morula) of the developing embryo which can be maintained in a way such that they can multiply but do not differentiate. When the cells are exposed to differentiating conditions, they are totipotent and can develop into all the tissues of the body. The "inner cell mass" is defined as a thicker accumulation of cells at one pole of the blastocyst. The cell culture system can be used for isolating and culturing totipotent stem cells of domestic animals. These cells can be used in genetic manipulation techniques.

U.S. Pat. No. 6,107,543 is directed to a method for transferring a nucleus from a cultured totipotent embryonic stem cell derived from an in vivo or in vitro produced embryo to a recipient oocyte and culturing the resulting nuclear transferred embryo in vitro or in vivo comprising collecting embryos from donor animals, isolating the inner cell mass from the embryos, dissociating the stem cells of the inner cell mass to form donor nuclear transfer stem cells, culturing the dissociated donor nuclear transfer stem cells, collecting and culturing recipient oocyte from donor animals or their products, enucleating the oocyte, transferring a single stem cell to the enucleated oocyte to form a nuclear transferred oocyte, and forming a viable single cell embryo from the nuclear transferred oocyte.

U.S. Pat. No. 5,639,618 provides a method of isolating a lineage specific stem cell in vitro, comprising: (a) transfecting a pluripotent embryonic stem cell with a construct comprising a regulatory region of a lineage specific gene operably linked to a DNA encoding a reporter protein; (b) culturing the pluripotent embryonic stem cell under conditions such that the pluripotent embryonic stem cell differentiates into a lineage specific stem cell; and (c) separating the cells which express the reporter protein from the other cells in the culture, the cell which expresses the reporter protein being an isolated lineage specific stem cell. A lineage specific stem cell can also be identified utilizing this method.

(b) Human

Stem cells can be isolated from any known source of stem cells, including, but not limited to, bone marrow, both adult and fetal, mobilized peripheral blood (MPB) and umbilical cord blood. The use of umbilical cord blood is discussed, for instance, in Issaragrishi et al. (1995) N. Engl. J. Med. 332: 367-369. Initially, bone marrow cells can be obtained from a source of bone marrow, including but not limited to, ileum (e.g. from the hip bone via the iliac crest), tibia, femora, spine, or other bone cavities. Other sources of stem cells include, but are not limited to, embryonic yolk sac, fetal liver, and fetal spleen. Other mature tissue sources have been proposed as sources of stem cells, however these tissues are as yet not demonstrated to be workable.

Human pluripotent cells have been developed from two sources with methods previously developed in work with animal models. Pluripotent stem cells have been isolated directly from the inner cell mass of human embryos (ES cells) at the blastocyst stage obtained from In Vitro Fertilization programs. Pluripotent stem cells (EG cells) have also been isolated from terminated pregnancies.

The proposal that stem cells be obtained from an embryo source (commonly fertilized egg cells from fertility clinics) remains ethically controversial. The controversy surrounding obtaining stem cells from newly fertilized human material has increased a need for obtaining useful stem cells from a non-controversial source. Accordingly a substantial need for obtaining stem cells having a powerful universal and versatile treatment capability is present.

Multipotent stem cells have been found in adult tissue. For example, blood stem cells, found in the bone marrow and blood stream of adults, continually replenish red blood cells, white blood cells and platelets. However as a source for therapeutically useful or pluripotent stem cells adults remain problematic. Stem cells have not been isolated from all body tissues. Even when present in a tissue, adult stem cells are often present in only minute numbers and are difficult to isolate and purify. There is evidence that such adult stem cells may not have the same capacity to adapt or proliferate or differentiate as younger cells obtained from blastocyst, fetal or neonatal sources. Research on the early stages of cell specialization may not be possible with more mature and specialized adult stem cells.

Pluripotent Stem Cells—Applications i. Research

Pluripotent stem cells have a number of possible applications. Pluripotent stem cells could provide insight into the complex events of human development particularly the cellular decision-making process that results in cell specialization. This might suggest treatments for disorders of abnormal cell specialization such as cancer and birth defects. Generating pluripotent stem cells would be useful for generating transgenic non-human primates for models of specific human genetic diseases or for other purposes. Stem cells will allow the generation of models for any human genetic disease for which the responsible gene has been cloned. The human genome project will identify an increasing number of genes related to human disease, but will not always provide insights into gene function. Transgenic models will be essential for elucidating mechanisms of disease and for testing new therapies.

ii. Drug Testing

Drug testing may benefit from a source of human pluripotent stem cells as new medications could be tested on human cell lines before animal and human research.

iii. Cell Therapies

Many diseases are the result of disruption of cellular function or destruction of body tissues. Stem cells could be used in "cell therapies" to replace destroyed, non-functioning or abnormally functioning tissue. For example, recent studies have demonstrated that neural stem cells from the Central Nervous System (CNS) show tropism for specific diseased areas of the brain when grafted into animals. Neural stem cells from the CNS are rare, difficult to obtain and are not a feasible source of cells for applications in human medicine. In the mid-1990's, it was shown that embryonic stem cells from mice could be induced to form neurons and glia in vitro. If pluripotent stem cells can be stimulated to develop into specialized cells, they could be used to treat a range of Central Nervous System disorders such as Parkinson's and Alzheimer's disease, spinal cord injury, stroke, ALS, Hematopoietic Disorders such as sickle cell disease, leukemia, Cardiac Disorders, inborn metabolic and storage diseases and other diseases, for example, diabetes.

By manipulating culture conditions, stem cells can be induced to differentiate to specific cell types such as blood cells, neural cells or muscle cells to mention a few examples.

iv. Tissue Growth and Transplantation

Transplantation of exogenous progenitor cells may provide a means to repopulate diseased tissues and organs. One source of exogenous progenitor cells has been Bone Marrow Stromal (BMS) cells. BMS cells are pluripotent cells that can differentiate into bone, cartilage, fat, muscle, tendon, neurons and many other tissues. BMS cells transplanted into rats with induced liver damage contribute to the formation of new hepatic oval cells that can further differentiate into hepatocytes and ductal epithelium. Bone marrow derived cells also 'home' in to damaged muscle in irradiated mice.

BMS cells injected intracerebroventricular migrate extensively and differentiate into glial cells and neurons in neonatal mice. Spinal cord neural stem cells injected into the Central Nervous System (CNS) differentiate into neurons or glia depending upon the injection site. Like the 'homing' potential of BMS cells to damage e.g. liver or muscle, neural stem cells and embryonic neuroblasts have tropism for glioma or degenerating neurons in adult brains. Neuroblasts injected into cortical lesions differentiate into projection neurons containing the appropriate neurotransmitter and receptor phenotype.

While the technique of 'Tissue transplantation' has been utilized extensively in order to replace damaged organs or tissues, problems with the procedure continue to limit its use.

Finding donors is a problem. Harvesting the tissue (or cells) involves an invasive procedure. The supply of tissue is limited and patients often have to wait for long intervals before an organ is available. Some organs cannot be transplanted. The recipient must be immune-suppressed to a degree that can have undesirable side effects and furthermore makes the patient susceptible to infections. The use of fetal tissues has raised ethical concerns. Sophisticated banking or storing materials for transplant is necessary. Post-mitotic cells are not amenable to genetic manipulation.

In many applications, a strong need for culture technology capable of growing and maintaining stable or useful cultures of stem cells has been a highly desired end. Many current stem cell cultures are based on murine cell culture "feeder cell" technology. Non-species specific feeder cell technology reduces the value of stem cell cultures due to the foreign nature of the source of the feeder cell. This is true for number of reasons including the fact that such non-species specific feeder cells contain both foreign cells and foreign growth factors. Further, we believe that the use of non-species specific feeder cells in combination with different but desirable cultured cells cannot provide the optimum growth conditions as species specific derived feeder cells. This issue is particularly relevant to agricultural animals, endangered species, laboratory animals and non-human primate cells. Still further, non-human feeder cell technology reduces the value of human derived stem cell cultures. This is true for number of reasons including the fact that such non-human feeder cells contain both non-human cells and non-human growth factors. Further, we believe that the use of non-human feeder cells in combination with human cultured cells cannot provide the optimum growth conditions as human derived feeder cells.

A new feeder cell technology is needed to ensure that stem cells are not contaminated with cells, organelles, metabolic products, peptides, antibodies, etc. from another species and are grown or maintained with optimal growth conditions.

A method is necessary that would make stem cells, both pluripotent and multipotent, easy to procure particularly in a manner that provides powerful, universal and versatile treatment capability using a commonly available non-controversial stem cell source.

There have been attempts to solve these problems. Some organs may be harvested from cadavers. Bone marrow may be collected from the living, a procedure that is painful and invasive. There has to be donor-recipient tissue matching (allograft). Attempts have been made to use animal tissue. For example, Parkinson patients have received tissue grafts harvested from fetal pig brain. Such a xenograft is antigenic and the immune response may kill the graft.

SUMMARY OF THE INVENTION

Overview

Stem cells are capable of self-regeneration and can become lineage committed progenitors which are dedicated to differentiation and expansion into a specific lineage. As used herein, "stem cells" refers to progenitors to hematopoietic and non-hematopoietic cell types and virtually all cell types in the body.

The invention relates to isolated and purified stem cells derived from Umbilical Cord Matrix Stem (UCMS) cells, also known as Wharton's Jelly Cells. Such cells can be found in nearly any animal with an umbilical cord, including amniotes, placental animals, humans, and the like. Such matrix cells typically include extravascular cells, mucous-connective tissue (e.g., Wharton's Jelly) but typically do not include cord blood cells or related cells. The invention addresses the use of cells that can include stem cells and other potentially useful cells such as myofibroblasts. Any of these cells may provide a source for differentiated cells and can provide an important feeder environment for the establishment or maintenance of stem cell cultures. The invention also relates to a method for isolating, purifying and culturally expanding UCMS cells derived from umbilical cord tissue and to characterization of and uses for such cells. The present invention is also directed to various methods and devices for treating various medical conditions. The methods and devices of the invention utilize isolated UCMS cells that under certain conditions, can be induced to differentiate into different cell lines. Human UCMS cell compositions are provided which serve as the progenitors for all UCMS stem cell lineages. The human stem cells of the invention can be used in the form of non-mitotic cells as a feeder cell collection.

Stem Cells from Umbilical Cord

The present invention is directed to a method of obtaining stem cells from umbilical cord matrix sometimes called mesenchyme or Wharton's Jelly, a source of stem cells that is inexhaustible, inexpensive, substantially free of cord blood and does not use cord blood or related cells as a source for useful cells.

The method of stem cell isolation comprises the steps of providing non-blood tissue specimen from umbilical cord containing UCMS cells, adding cells from the umbilical tissue specimen to a medium which contains factors that stimulate UCMS cell growth without differentiation and allows, when cultured, for the selective adherence of the UCMS stem cells to a substrate surface, culturing the specimen-medium mixture, and removing the non-adherent matter from the substrate surface.

Another aspect of the invention is the development of a bank of stem cells that can be tissue typed and banked and expanded as needed. Cells can be differentiated or genetically manipulated in vitro.

Another aspect of the invention is the development of cell populations that can be rendered mitotically inactive and then used as feeder cells for establishing and maintaining ES and EG cells from various species.

Yet another aspect of the invention is directed to a method for culture expanding the isolated and/or purified UCMS or UCMS derived stem cells. The method comprises the steps of providing a tissue specimen containing UCMS cells, adding cells from the specimen to a medium that contains factors that stimulate UCMS cell growth without differentiation and allows, when cultured, for the isolated UCMS cells to expand.

A further aspect of the present invention relates to a kit for isolating UCMS cells from an umbilical cord. The kit is comprised of a device to open the amnion of an umbilical cord. The kit is comprised of a medium containing a factor that can stimulate the growth of the UCMS cells without differentiation.

A further aspect of the invention relates to a cryopreservation kit for frozen storage of the umbilical cord tissue or the UCMS cells after isolation.

A further aspect of the invention relates to cell culture technology using the stem cells of the invention in a non-mitotic form as a feeder cell in combination with other stem cells, e.g., embryonic stem cells, capable of growth, transformation and use in treating human or animal disease or in agricultural applications.

A further aspect of the invention relates to cell culture technology using the stem cells of the invention in a treatment for diseases such as myelomonoblastic leukemia, Parkinson's Disease, stroke, or diabetes.

A further aspect of the invention relates to cell culture technology using the stem cells of the invention in a treatment using the homing potential of the UCMS cell.

Utilization of Umbilical Cord Matrix Stem Cells

Umbilical cord matrix Stem cells (UCMS) produced by the present invention have a range of possible uses (in all amniotic animals, such uses including a homing potential in which the cells proceed to the site) including but not limited to:

1) Regenerating tissues which have been damaged through acquired or genetic disease;

2) Treating a patient with damaged tissue or organs with UCMS cells combined with a biocompatible carrier suitable for delivering UCMS cells to the damaged tissue sites for correcting, repairing or modifying connective tissue disorders such as the regeneration of damaged muscle;

3) Producing various UCMS derived tissues;

4) Detecting, evaluating and isolating growth factors relevant to UCMS cells self-regeneration and differentiation into specific UCMS lineages;

5) Detecting, evaluating and isolating inhibitory factors which modulate UCMS cells commitment and differentiation into specific UCMS lineages;

6) Applying a UCMS cells to an area of connective tissue damage under conditions suitable for differentiating the cells into the type of connective tissue necessary for repair;

7) Developing UCMS cell lineages and assaying for factors associated with UCMS differentiation into various tissue types;

8) Various methods or devices for utilizing the UCMS cells in order to enhance hematopoietic cell production; and 9) Methods for using composite grafts of UCMS cells during bone marrow transplantation.

10) Methods for establishing and maintaining placental animal, including human, stem cell cultures using the UCMS cells as a species specific "feeder cell."

11) Methods for producing chimeric animals.

12) Methods of treating stroke, neurodegenerative diseases, diabetes, vascular conditions.

BRIEF DESCRIPTION OF THE FIGURES

FIGS. 6A and 6B illustrate Wharton's Jelly cells express neuron specific enolase (NSE). A) Immunocytochemical detection of NSE expressed 1 hour after induction treatment. B) Whole cell lysates of Wharton's Jelly cells that were preconfluent untreated, isolated colonies from confluent untreated or fully induced for 5 h were resolved by SDS-PAGE on 8-16% gradient gels and transferred to nitrocellulose. The blots were probed for the presence of NSE (predicted mass 38 kDa). Rat brain was used as a positive control.

FIGS. 7A and 7B illustrate that Wharton's Jelly cells express neurofilament M (NFM), a neuron specific intermediate filament. NF-M positive cells A) 1 and B) 3 days after long term induction. The induced Wharton's Jelly cells show an increasingly extensive network of processes on day 1 and day 3.

FIGS. 8A through 8C illustrate that TUJ1 is expressed after full induction of Wharton's Jelly cells. A) Immunoblot probed with TUJ1 of whole cell lysates from bFGF-treated (lane 1), and fully induced Wharton's Jelly cells after 1 day (lane 2), 5 days (lane 3) and 10 days (lane 4). Rat brain tissue lysate was used as a positive control (lane 5). (predicted molecular mass 50 kDa) B) Immunocytochemistry for TUJ1 after full induction of Wharton's Jelly cells. C) Immunoblot probed with TH, a marker for catecholaminergic neurons. (expected molecular mass 56 kDa). Rat brain (positive control, lane 1); untreated preconfluent Wharton's Jelly cells (lane 2); colonies of Wharton's Jelly cells (lane 3); Wharton's Jelly cells 3 days post-induction (lane 4).

FIGS. 9A through 9C illustrate that Wharton's Jelly cells express axon-specific protein GAP-43 after induction. A) Bright field and B) immunofluorescence micrographs of Wharton's Jelly cells grown on PDL/laminin for 10 days in long-term induction media. Cells were fixed and probed with anti-GAP43 and detected with FITC conjugated secondary antibody. C) Immunoblot probed with GAP-43 of lysates of Wharton's Jelly cells grown on plastic or PDL/Laminin 10 d post-induction or untreated Wharton's Jelly cells grown on plastic. (expected molecular mass 46 kDa).

FIGS. 10A through 10C illustrate expression of astrocyte (GFAP) and oligodendrocyte (CNPase) markers by Wharton's Jelly cells. (A) Stellate morphology of anti-GFAP reactive Wharton's Jelly cells 3 d post-induction. (B) Immunoblot probed for GFAP of whole-cell lysates of Wharton's Jelly cells that were either untreated or treated with neural inducing reagents 1 and 5 days post-induction (expected molecular mass 50 kDa). (C) Immunoblot probed for CNPase of whole-cell lysates of Wharton's Jelly cells that were either untreated, treated with bFGF alone overnight or 5 days after treatment with neural inducing reagents (expected molecular mass of 48 kDa).

FIGS. 18A through 18G illustrate UCMS cells induced to a neural phenotype in culture. In panels A-C, the change in cell morphology is shown in sequential photographs of a culture that was induced to differentiate along the neural lineage. Panel A shows uninduced UCMS cells. Panel B shows this same culture of cells after exposure to the full term induction (FI) protocol. Panel C shows the same cells after 10 days in the long term induction media (LTI). Inset: Note long processes and phase-bright cell body. The neurite-like short processes (arrows) and the growth cone-like projection at the distal end of a long process. Panels D-F illustrate that differentiated UCMS cells demonstrated positive immunocytochemical staining for neural markers: class III neuron-specific $\beta$-tubulin (TuJ1) (D), neurofilament medium (NF-M) (E), or a neuron-specific microtubule-associated protein, tau (F). Panel G illustrates high-power phase contrast micrograph of cell exposed to LTI protocol. Note: The granular material that resembles Nissl substance and the "neurites" with primary and secondary processes.

FIGS. 19A through 19D illustrate UCMS cells two weeks after transplantation. The same field is shown on the top and bottom. Left panels: Transplanted cells were identified by PKH 26 dye loading (A) or by expression of pig-specific NF70 immunocytochemical staining (C). The enclosed area is shown at higher magnification on the right (B and D, respectively). Right panels: Panel B shows the relatively simple morphology of the UCMS cells two weeks after transplantation into the rat brain. For the most part, the cells lack processes, have a granular cytoplasm and stain brightly with the PKH 26 dye. Panel D shows immunocytochemical staining for pig-specific NF70. The arrows indicate examples of cells that were both PKH 26-stained and positively immunocytochemically stained for NF70. The circles indicate UCMS cells that did not stain for NF70, suggesting that not all UCMS cells differentiate along the neural lineage following transplantation. The asterisks indicate cells that positively immunocytochemically stain for NF70 (panel D), but do not stain with PKH 26. Apparently, the PKH 26 dye loading did not stain 100% of the UCMS cells.

FIGS. 20A through 20D illustrate results demonstrating that transplanted UCMS cells expressed neural-specific markers in rat brain. Panel A, left: Pig UCMS cells, indicated by PKH 26 staining, 4 weeks after transplantation into rat brain. Note that the PKH 26 staining is usually confined to the cell bodies. Panel A, right: Identical field as shown in the left panel but with TuJ1 immunocytochemical staining. UCMS cells that stained for the neural-specific marker TuJ1 are indicated by arrows. Arrowheads indicate PKH-labeled fibers that stained positively for TuJ1. In panel A, the asterisks indicate PKH 26 positive cells that do not stain for TuJ1. Apparently, not all graft cells differentiate along the neural lineage. Panel B, left: Pig UCMS cells 4 weeks after transplantation. Panel B, right: Immunocytochemical staining for the $\beta$-III tubulin protein (a neuronal marker), TuJ1. The filled circles indicate the large number of double-labeled cells. In panel B, the asterisks indicate TuJ1-stained cells in the graft that are may not originate from the graft, they lack PKH 26 staining. Apparently, the graft stimulated endogenous stem cell migration and differentiation. The arrowheads indicate the location of TuJ1 immunocytochemical-positive fibers. Panel C shows the same field on the left and right. Panel C, left, shows engrafted UCMS cells. The right panel shows immunocytochemical staining for neuron-specific microtubule associated protein 2 (MAP2). The filled circles indicate the double-labeled cells. The asterisks indicate MAP2 stained cells that may not be of graft origin, they lack PKH 26. The arrowheads indicate MAP2 immunocytochemical-positive fibers. Panel D, left shows UCMS cells that were engineered to express eGFP and that were detected 4 weeks after transplantation. Note that most of the cells had a granular cytoplasm and a few had short primary processes. Panel D, right, shows that many of the eGFP expressing cells also stained for pig-specific NF70, which confirmed that they are of porcine origin. The filled circles indicate corresponding areas in both fields. There was a large percentage of double-labeled cells.

FIGS. 21A and 21B illustrate results of experiments in which pig UCMS cells were injected into the periphery. The UCMS cells were delivered intramuscularly into the semitendinosis and intravenously. FIG. 21A illustrates PHK 26-labeled cells that were found along the IM injection tract 4 weeks after injection. FIG. 21B illustrates PKH 26-labeled cells that were found within the parenchyma of the kidney. Finding transplanted UCMS cells 4 weeks after injection indicates that the immune system did not clear these cells from the body.

FIGS. 22A and 22B illustrate that previously disrupted PKH26-labeled UCMS cells did not label neurons or glia in rat brain following transplantation. FIG. 22A illustrates results from fluorescence activated cell sorting and demonstrating that about 99.8% of the PKH 26 dye loaded UCMS cells were disrupted by repeatedly sonic disruption prior to transplantation. FIG. 22B, left: One week after injection of disrupted PKH26-labeled cells, the area along the injection track was examined. While the background fluorescence was higher along the injection track, red blood cells were the only fluorescent cells found in this area (indicated by the arrowheads). No fluorescent neurons or glia were observed throughout the brain. FIG. 22B, right; In contrast, when intact PKH 26-labeled UCMS cells are injected, fluorescent cells were recovered in and around the injection tract 2-6 weeks following injection (the case shown was from a 4 week survival post injection). Note that the fluorescent graft cells (indicated by triangles in bottom panel) are larger and more irregular in appearance than the small, doughnut-shaped red blood cells indicated in the top panel. Calibration bar=20 microns.

FIGS. 23A through 23D illustrate results of experiments in which pig UCMS-eGFP cells were recovered after transplanting into rats with previous unilateral 6-OHDA striatal lesion. Pig UCMS cells expressing eGFP were transplanted at a very low density (approximately 150) into rat brain. The eGFP-pUCMS graft cells were recovered after 2, 4 and 8 weeks post-transplantation. A. The eGFP-pUCMS graft cells were identified by the green fluorescence by the GFP. B. The frozen brain sections were immunostained with GFP antibody and visualized by AMCA, which gave blue fluorescence in UV. The co-localization of AMCA with eGFP confirmed recovery of the graft cells. Almost all of the graft cells showed positive reaction with AMCA. C, D. Control staining performed without the primary antibody for GFP shows no reaction for AMCA.

FIGS. 24A through 24C illustrate results showing pig UCMS-eGFP graft cells 2, 4, and 8 weeks post-transplantation. The pig UCMS cells were recovered near the adjacent tract 2, 4, and 8 weeks following transplantation. A. Two weeks post-transplantation, the eGFP-pUCMS cells were recovered adjacent to the injection tract. They appear round (black arrow), granular, tend to form clumps (white arrow), and they have not migrated into the rat brain. B. Four weeks post-transplantation, the eGFP-pUCMS cells were not as clumped and were more dispersed in the rat brain tissue. Some of the cells appeared elongated (black arrow) and some appeared to be extending small processes (white arrow). The graft cells were scattered around the cannula tract. C. Eight weeks post-transplantation, the eGFP-pUCMS cells appeared to be bigger in size (black arrow) than after 2 and 4 weeks. A more diffused staining was noticed in the brain tissue around the cannula tract.

FIGS. 27A and 27B illustrate results of assessment of transplanted pig UCMS cell number over time after transplantation. At each survival time, the cell size distributions were compared and found to be not significantly different. Thus the data from both animals at each survival period was pooled and statistically compared to the other survival periods. The average cell size at specific survival period is shown in A. Note that the cell size increases at the longer survival periods. B. Based upon the average cell size, the total number of pig UCMS cells was estimated in each animal. Thus, the cells undergo about a five fold expansion in the first two weeks and increase to a maximum of about a seven fold expansion by the eighth week. N=2 at 2, 4 and 8 weeks. * $P<0.05$.

FIGS. 28A through 28D illustrate results demonstrating that pig UCM-eGFP cells formed TH-positive cells after transplanting into rats with previous unilateral 6-OHDA striatal lesion. A. The eGFP-pUCMS graft cells were identified by the green fluorescence by the GFP. B. The frozen brain sections were immunostained with TH antibody and visualized by AMCA, which gave blue fluorescence in UV. The co-localization of AMCA with eGFP confirmed the TH-positive graft cells (white arrow heads), which were differentiated from the TH-negative graft cells (white stars). C, D. Control staining performed without the primary antibody for GFP shows no reaction for AMCA (white arrow heads).

FIGS. 29A and 29B illustrate results of assessment of transplanted pig UCMS cells for percentage and number of TH-positive graft cells over the time. A. The percentage of TH-stained graft cells was determined in at least ten fields per animal. The percentage of TH-stained graft cells increased over the time (1% at 2 weeks to about 6% at 8 weeks post-transplantation). B. Based upon the total number of graft cells (see FIG. 26 above) and the percentage of TH stained graft cells, the number of TH-positive graft cells was estimated. The number of TH-positive graft cells increased from about 50 at 2 weeks to about 1200 cells at 8 weeks post-transplantation. * $P<0.05$.

DETAILED DESCRIPTION OF THE INVENTION

Summary

Figure 1:
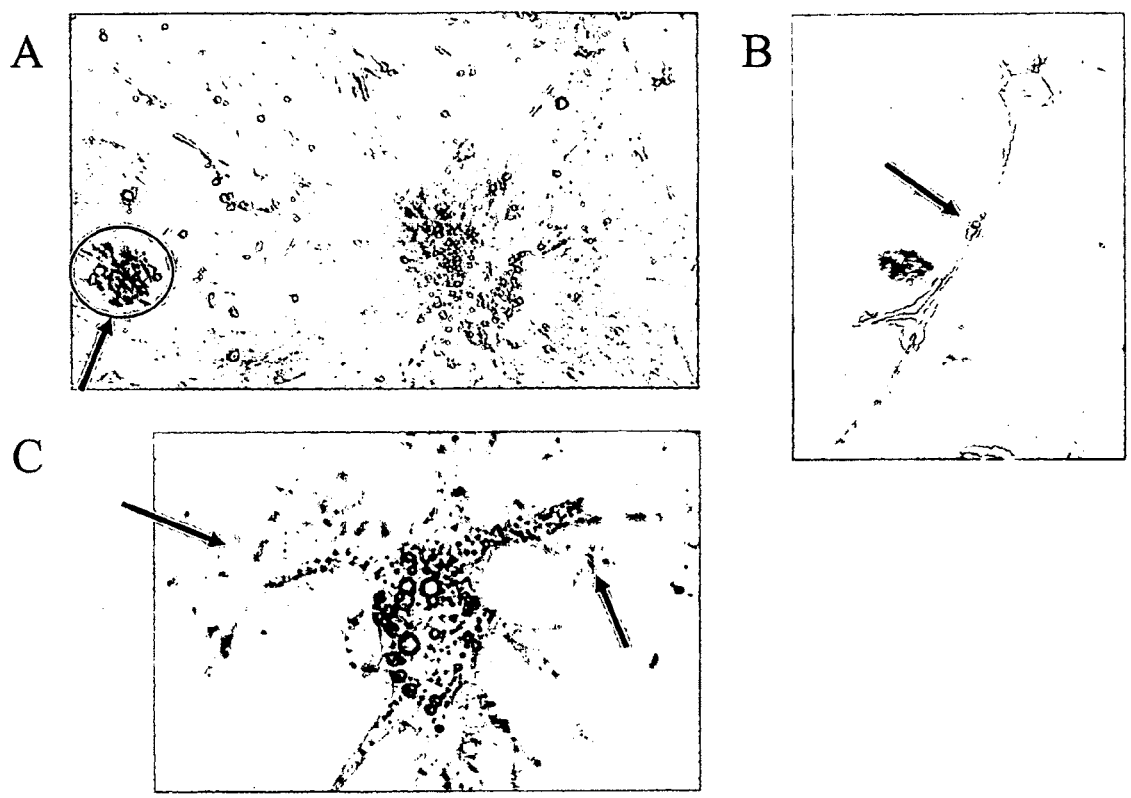
FIG. 1A through 1C illustrate the neuron-like morphology of Wharton's Jelly cells after induction. A) Uninduced colonies of Wharton's Jelly cells (arrow) B) Typical neuron-like cell with long axon-like process (arrow) 3 days after long-term induction. C) High (40×) magnification phase-contrast view of a long-term induced Wharton's Jelly cell after three days. Note the multiple neurites with primary and secondary processes (arrows).

The present invention relates to a method for obtaining stem cells from umbilical cord matrix (e.g., Wharton's Jelly) an umbilical cord mucous connective tissue, involving:

1) Methods for isolating UCMS cells from umbilical cord matrix (e.g.) Wharton's Jelly of the umbilical cord;

2) Methods for mitotically expanding the populations of isolated UCMS cells, collectively the cells of the invention; and 3) Methods for culturing mitotically expanded populations of the cells of the invention under conditions that permit or induce the formation of new tissue.

The invention also relates to the products of these methods, including but not limited to, the cells of the invention, mitotically expanded or otherwise and the new tissue produced therefrom. The invention also relates to the use of these cells, constructs and tissues in vivo to repair, replace or augment tissues or organs of the animal or human or, in vitro, to form tissue cultures which are useful to produce new tissue or bioactive agents or to test the therapeutic or cytotoxic effects of potential therapeutic agents.

In addition, the UCMS cells of the invention can be cryopreserved and stored frozen. By this process, "banks" of UCMS cells that can be used to produce new tissue at any time to replace that lost to disease or trauma.

For supplying cell or tissue grafts, the cells of the invention could be used in two ways. Either the cells of an individual could be obtained and cryopreserved to be used at any time in the subject's life to replace damaged or diseased tissue or placed in a bank for use as "ubiquitous donor cells" or "cells with a homing potential" to produce tissue for use in any subject in need.

The cells of this invention could be used as feeders, feeder cells or feeder cultures to support stem cells or sources of conditioned media or extra cellular matrix to support stem cells of various species. The feeders might be of the same or a different species as the targeted stem cells.

Definitions

"Umbilical Cord Matrix Stem (UCMS) Cell"

The term "Umbilical Cord Matrix Stem Cell" as used herein refers to either:

1) A pluripotent, or lineage-uncommitted progenitor cell, typically referred to in the art as a "stem cell" derived from the umbilical cord matrix, other than a cord blood cell source. Such a cell is potentially capable of an unlimited number of mitotic divisions to either renew its line or to produce progeny cells which will differentiate into the mature functional cells that will constitute most of the tissues of an organism such as tissues derived from any of the three germ layers (ectoderm, endoderm, neuroderm) and germ cells; or 2) A lineage-committed progeny cell produced from the mitotic division of a stem cell of the invention that can eventually differentiate into any of the three germ layer derivatives or germ cells. Unlike the stem cell from which it is derived, the lineage-committed progeny cell is generally considered to be incapable of an unlimited number of mitotic divisions to produce other progeny cells.

The invention is directed primarily to compositions and methods for the production of UCMS cells and their derivatives such as any of the three germ layer derivatives or germ cell lines and cells, tissues and organs. However the invention may also be practiced so as to produce stem cells and their derivatives in any amniote in need thereof.

According to the invention, stem cells may be obtained from UCMS cell source such as Wharton's Jelly collected from a subject's own umbilical cord. Alternatively, it may be advantageous to obtain stem cells from Wharton's Jelly obtained from an umbilical cord associated with a species specific or species related developing fetus or newborn, where the subject in need of treatment is one of the parents of the fetus or newborn. Another scenario involves banking and tissue typing and cataloging so that any individual in need of a stem cell graft might find an appropriate match.

Alternatively, because of the primitive nature of cells isolated from Wharton's Jelly, immune rejection of the cells of the invention or the new tissue produced therefrom may be minimized. As a result, such cells may be useful as "ubiquitous donor cells" for the production of new cells and tissue for use in any subject in need thereof.

"Wharton's Jelly"

The term "Wharton's Jelly," also known as inter-laminar jelly, as used herein, is a subset of UCMS, and refers to a mucous-connective tissue substance found in the umbilical cord. The components of Wharton's Jelly include a mucous connective tissue in which are found myofibroblasts, fibroblasts, collagen fibers and an amorphous ground substance composed of hyaluronic acid and possibly other as yet uncharacterized cell populations. Wharton's Jelly is one component of the umbilical cord matrix and can be a source of the stem cells used in the invention.

"Umbilical Cord"

The term "Umbilical Cord" as used herein, refers to the Umbilical cord-structure enclosing the body stalk, and the stalks of the yolk sac and allantois. The enclosing membrane of the umbilical cord is formed by the folding of the amnion.

"Amniote"

The term "amniote" or "amniote species" as used herein, refers to any animal that has an amnion. This includes mammals, reptiles and birds.

"Feeder Cell" or "Feeder Cell Culture"

For the purpose of this disclosure, the term "feeder cell" or "feeder cell culture", as used herein, refers to cells that provide a co-stimulating function in conjunction with typically the other stem cell cultures, not necessarily the cells of this invention. A feeder cell can be obtained by culture techniques known in the art such as that shown by Weaver et al., Blood 82:1981-1984, 1993. Feeder cell cultures can be stored by cryopreservation in liquid nitrogen until use. Prior to the use of such feeder cells, for the purpose of maintaining a culture of stem cells (other than the feeder cells), such feeder cells are stabilized to promote the isolation and maintenance of stem cell cultures. "Homing potential" refers to an inherent capacity of a cell to be targeted to specific locations for therapeutic function or purpose.

DESCRIPTION OF THE INVENTION

The invention is divided into the following non-limiting sections solely for the purpose of description:
1) Obtaining umbilical cord;
2) Method of obtaining UCMS cells from Wharton's Jelly;
3) Establishing and maintaining stem cells to a cell culture;
4) Establishing the stem cells into a transplantable cell;
5) Foreign gene introduction;
6) Development of a stem cell bank;
7) Feeder Culture Cells; and
9) Uses of the UCMS cells (1) Obtaining Umbilical Cord In order to isolate the stem cells according to the invention, umbilical cord is obtained under sterile conditions immediately following the termination of pregnancy (either full term or pre-term). The umbilical cord or a section thereof, according to one embodiment of the invention, may be transported from the site of the delivery to a laboratory in a sterile container containing a preservative medium. One example of such a preservative medium is Dulbecco's Modified Eagle's Medium (DMEM) with HEPES buffer.

The umbilical cord is preferably maintained and handled under sterile conditions prior to and during the collection of the stem cells from the matrix or Wharton's Jelly and may additionally be surface-sterilized by brief surface treatment of the cord with, for example, an aqueous (70% ethanol) solution or betadine, followed by a rinse with sterile, distilled water. The umbilical cord can be briefly stored for up to about three hours at about 3-5° C., but not frozen, prior to extraction of UCMS cell(s) from the cellular source including the Wharton's Jelly umbilical component.

Wharton's Jelly is collected from the umbilical cord under sterile conditions by an appropriate method known in the art. For example, the cord is cut transversely with a scalpel, for example, into approximately one inch sections, and each section is transferred to a sterile container containing a sufficient volume of phosphate buffered saline (PBS) containing $CaCl_2$ (0.1 g/l) and $MgCl_2.6H_2O$ (0.1 g/l) to allow surface blood to be removed from the section by gentle agitation. The section is then removed to a sterile-surface where the outer layer of the section is sliced open along the cord's longitudinal axis. The blood vessels of the umbilical cord (two veins and an artery) are dissected away, for example, with sterile forceps and dissecting scissors, and the umbilical cord is collected and placed in a sterile container, such as a 100 mm TC-treated Petri dish. The umbilical cord may then be cut into smaller sections, such as 2-3 mm³ for culturing.

(2) Method of Obtaining UCMS Cells from Wharton's Jelly

Umbilical cord is incubated in vitro in culture medium under appropriate conditions to permit the proliferation of any UCMS cells present therein. Cells can be isolated from explants of the umbilical cord or freed enzymatically e.g., collagenase or trypsin. Any appropriate type of culture medium can be used to isolate the stem cells of the invention, such as, but not limited to DMEM. The culture medium may be supplemented with one or more components including, for example, fetal bovine serum, equine serum, human serum and one or more antibiotics and/or mycotics to control microbial contamination. Examples of antibiotics include but are not limited to penicillin G, streptomycin sulfate, amphotericin B, gentamycin, and nystatin, either alone or in combination.

Methods for the selection of the most appropriate culture medium, medium preparation, and cell culture techniques are well known in the art and are described in a variety of sources, including Doyle et al., (eds.), 1995, Cell and Tissue Culture: Laboratory Procedures, John Wiley & Sons, Chichester; and Ho and Wang (eds.), 1991, Animal Cell Bioreactors, Butterworth-Heinemann, Boston, which are incorporated herein by reference.

Another method relies on enzymatic dispersion of Wharton's Jelly with collagenase and isolation of cells by centrifugation followed by plating.

(3) Establishment of UCMS Cells in Cell Culture

The method involves fractionating the source of cells (Wharton's Jelly) into two fractions, one of which is enriched with a stem cell and thereafter exposing the stem cells to conditions suitable for cell proliferation. The cell enriched isolate thus created comprises stem cells.

After culturing Wharton's Jelly for a sufficient period of time, for example, about 10-12 days, UCMS derived stem cells present in the explanted tissue will tend to have grown out from the tissue, either as a result of migration therefrom or cell division or both. These UCMS derived stem cells may then be removed to a separate culture vessel containing fresh medium of the same or a different type as that used initially, where the population of UCMS derived stem cells can be mitotically expanded.

Alternatively, the different cell types present in Wharton's Jelly can be fractionated into subpopulations from which UCMS derived stem cells can be isolated. This may be accomplished using standard techniques for cell separation including, but not limited to, enzymatic treatment to dissociate Wharton's Jelly into its component cells, followed by cloning and selection of specific cell types (for example, myofibroblasts, stem cells, etc.), using either morphological or biochemical markers, selective destruction of unwanted cells (negative selection), separation based upon differential cell agglutinability in the mixed population as, for example, with soybean agglutinin, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis, and fluorescence activated cell sorting (FACS). For a review of clonal selection and cell separation techniques, see Freshney, 1994, Culture of Animal Cells; A Manual of Basic Techniques, 3d Ed., Wiley-Liss, Inc., New York, which is incorporated herein by reference.

In a preferred embodiment for culturing UCMS derived stem cells, Wharton's Jelly is cut into sections of approximately 2-3 mm³, and placed in a TC-treated Petri dish containing glass slides on the bottom of the Petri dish. The tissue sections are then covered with another glass slide and cultured in a complete medium, such as, for example, Dulbecco's MEM plus 20% FBS; or RPMI 1640 containing 10% FBS, 5% ES and antimicrobial compounds, including penicillin G (100 μg/ml), streptomycin sulfate (100 μg/ml), amphotericin (250 .mu.g/ml), and gentamicin (10 μg/ml), pH 7.4-7.6. The tissue is preferably incubated at 37-39° C. and 5% $CO_2$ for 10-12 days. A further example of a defined media is DMEM, 40% MCDB201, 1× insulin-transferrin-selenium, 1× linoleic acid-BSA, 10-8 M dexamethasone, 10-4 M ascorbic acid 2-phosphate, 100 U penicillin, 1000 U streptomycin, 2% FBS, 10 ng/mL EGF, 10 ng/mL PDGF-BB.

The medium is changed as necessary by carefully aspirating the medium from the dish, for example, with a pipette, and replenishing with fresh medium. Incubation is continued as above until a sufficient number or density of cells accumulates in the dish and on the surfaces of the slides. For example, the culture obtains approximately 70 percent confluence but not to the point of complete confluence. The original explanted tissue sections may be removed and the remaining cells are trypsinized using standard techniques. After trypsinization, the cells are collected, removed to fresh medium and incubated as above. The medium is changed at least once at 24 hr post-trypsin to remove any floating cells. The cells remaining in culture are considered to be UCMS derived stem cells.

Once the stem cells have been isolated, their population is expanded mitotically. The stem cells should be transferred or "passaged" to fresh medium when they reach an appropriate density, such as $3\times10^4$-$cm^{-2}$ to $6.5\times10^4$-$cm^{-2}$, or, for example, when they reach a defined percentage of confluency on the surface of a culture dish. During incubation of the stem cells, cells can stick to the walls of the culture vessel where they can continue to proliferate and form a confluent monolayer. Alternatively, the liquid culture can be agitated, for example, on an orbital shaker, to prevent the cells from sticking to the vessel walls. The cells can also be grown on Teflon-coated culture bags.

In a preferred embodiment, the desired mature cells or cell lines are produced using stem cells that have gone through a low number of passages. We, however, have maintained cells for more than 100 population doublings. The invention contemplates that once stem cells have been established in culture, their ability to serve as progenitors for mature cells or cell lines can be maintained, for example, by regular passage to fresh medium as the cell culture reaches an appropriate density or percentage of confluency, or by treatment with an appropriate growth factors, or by modification of the culture medium or culture protocol, or by some combination of the above.

(4) Establishing the Stem Cell into a Transplantable Culture

The invention also includes a method of developing transplantable cells by exposing the stem cells to differentiating or growth factors. The transplantable cell may be a cell derived from any of the three germ layers, a neural cell, or other cell. The cell can have a homing capacity. The present invention can also include differentiating the stem cells and establishing the stem cells into a transplantable cell.

Once established, a culture of UCMS cells may be used to produce mature cells or cell lines. Differentiation of stem cells to mature cells can be triggered by the addition to the culture medium of Wnt suppressors or specific exogenous growth factors, such as, for example, bFGF, BMPs such as BMP-13, or TGF-β, with or without antioxidants.

(5) Foreign Gene Introduction

The invention also includes a method of introducing a foreign gene into a UCMS cell by contacting the stem cell with a factor comprising a foreign gene. UCMS cells can be genetically engineered to express genes for specific types of growth factors.

In a non-limiting embodiment, the cells of the invention, for example, may be genetically engineered to express and produce growth factors such as BMP-13 or TGF-β. For example, the gene or coding sequence for TGF-β would be placed in operative association with a regulated promoter so that production of TGF-β in culture can be controlled. If desired, the cells of the invention may be genetically engineered to produce other gene products beneficial to transplantation, e.g., anti-inflammatory factors, e.g., anti-GM-CSF, anti-TNF, anti-IL-1, anti-IL-2, etc.

Alternatively, the cells may be genetically engineered to "knock out" expression of native gene products that promote inflammation, e.g., GM-CSF, TNF-α, IL-1, IL-2, or "knock out" expression of MHC in order to lower the risk of rejection. In addition, the cells may be genetically engineered for use in gene therapy to adjust the level of gene activity in a patient to assist or improve the results of tissue transplantation. The genetically engineered cells may then be screened to select those cell lines that: 1) bring about the amelioration of symptoms of rheumatoid disease or inflammatory reactions in vivo, and/or 2) escape immunological surveillance and rejection.

(6) Stem Cell Bank

The invention includes a method of generating a bank of stem cells by obtaining matrix cells from the umbilical cord, fractionating the matrix into a fraction enriched with a stem cell and culturing the stem cells in a culture medium containing one or more growth factors. By this process, the stem cells will undergo mitotic expansion. Alternatively, a bank of the umbilical cord itself and/or unfractionated cells may be maintained for later obtaining matrix cells.

The invention contemplates the establishment and maintenance of cultures of stem cells as well as mixed cultures comprising stem cells, mature cells and mature cell lines. Once a culture of stem cells or a mixed culture of stem cells and mature cells is established, the cultures should be transferred to fresh medium when sufficient cell density is reached. By this means, formation of a monolayer of cells should be prevented or minimized, for example, by transferring a portion of the cells to a new culture vessel and into fresh medium. Alternatively, the culture system can be agitated prevent the cells from sticking or grown in Teflon-coated culture bags.

Once the cells of the invention have been established in culture, as described above, they may be maintained or stored in "cell banks" comprising either continuous in vitro cultures of cells requiring regular transfer, or, preferably, cells which have been cryopreserved.

Cryopreservation of cells of the invention may be carried out according to known methods, such as those described in Doyle et al., 1995, Cell and Tissue Culture. For example, but not by way of limitation, cells may be suspended in a "freeze medium" such as, for example, culture medium further comprising 15-20% FBS and 10% dimethylsulfoxide (DMSO), with or without 5-10% glycerol, at a density, for example, of about $4-10 \times 10^6$ cells-ml$^{-1}$. The cells are dispensed into glass or plastic ampoules (Nunc) that are then sealed and transferred to the freezing chamber of a programmable freezer. The optimal rate of freezing may be determined empirically. For example, a freezing program that gives a change in temperature of about $-1°$ C.-min$^{-1}$ through the heat of fusion may be used. Once the ampoules have reached about $-180°$ C., they are transferred to a liquid nitrogen storage area. Cryopreserved cells can be stored for a period of years, though they should be checked at least every 5 years for maintenance of viability.

The cryopreserved cells of the invention constitute a bank of cells, portions of which can be "withdrawn" by thawing and then used to produce new stem cells, etc. as needed. Thawing should generally be carried out rapidly, for example, by transferring an ampoule from liquid nitrogen to a 37 degree C. water bath. The thawed contents of the ampoule should be immediately transferred under sterile conditions to a culture vessel containing an appropriate medium such as RPMI 1640, DMEM conditioned with 20% FBS. The cells in the culture medium are preferably adjusted to an initial density of about $3 \times 10^5$ cells-ml$^{-1}$-$6 \times 10^5$ cells-ml$^{-1}$ so that the cells can condition the medium as soon as possible, thereby preventing a protracted lag phase. Once in culture, the cells may be examined daily, for example, with an inverted microscope to detect cell proliferation, and sub-cultured as soon as they reach an appropriate density.

The cells of the invention may be withdrawn from the bank as needed, and used for the production of new tissue either in vitro, or in vivo, for example, by direct administration of cells to the site where new tissue is needed. As described supra, the cells of the invention may be used to produce new tissue for use in a subject where the cells were originally isolated from that subject's umbilical cord (autologous).

Alternatively, the cells of the invention may be used as ubiquitous donor cells, i.e., to produce new tissue for use in any subject (heterologous).

(7) Feeder Culture Cells

In an embodiment, the stem cells of the invention can be employed to create feeder cell culture materials. The present cells can be used for species specific or other appropriate feeder culture cells for ES, EG or other stem cells (for example, neural stem cells).

The stem cells of the application can be used in the form of the feeder cells that remain alive, that can produce growth factor and other materials for maintaining culture materials, but that do not divide or grow. The feeder cells can be prevented from beginning or conducting a mitotic process by using irradiation, chemical treatment, or another technique that can prevent such processes. After performing such a technique, the feeder cells are alive and can function, but will not divide or grow. In using feeder cells to culture the stem cells of the invention, the feeder cells can, for example, provide growth factors to the growing totipotent, pluripotent, or multipotent stem cells. Growth factors can be added to the culture if the feeder cells are incapable of providing sufficient quantities. The feeder cells can be grown and selected such that they express selected growth factors, for example, factors useful in the manufacture of neural, epithelial or other such desirable cell types and characteristics.

In an embodiment, the feeder cells are treated to prevent mitotic transformations or are inactivated prior to use. In an embodiment, the feeder cells are inactivated using radiation or chemical treatment. Radiation useful for such transformation can include X-radiation, gamma radiation, or electron radiation from appropriate sources. X-radiation can be used from electronic generation or from agents such as cobalt or cesium. Chemical treatments can be made with agents such as Mitomycin C. The resulting inactivated feeder cells can be cultured in culturing PGC's, for example, for 24 hours prior to culturing with a stem cell material. Fresh isolates can be taken on a regular basis to ensure that the cells are continually available.

Feeder cell layers can be useful for both the isolation of stem cell lines from embryos and other sources and for the routine maintenance of established cell lines. UCMS cells can be typically plated to give a uniform monolayer of cells onto which the stem cells are seeded. Species-specific feeder cells can provide adequate growth conditions for successful culture development.

The stem cells can be isolated for feeder cell purposes, and other purposes, by obtaining Wharton's Jelly through dissection of the umbilical cord. Once isolated from the umbilical cord, the UCMS cells can be dispersed and suspended in an aqueous medium such as trypsin EDTA solution. Adding DMEM solution plus serum can neutralize the trypsin. The contents of the dish are transferred to a 10 ml conical tube. The tube is then centrifuged or held stationary to settle large particulate materials. UCMS stem cells in the supernatant can be plated with standard growth medium and maintained with conventional culture technique.

The use of the stem cells of this invention as a feeder cell in stem cell cultures provides a number of advantages. First, the cells are stem cells and provide growth factors that are applicable to other human stem cells from other sources such as embryonic sources, adult sources such as blood sources, adipose or fat sources and other human sources. Further, the use of human stem cells derived from Wharton's Jelly provides a final cell culture in which the feeder cells do not prevent the use of the cultured stem cells from application in human use. Such feeder cell cultures can be made using known techniques.

(8) Uses of the UCMS Derived Stem Cells

The cells of the invention may be used in human or animal medicine, agriculturally important species and in research. For example the cells of the invention may be used to treat subjects requiring the repair or replacement of body tissues resulting from disease or trauma. Treatment may entail the use of the cells of the invention to produce new tissue, and the use of the tissue thus produced, according to any method presently known in the art or to be developed in the future. For example, the cells of the invention may be implanted, injected or otherwise administered directly to the site of tissue damage so that they will produce new tissue in vivo.

In addition, the UCMS cells, the mature cells produced from these stem cells, the cell lines derived from these stem cells, and the tissue of the invention can be used:

(1) to screen for the efficacy and/or cytotoxicity of compounds, allergens, growth/regulatory factors, pharmaceutical compounds, etc.;

(2) to elucidate the mechanism of certain diseases;

(3) to study the mechanism by which drugs and/or growth factors operate;

(4) to diagnose, monitor and treat cancer in a patient;

(5) for gene therapy;

(6) to produce biologically active products;

(7) to target delivery of a drug to a specific tissue. To do this they may first be engineered to produce the drug;

(8) to be utilized for their homing ability that permits the cells to migrate from a treatment location to a specific target location (for example, where a pathology or abnormal condition exists);

(9) to produce beta cells for insulin production; and

(10) for transplantation to treat neurodegenerative disease, stroke, reperfusion injuries, and other vascular conditions.

(11) to produce transgenic animals by the method of injecting transgenic UCMS cells into early embryos (morulae and/or blastocysts) to produce chimeric embryos and individuals

(12) to preserve or rescue the genetic material of endangered species or genetic stocks of strains of agricultural or laboratory animals.

(1) Screening Effectiveness and Cytotoxicity of Compounds

The cells and tissues of the invention may be used in vitro to screen a wide variety of compounds for effectiveness and cytotoxicity of pharmaceutical agents, growth/regulatory factors, anti-inflammatory agents, etc. To this end, the cells of the invention, or tissue cultures described above, are maintained in vitro and exposed to the compound to be tested. The activity of a cytotoxic compound can be measured by its ability to damage or kill cells in culture. This may readily be assessed by vital staining techniques. Analyzing the number of living cells in vitro, e.g., by total cell counts, may assess the effect of growth/regulatory factors and differential cell counts. This may be accomplished using standard cytological and/or histological techniques, including the use of immunocytochemical techniques employing antibodies that define type-specific cellular antigens. The effect of various drugs on the cells of the invention either in suspension culture or in the three-dimensional system described above may be assessed.

(2) Elucidate the Mechanism of Certain Diseases

The cells and tissues of the invention may be used as model systems for the study of physiological or pathological conditions. For example, the cells and tissues of the invention may be used to determine the nutritional requirements of a tissue under different physical conditions, e.g., intermittent pressurization, and by pumping action of nutrient medium into and out of the tissue construct. This may be especially useful in studying underlying causes for age-related or injury-related disorders.

(3) Study the Mechanism by which Drugs and/or Growth Factors Operate

The stem cells, cell lines, mature cells and tissues of the invention may also be used to study the mechanism of action of morphagens, chemokines, cytokines, and other pro-inflammatory mediators, e.g., IL-1, TNF and prostaglandins. In addition, cytotoxic and/or pharmaceutical agents can be screened for those that are most efficacious for a particular application. Agents which prove to be efficacious in vitro could then be used to treat the patient therapeutically.

(4) Diagnosis, Monitoring and Treatment of Cancer or Cancer Cells, Tissues or Symptoms Based upon their tropism for tissue pathology, the cells and tissues of the invention may be used to diagnose, treat or monitor cancer or reduce its symptoms.

(5) Gene Therapy

The cells and tissues of the present invention may afford a vehicle for introducing genes and gene products in vivo to assist or improve the results of implantation and/or for use in gene therapies. The following description is directed to the genetic engineering of any of the cells of the invention or tissues produced therefrom.

Cells which express a gene product of interest, or the tissue produced in vitro therefrom, can be implanted into a subject who is otherwise deficient in that gene product. For example, genes that express a product capable of preventing or ameliorating symptoms of various types of diseases, such as those involved in preventing inflammatory reactions, may be under-expressed or down-regulated under disease conditions. Alternatively, the activity of gene products may be diminished, leading to the manifestation of some or all of the pathological conditions associated with a disease. In either case, the level of active gene product can be increased by gene therapy, i.e., by genetically engineering cells of the invention to produce active gene product and implanting the engineered cells, or tissues made therefrom, into a subject in need thereof. A related application foreseen in agricultural or other animals is the delivery of a product that enhances growth, maturation, reproduction, etc. The products of interest may be delivered over the long term or alternatively and transiently to achieve the desired effect.

Alternatively, the cells of the invention can be genetically engineered to produce a gene product that would serve to stimulate tissue or organ production such as, for example, BMP-13 or TGF-β. Also, for example, the cells of the invention may be engineered to express the gene encoding the human complement regulatory protein that prevents rejection of a graft by the host. See, for example, McCurry et al., 1995, Nature Medicine 1:423-427.

A related application foreseen in animals is the use of these cells to generate transgenic animals using methods that have been developed for mouse ES cells. The chimeric animals will be used to establish transgenic animal lines. Another related application foreseen in animals is the use of these cells to generate chimeric animals that produce useful compounds.

Methods that may be useful to genetically engineer the cells of the invention are well-known in the art. For example, a recombinant DNA construct or vector containing the gene of interest may be constructed and used to transform or transfect one or more cells of the invention. Such transformed or transfected cells that carry the gene of interest, and that are capable of expressing said gene, are selected and clonally expanded in culture. Methods for preparing DNA constructs containing the gene of interest, for transforming or transfecting cells, and for selecting cells carrying and expressing the gene of interest are well-known in the art. See, for example, the techniques described in Maniatis et al., 1989, Molecular Cloning, A Laboratory Manual, Cold Spring Harbor Laboratory Press, Cold Spring Harbor, N.Y.; Ausubel et al., 1989, Current Protocols in Molecular Biology, Greene Publishing Associates & Wiley Interscience, N.Y.; and Sambrook et al., 1989, Molecular Cloning: A Laboratory Manual, 2nd Ed., Cold Spring Harbor Laboratory Press, Cold Spring Harbor, N.Y. In addition, the transkaryotic implantation technique described by Seldon et al., 1987, Science 236:714-718, may be useful. All of these publications are incorporated herein by reference.

The cells of the invention can be engineered using any of a variety of vectors including, but not limited to, integrating viral vectors, e.g., retrovirus vector or adeno-associated viral vectors, or non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Host cells are preferably transformed or transfected with DNA controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines that express the gene product.

Any promoter may be used to drive the expression of the inserted gene. For example, viral promoters include but are not limited to the CMV promoter/enhancer, SV 40, papillomavirus, Epstein-Barr virus, elastin gene promoter and β-globin. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters include, but are not limited to, those associated with metallothionein and heat shock protein.

Examples of transcriptional control regions that exhibit tissue specificity which have been described and could be used include but are not limited to: elastase I gene control region, which is active in pancreatic acinar cells (Swit et al., 1984, Cell 38:639-646; Ornitz et al., 1986, Cold Spring Harbor Symp. Quant. Biol. 50:399-409; MacDonald, 1987, Hepatology 7:425-515); insulin gene control region, which is active in pancreatic beta cells (Hanahan, 1985, Nature 315:115-122); immunoglobulin gene control region, which is active in lymphoid cells (Grosschedl et al., 1984, Cell 3S:647-658; Adams et al., 1985, Nature 318:533-538; Alexander et al., 1987, Mol. Cell. Biol. 7:1436-1444); myelin basic protein gene control region, which is active in oligodendrocyte cells in the brain (Readhead et al., 1987, Cell 48:703-712); myosin light chain-2 gene control region, which is active in skeletal muscle (Shani, 1985, Nature 314:283-286); and gonadotropic releasing hormone gene control region, which is active in the hypothalamus (Mason et al., 1986, Science 234:1372-1378).

The cells of the invention may be genetically engineered to "knock out" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a specific cell can be reduced or knocked out using a number of techniques including, for example, inhibition of expression by inactivating the gene completely (commonly termed "knockout") using the homologous recombination technique. Usually, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted (Mombaerts et al., 1991, Proc. Nat. Acad. Sci. U.S.A. 88:3084-3087).

Antisense and ribozyme molecules that inhibit expression of the target gene can also be used in accordance with the invention to reduce the level of target gene activity. For example, antisense RNA, small interfering RNA (siRNA), and ribozyme molecules that inhibit the expression of major histocompatibility gene complexes (HLA) have been shown to be most versatile with respect to immune responses. Still further, triple helix molecules can be utilized in reducing the level of target gene activity. These techniques are described in detail by L. G. Davis et al. (eds), 1994, Basic Methods in Molecular Biology, 2nd ed., Appleton & Lange, Norwalk, Conn., which is incorporated herein by reference.

Once the cells of the invention have been genetically engineered, they may be directly implanted into the patient to allow for the amelioration of the symptoms of disease by, for example, producing an anti-inflammatory gene product such as, for example, peptides or polypeptides corresponding to the idiotype of neutralizing antibodies for GM-CSF, TNF, IL-1, IL-2, or other inflammatory cytokines. Alternatively, the genetically engineered cells may be used to produce new tissue in vitro, which is then implanted in the subject, as described supra.

The use of the compositions and methods of the invention in gene therapy has a number of advantages. Firstly, since the culture comprises eukaryotic cells, the gene product will likely be properly expressed and processed to form an active product. Secondly, gene therapy techniques are generally useful where the number of transfected cells can be substantially increased to be of clinical value, relevance, and utility. Thus, for example, the three-dimensional culture described supra allows for mitotic expansion of the number of transfected cells and amplification of the gene product to levels that may be efficacious in treating congenital or acquired disease. Transplant of HLA matched cells, used banked cells, etc. are all advantages.

(6) Production of Biological Molecules

In a further embodiment, the cells of the invention can be cultured in vitro to produce biological products in high yield. For example, such cells, which either naturally produce a particular biological product of interest (e.g., a growth factor, regulatory factor, or peptide hormone etc.), or have been genetically engineered to produce a biological product, could be clonally expanded using, for example, the three-dimensional culture system described above. If the cells excrete the biological product into the nutrient medium, the product can be readily isolated from the spent or conditioned medium using standard separation techniques, e.g., such as differential protein precipitation, ion-exchange chromatography, gel filtration chromatography, electrophoresis, and HPLC, to name but a few. A "bioreactor" may be used to take advantage of the flow method for feeding, for example, a three-dimensional culture in vitro. Essentially, as fresh media is passed through the three-dimensional culture, the biological product is washed out of the culture and may then be isolated from the outflow, as above.

Alternatively, a biological product of interest may remain within the cell and, thus, its collection may require that the cells be lysed. The biological product may then be purified using any one or more of the above-listed techniques.

(7) Targeted Drug Delivery

The UCMS cells can be used to target delivery of a drug to a specific tissue. To do this they can first be engineered to produce the drug. A foreign gene is integrated in vitro into the genome of the umbilical cord matrix stem cells by lipofection or electroporation, a foreign protein or peptide is expressed, and the stem cells are introduced in the host tissue either as undifferentiated cells or after differentiation in vitro. The engineered UCMS cells can be cellular isografts, allografts or xenografts.

The present invention may be better understood with reference to the following examples. These examples are intended to be representative of specific embodiments of the invention, and are not intended as limiting the scope of the invention.

EXAMPLES

Example 1

UCMS Cells as Neural Cell Precursors

This experiment tested the hypothesis that Wharton's Jelly hold useful stem cells in an undifferentiated state. The Wharton's Jelly cells were identified as an easily attainable source of potentially multi-potent stem cells that can be maintained in culture.

Materials and Methods

Umbilical cords were collected and the serosa opened. Two types of sample were prepared. One was adherent to the serosa, the other adherent to the vessels. Each sample was exposed to mercaptoethanol, PBS, 10 mM MEDTA, 1 mM PMSI, 0.5% 2-mercaptoethanol and digested overnight. The sample was then dialyzed against water for 72 hours. The retentate had 40-80 µg/ml protein. Harvest procedure was adapted from Guerardel et al. (Biochem J 352: 449-463. 2000).

Induction of Neural Cells from UCMS Cells

We utilized a procedure based on the method described by Woodbury et al. [2000] to induce UCMS cells to become neural cells. The UCMS cells were pre-induced by overnight treatment with basic fibroblast growth factor (10 ng/ml) DMEM and 20% fetal bovine serum. Neuronal differentiation was induced with 2% DMSO and 200 µM butylated hydroxyanisole in DMEM+2% fetal bovine serum. After 5 h, the media was modified for long-term induction by adding 25 mM KCl, 2 mM valproic acid, 10 µM forskolin, 1 µM hydrocortisone and 5 µg/ml insulin. By replacing this media every 36 hours we have maintained long-term cultures of the induced cells for longer than 1 month.

Immunocytochemistry

Immunocytochemistry was done by immunoperoxidase staining using standard methods. Briefly, cultured cells were grown on sterile glass cover slips in 24 well plates. Prior to immunodetection, they were washed briefly with PBS and the cells fixed by treating with methanol at −10° C. Slides were blocked with 10% normal blocking serum (derived from same species as the secondary antibody) in PBS for 20 min, washed with PBS, incubated with primary antibody in 1.5% normal blocking serum in PBS for 60 min (0.1 to 2.0 µg/mL depending on antibody). The slide was washed three times with PBS and incubated with an HRP-conjugated secondary for 15 min.

Preparation of UCMS Whole-Cell Lysates

These were made from UCMS cells by standard techniques using a lysis buffer (RIPA) consisting of PBS with 1% Nonidet P40, 0.5% sodium deoxycholate, 0.1% SDS and a protease inhibitor cocktail (1:500) (Sigma P8340). Lysis buffer was added to the culture dish with UCMS cells after washing with cold PBS 3 times. The culture dishes were then scraped and the lysate was aspirated into a syringe with a 21-gauge needle to shear DNA. The lysates were rocked in the cold for 1 h and centrifuged for 10 min at 10,000×g to remove insoluble material. Protein concentration was determined by the Micro BCA assay (Pierce). Typically protein concentrations of 1 µg/µL were obtained by this protocol.

Immunoblotting

Solubilized proteins (10 µg per lane) were separated by SDS-PAGE under reducing conditions and transferred to nitrocellulose membranes by electrophoretic transfer in a tank system with plate electrodes. The membranes were blocked for 1 h at room temperature with 5% nonfat milk in Tris-buffered saline (TBS: 100 mM Tris, 0.9% NaCl, pH 7.5) containing 0.1% Tween 20. Membranes were incubated with primary antibody for 1 h at room temperature followed by 3 washes with 0.1% Tween/TBS.

Membranes were incubated for 1 h at room temperature with the appropriate horseradish peroxidase conjugated secondary antibody diluted in 0.1% Tween/TBS. After four additional washes, with 0.1% Tween/TBS, the blots were visualized by chemiluminescence and recorded on radiographic film.

2D-Electrophoresis

Protein (40 μg) from total cell lysates was precipitated by ice cold acetone and resuspended in 25 μL of sample buffer containing 62.5 mM Tris HCl pH 6.8, 2.3% SDS, 5% β-mercaptoethanol, 10% glycerol and 0.01% bromophenol blue. Samples were loaded into capillary tube gels with an ampholyte range from pH 3 to 10 and were electrophoresed at 500V for 10 min and 750V for 3.5 h in a Mini Protean 2D Cell (BioRad). The second dimension separation was done using standard SDS-PAGE with an 8 to 16% gradient gel.

Results

UCMS cells were expanded as primary cultures. Initially they resembled flattened UCMS cells but with time round cells were observed growing on top of the UCMS cells. The round cells adhered to one another to form compact colonies. Within one hour after exposure to the induction media, multiple "neurites" were seen extending from many cells and the cell bodies became rounded and refractile. By four to five hours, some cells resembled bipolar or multipolar neurons and extended long processes that contracted similar processes from other neuron-like cells to form primitive networks. Growth cone-like swellings were seen at the ends of some of the processes. Cultured UCMS cells synthesized the catecholaminergic neuron marker, tyrosine hydroxylase.

After treatment with bFGF overnight and serum free media plus butylated hydroxyanisole and dimethylsulfoxide they assumed the morphology of neural stem cells e.g. a rounded cell body with multiple neurite-like extensions. Eventually some cells resembled bipolar or multi-polar neurons, and processes contacted each other to form networks. Expression of neuronal and glial cell specific proteins was produced in untreated UCMS cells. Both Western blotting and immunocytochemistry were used to determine the bFGF-treated neural stem-like cells and the more differentiated compact colonies.

Neuron specific enolase was detected in UCMS cells, the neural stem-like bFGF treated cells and in the more differentiated compact colonies at equal levels. TUJ1, an early neuron specific protein, was expressed in both the treated and bFGF-treated UCMS cells but not in the more differentiated colonies. Expression of TUJ1 was increased in the neural stem-like cells compared to the untreated UCMS cells. Likewise, glial fibrillary acidic protein (GFAP), an astroglial cell specific protein, expression was increased by treatment of UCMS cells with bFGF. Induced UCMS cells stained for neuron-specific enolase (NSE).

Conclusion

Following the described procedure UCMS cells easily differentiated into neurons. The differentiated UCMS cells were characterized using immunocytochemistry and Western blotting.

Untreated UCMS cells, in many cases exhibited positive staining for neural proteins. The study has produced cultures of UCMS cells that include cKit positive cells and myofibroblasts that express smooth muscle actin. The UCMS cells have telomerase activity and can be maintained in culture for extensive periods. The UCMS cells are capable of differentiating along a neural program spontaneously. Induction speeds up this process and increases the number of UCMS cells that follow the neural program. After induction UCMS cells develop a neuron-like morphology with neurite-like processes and networks between cells. UCMS cells express protein markers for neural stem cells, mature neurons, astrocytes and oligodendrocytes. Expressed neuronal markers included neurofilament (NF-M, 14 kD) and tau, a protein expressed in mature neurons.

The results show that UCMS cells provide a novel source of neural stem cells.

Example 2

UCMS Cells Propagate Vigorously

We have successfully propagated bovine, porcine, human, rat, and canine UCMS cells. UCMS cells have been maintained beyond 100 cell doublings and show no signs of decreased vigor.

The cells are derived from Wharton's Jelly matrix rather than cord blood because umbilical vessels are stripped from the cord before explant preparation and the cells are negative for markers of the hematopoietic lineage such as CD34 and CD45.

The UCMS cells have been subjected to harsh environmental conditions such as prolonged exposure to room temperature, prolonged periods without media replacement and culturing in serum-free media. In the latter case they all become spherical and thrive and divide as suspension cultures.

Example 3

Characteristics of Undifferentiated Wharton's Jelly Cells

Materials and Methods

The TRAPeze® XL Telomerase Detection Kit (Intergen) was used according to manufacturer's instructions to measure the telomerase enzyme activity of porcine and human Wharton's Jelly cells. The TRAPeze® XL Telomerase Detection Kit uses a modified TRAP (Telomerase Repeat Amplification Protocol) assay to detect telomerase activity through the amplification of telomeric repeats using fluorescence energy transfer primers (Amplifluor™) that produce measurable fluorescence only when incorporated into TRAP products.

Porcine and human Wharton's Jelly cells that were grown in culture for 45 passages, were washed twice with PBS, and then frozen at −80° C. for 30 minutes. The cells were resuspended in 100 μl of CHAPS XL Lysis Buffer (included in the telomerase detection kit) and with 20 U of ribonuclease inhibitor (Promega). This suspension was incubated on ice for 30 minutes. The extract was pelleted (12,000 g at 4° C.) and the supernatant frozen at (−80° C.) until assayed for telomerase. Human carcinoma cells (included in the telomerase detection kit) were used as a positive control. For telomerase quantification, 50 μl reactions were prepared containing 10 μl of the 5×TRAPeze XL® Reaction Mix, 2 Units of Taq Polymerase (Promega), 38 μl of sterile PCR water, and 2 μl of the sample cell extract. This mixture was then incubated at 30° C. for 30 minutes to allow for the telomerase enzyme to synthesize telomeric repeats. PCR amplification of the telomeric repeats was performed on a Touchgene gradient thermocycler (Techne) using a three-step PCR at 94° C./30 seconds, 59° C./30 seconds, 72° C./1 minute for 35 cycles followed by a 55° C./25 minute extension step. Following a five minute incubation at 5° C., the fluorescence of each reaction was measured with a Fluoroskan Ascent FL fluorescent plate reader (Labsystems). The telomerase activity of each sample was determined by calculating the ratio of the increase in fluorescein absorbance (produced by the amplification of telomeric repeats) divided by the increase in sulforhodamine absorbance.

An aliquot of each sample was heated to 85° C. for 20 min to inactivate the telomerase enzyme, and serve as a negative control. To assure that the measured telomerase activity was not affected by the presence of PCR inhibitors, a sample of 500 porcine Wharton's Jelly cells was "spiked" with 50 positive control cells.

Results

Wharton's Jelly cells were successfully isolated from porcine and human umbilical cord explants and expanded as primary cultures. The morphology of the heterogeneous population of Wharton's Jelly cells isolated from explants includes mesenchymal-like cells with a fusiform or stellate appearance and individual round cells (FIG. 1A). As Wharton's Jelly cells reach confluency, colonies of round cells begin to form; these round cells resemble neurospheres.

Cell Markers

Figure 2:
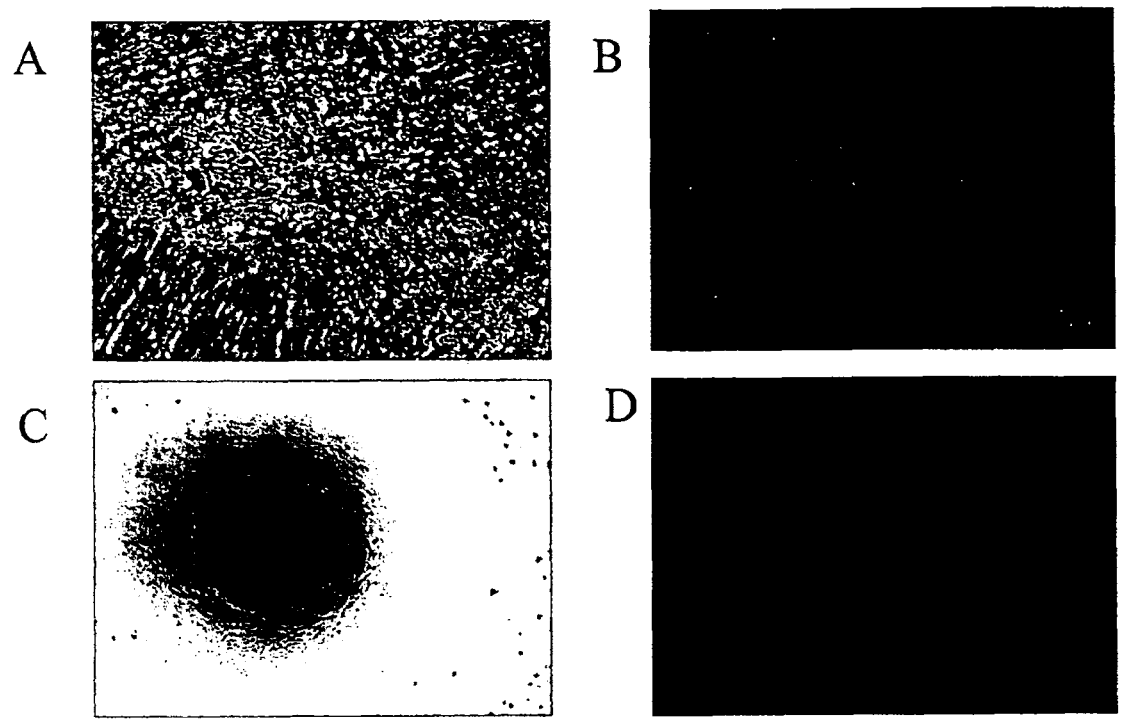
FIGS. 2A through 2D illustrate that Wharton's Jelly cells are positive for cKit, the stem cell factor receptor. Untreated Wharton's Jelly cells grown on laminin/PDL coated culture plates were fixed in cold methanol and probed with rabbit polyclonal cKit, followed by incubation with FITC labeled donkey anti-rabbit secondary antibody. Wharton's Jelly cells with newly forming colonies (A) bright field and (B) fluorescence. Colonies formed by untreated Wharton's Jelly cells (C) bright field and (D) fluorescence.
Figure 3:
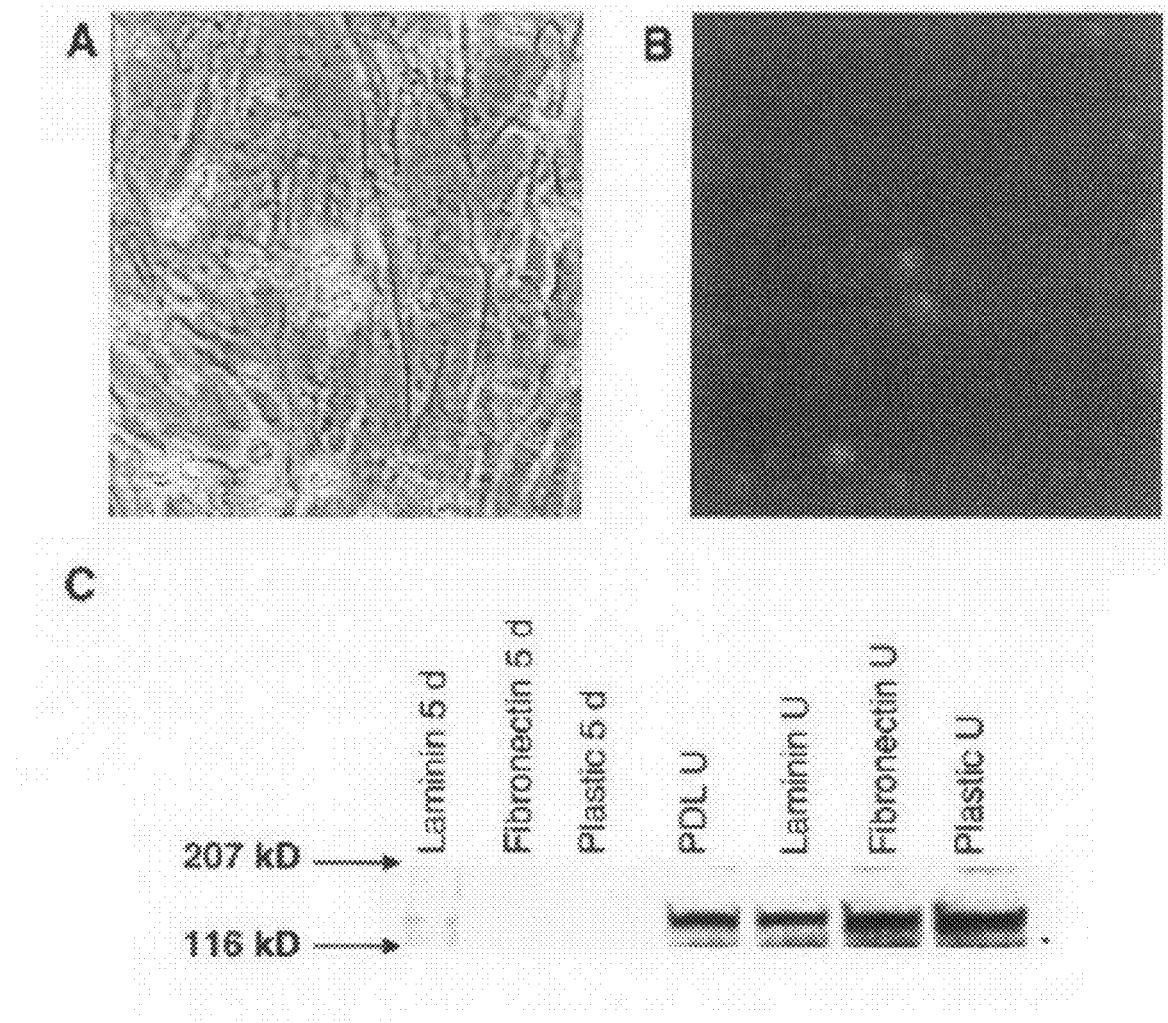
FIGS. 3A through 3C illustrate that cKit positive cells persist in porcine Wharton's Jelly cells after induction. Micrographs 10 d after neural induction and grown on poly-D-lysine/laminin coated plates bright field (A) and anti-cKit immunofluorescence (B), respectively. C) Western blot showing cKit immunoreactive bands (145 kD) in cell lysates 5 d post-induction and plated on PDL/laminin.

Wharton's Jelly cells were examined for expression of cell markers of post-natal mesenchymal stem cells. cKit is a stem cell factor receptor expressed in bone marrow stromal cells and hematopoetic stem cells. cKit expression was very high in Wharton's Jelly colony-forming cells (FIG. 2) and in individual round undifferentiated cells that were plated on matrix coated plate with a combination of poly-D-lysine (PDL) and laminin or laminin alone even after neural induction (FIG. 3). The expression of cKit by Wharton's Jelly cells was greatly diminished after induction into neural cells and expression was detected only in cells plated on laminin (FIG. 3C). Cultures include colonies and individual cells that were positive for alkaline phosphatase and OCT4.

Figure 4:
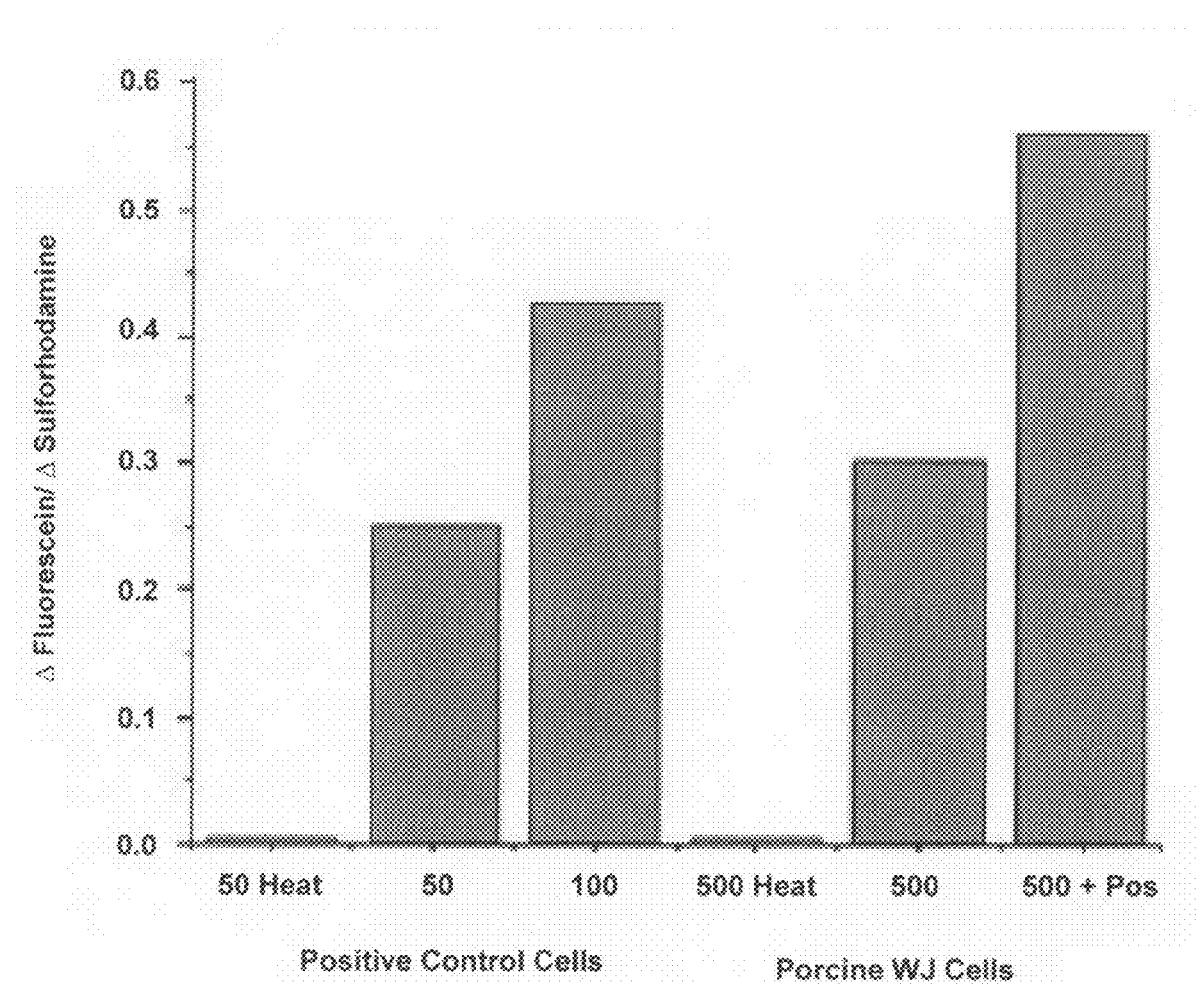
FIG. 4 illustrates telomerase activity of porcine Wharton's Jelly cells. Telomerase activity (Fluorescein/Sulforhodamine) from left to right: 50 positive control cells heat treated to inactivate the telomerase enzyme, 50 positive control cells, 100 positive control cells, 500 Wharton's Jelly cells heat-treated to inactivate the telomerase enzyme, 500 Wharton's Jelly cells, 31 and 500 Wharton's Jelly cells "spiked" with 50 positive control cells indicating the absence of PCR inhibitors in the 500 cell sample.

Porcine Wharton's Jelly cells have been maintained in culture for more than 100 population doublings with no decrease in proliferative capacity. Telomerase activity is found in embryonic stem cells and may contribute to their proliferative capacity by maintaining telomere length. Wharton's Jelly cells were assayed for telomerase activity using a fluorescence-based modified TRAP assay. Wharton's Jelly cells expressed telomerase activity that is about 10% of that expressed by a positive control carcinoma cell line (FIG. 4). The telomerase activity was inactivated by heating as expected. Minimal if any PCR inhibition was detected as indicated by the increase in telomerase activity measured in the sample that included Wharton's Jelly cells and positive control cells. The sum of telomerase activities measured for the two separately was approximately the same as the combined sample.

Figure 5:
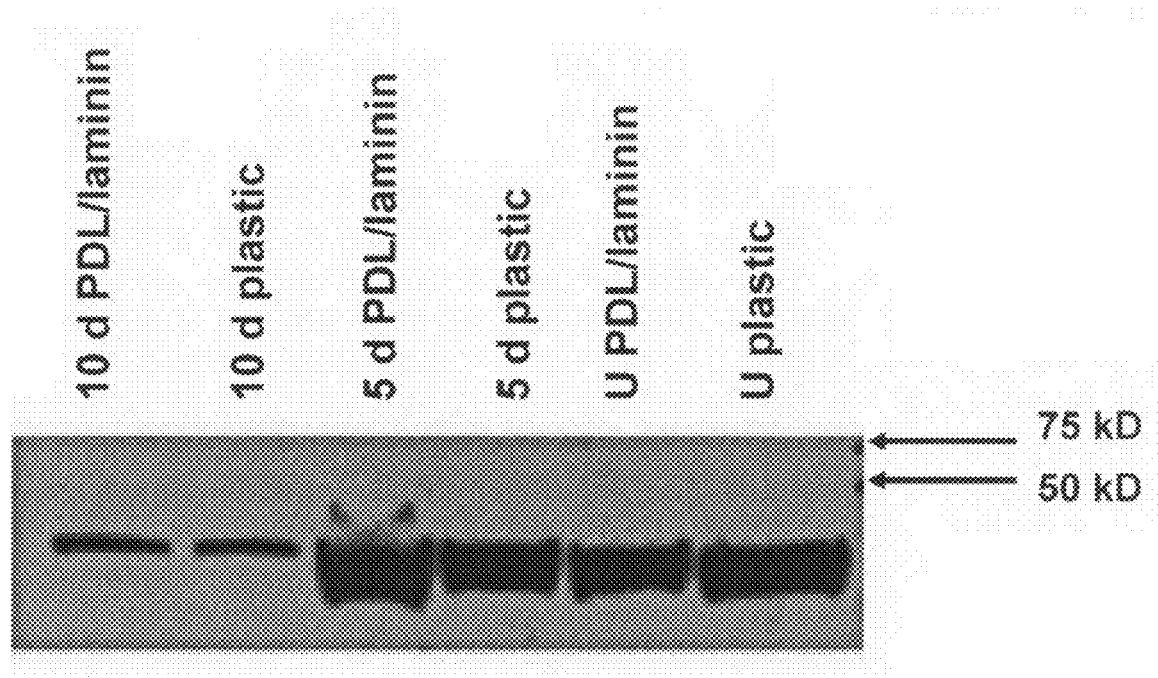
FIG. 5 illustrates smooth muscle actin, a marker for myofibroblasts, is expressed by Wharton's Jelly cells. Whole cell lysates of Wharton's Jelly cells grown on plastic or PDL/Laminin which were either left untreated (U) or treated to induce neural differentiation for 5 and 10 d were resolved by SDS-PAGE on 8-16% gradient gels and transferred to nitrocellulose. The blots were probed for the presence of smooth muscle actin. Smooth muscle actin expression is greatly decreased by 10 post-induction.

Wharton's Jelly was previously shown to be composed of smooth muscle actin-positive myofibroblast-like stromal cells. To determine if Wharton's Jelly cells, after being propagated in culture, maintained the phenotype for Wharton's Jelly stromal cells, we measured smooth muscle actin expression by immunoblotting (FIG. 5). Smooth muscle actin was expressed at similar levels in Wharton's Jelly cells grown on PDL/Laminin matrix and in Wharton's Jelly cells grown on plastic. Thus, Wharton's Jelly cells that were maintained in culture for extensive doublings continued to express this myofibroblast marker. Growth on matrix did not appear to select for a different population of cells. However, smooth muscle actin expression was greatly decreased by 10 days after neural induction. This suggests that the phenotype of the majority of the induced Wharton's Jelly cells changed to neural phenotypes.

Example 4

UCMS Cells Form Spherical Aggregates

In the Central Nervous System (CNS), two stem cell populations have been identified: ependymal cells and subventricular zone astrocytes. In culture, neural stem cells form clonal cell aggregates called "neurospheres" and embryonic stem cells form spherical embryoid bodies. UCMS cells have also been shown to form spherical aggregates in culture.

When UCMS cells initially grow outward from explants two populations of cells are present—spherical or flat, stellate cells. When the cells become confluent, they form white, spherical colonies or embyoid bodies that remain attached to cells below. The colonies look like 'neurospheres'. Cells can be seen migrating out of the colonies, and the colonies grow in size over time. Occasionally they expand into a tube-like structure.

The cells within the colonies are very tightly adhered to one another. They can be mechanically dissociated with difficulty after prolonged trypsinization. When they are subsequently re-plated, the rounded cells grow rapidly to form new confluent monolayers and new colonies. The colonies have been sectioned and stained with hematoxylin and eosin. The colonies are noted to be heterogeneous with polyhedral cells, fusiform cells and small dark cells present. Elongated eosinophilic structures reminiscent of bone spicules are present.

Example 5

UCMS Cells Differentiate into a Neural Phenotype

Wharton's Jelly, the matrix of umbilical cord, provides an easily attainable source of primitive stem cells. These exciting findings show that cells from the matrix of umbilical cord have properties of stem cells and present a rich source of primitive cells. This study showed their capacity to differentiate into a neural phenotype in vitro.

Materials and Methods

Initiation of Wharton's Jelly Matrix Cell Cultures

Umbilical cords were aseptically collected from porcine reproductive tracts collected from a commercial abattoir at gestational day 45-60. Human umbilical cords were obtained from a local obstetrician from full-term births. Umbilical arteries and vein were removed and the remaining tissue was transferred to a sterile container in Dulbecco's Modified Essential Media (DMEM) (Invitrogen Life Sciences) with antibiotics (penicillin 100 µg/mL, streptomycin 10 µg/mL and amphotericin B 250 µg/mL, Invitrogen Life Sciences), or defined media, DMEM, 40% MCDB201, 1× insulin-transferrin-selenium, 1× linoleic acid-BSA, 10-8 M dexamethasone, 10-4 M ascorbic acid 2-phosphate, 100 U penicillin, 1000 U streptomycin, 2% FBS, 10 ng/mL EGF, 10 ng/mL PDGF-BB, and was diced into small fragments. The explants were transferred to 6 well plates containing the medium along with 20% fetal bovine serum (Invitrogen Life Sciences). They were left undisturbed for 5-7 days to allow migration of cells from the explants, at which point the media was replaced. They were re-fed and passaged as necessary.

Induction of Neural Cells from Wharton's Jelly Matrix Cells

Wharton's Jelly cells were induced to become neural stem cells and neuronal cells. Briefly, Wharton's Jelly cells were pre-induced by overnight treatment with basic fibroblast growth factor (bFGF) (10 ng/ml) in medium and 20% fetal bovine serum. Neuronal differentiation was induced with 2% DMSO and 200 µM butylated hydroxyanisole in DMEM+2% fetal bovine serum. After 5 hours, the media was modified for long-term induction by adding 25 mM KCl, 2 mM valproic acid, 10 µM forskolin, 1 µM hydrocortisone and 5 µg/ml insulin. Matrix coated plates and tissue culture slides were obtained from BD Biosciences.

Immunocytochemistry

Immunocytochemistry was done by ABC immunoperoxidase using a commercial kit (VectaStain) or immunofluorescence staining. For immunofluorescence, cells were washed with phosphate buffered saline (PBS) and fixed by treating with methanol at −10° C. This was followed by washing with three changes of PBS and air drying. Slides were blocked with 10% normal blocking serum (derived from same species as the secondary antibody) in PBS for 20 min, washed with PBS, incubated with primary antibody in 1.5% normal blocking serum in PBS for 60 min (0.1 to 2.0 μg/mL). The slide was then washed 3 times with PBS and incubated with FITC-conjugated secondary antibody (Santa Cruz Biotechnology) for 15 min. Resulting immunoreactive cells were visualized by fluorescence microscopy. For immunoperoxidase, cells were fixed by treating with 10% BNF overnight. Slides were blocked with 5% normal blocking serum (derived from same species as the secondary antibody) in PBS for 30 min followed by incubation with primary antibody for 60 min. The slide was incubated with horse radish peroxidase linked secondary antibody and developed according to kit instructions.

Preparation of Whole-Cell Lysates

Whole cell lysates were made from Wharton's Jelly cells by standard techniques using a lysis buffer consisting of PBS with 1% Nonidet P40, 0.5% sodium deoxycholate, 0.1% SDS and a protease inhibitor cocktail (1:500) (Sigma P8340). Lysis buffer was added to the culture dish with Wharton's Jelly cells after washing with ice cold PBS 3 times. The culture dishes were scraped and the lysate was aspirated into a syringe with a 21-gauge needle to shear DNA. The lysates were rocked at 4° C. for 1 h and centrifuged for 10 min at 10,000×g to remove insoluble material. Protein concentrations were determined by the Micro BCA assay (Pierce). Typically, a protein concentration of 1 μg/μL was obtained by this protocol.

Immunoblotting

Solubilized proteins were separated by SDS-PAGE on 8-16% continuous gradient gels under reducing conditions and transferred to nitrocellulose membranes by electrophoretic transfer in a tank system with plate electrodes. The membranes were blocked for 1 h at room temperature with 5% nonfat milk in Tris-buffered saline (TBS: 100 mM Tris, 0.9% NaCl, pH 7.5) containing 0.1% Tween 20. Membranes were incubated with primary antibody for 1 h at room temperature followed by 3 washes with 0.1% Tween/TBS. Membranes were incubated for 1 h at room temperature with the appropriate horseradish peroxidase conjugated secondary antibody (Pierce) diluted in 0.1% Tween/TBS at (1:50,000). After four additional washes, with 0.1% Tween/TBS, the blots were visualized by chemiluminescence (Super Signal, Pierce) and recorded on radiographic film.

Antibodies

Antibodies were used at the following dilutions for immunoblotting and immunocytochemistry, respectively: neuron specific enolase (NSE) (1:2000, 1:500, Chemicon); neurofilament M (NFM) (immunocytochemistry only 1:500, Chemicon); TUJ1 (1:2000, 1:1000, Covance); glial fibrillary acidic protein (GFAP) (1:2000, 1:500, Chemicon); 2',3'-cyclic nucleotide-3'-phosphodiesterase (CNPase) (1:2000, immunoblot only, Chemicon); smooth muscle actin (1:2000, immunoblot only, Research Diagnostics); cKit (1:2000, 1:200, Research Diagnostics); Tyrosine hydroxylase (TH) (1:1000, immunoblot only; East Acres Biologicals); growth cone associated protein (GAP-43) (1:2000, 1:200, Santa Cruz Biotechnology).

Results

Wharton's Jelly Cells Differentiate into Neural Cells

Wharton's Jelly cells were grown to near confluency and treated with bFGF overnight and low serum media plus butylated hydroxyanisole and dimethylsulfoxide, which is a known neural-inducing protocol. This treatment caused Wharton's Jelly cells to undergo profound changes in morphology (FIG. 1B, C) with some cells developing multiple neurites extending from the cell body. Single long axon-like processes develop (FIG. 1B) and granular structures resembling Nisil substance were also observed in many of the Wharton's Jelly cells (FIG. 1C).

Expression of Neural Stem Cell Markers

To determine if the Wharton's Jelly cells expressed a marker for neural stem cells, neuron specific enolase (NSE), immunocytochemistry was done within an hour after treatment with the inducing agents BHA and DMSO. The induced Wharton's Jelly cells showed positive immunostaining for NSE at this time point, were round and blast-like in appearance, and had a few neurites beginning to form (FIG. 6A). Immunoblots of whole cell lysates were done to assess whether NSE was expressed in untreated Wharton's Jelly cells or in the neurosphere-like colonies. NSE was expressed in both untreated Wharton's Jelly cells and in colonies (FIG. 6B). However, there is slightly less NSE expression in Wharton's Jelly cells 5 hours post-induction (FIG. 6B).

Expression of Mature Neuronal Proteins

Expression of mature neuronal markers was determined to assess the extent of differentiation of the Wharton's Jelly cells after induction. Neurofilament M (NFM), a neuron-specific intermediate filament was expressed at one (FIG. 7A) and three (FIG. 7B) days post-induction. Note the long processes revealed by NFM immunostaining and the formation of networks that increased in complexity from day 1 to day 3 post-induction.

TUJ1, a class III neuron-specific β-tubulin, is another marker for neuronal differentiation. The immunoblot in FIG. 8A shows that increasing levels of TUJ1 were expressed during the course of differentiation from between day 1 and day 10 post-induction. Interestingly, a low level of TUJ1 was expressed in Wharton's Jelly cells treated only with bFGF overnight. Fully induced Wharton's Jelly cells showed positive immunostaining for TUJ1 primarily in the soma and proximal part of the axon-like structure (FIG. 8B).

To determine whether the Wharton's Jelly cells could become fully differentiated into a specific neuronal phenotype, expression of TH was measured. TH is a marker for catecholaminergic neurons. The results are shown in FIG. 8C. Immunoblot analysis shows that TH was expressed in neurosphere-like colonies and in fully induced Wharton's Jelly cells but not in untreated cells.

GAP-43, a neuron-specific microtubule-associated protein that localizes to axons, was also expressed in Wharton's Jelly cells after they differentiate (FIG. 9). The long processes of the induced Wharton's Jelly cells showed positive staining for GAP-43. Immunoblot analysis confirmed expression of GAP-43 10 days post-induction on either plastic or PDL/Laminin but not in untreated Wharton's Jelly cells (FIG. 9C), although the level of expression was higher in the cells grown on PDL/laminin.

Expression of Glial Markers

To determine whether Wharton's Jelly cells differentiate into glial cells, expression of GFAP and CNPase, astrocyte and oligodendrocyte markers, respectively, was determined (FIG. 10). GFAP-positive cells were identified in Wharton's Jelly cultures after full induction. The morphology of the GFAP positive cells was stellate and lacked the long processes of the cells that are positive for neuronal markers (FIG. 10A). GFAP expression was observed in untreated Wharton's Jelly cells but was expressed at slightly higher levels after induction (FIG. 10B). In contrast, expression of CNPase, a marker for oligodendrocytes, was nearly identical in untreated, bFGF-treated and fully induced Wharton's Jelly cells (FIG. 10C).

Human Wharton's Jelly Cells Differentiate into Neurons

Figure 11:
FIG. 11 illustrates that human Wharton's Jelly cells differentiate into neurons. Left) Hoffman micrograph of untreated Wharton's Jelly cells from passage 11 grown on plastic showing both round and flattened stellate cells (100× magnification). Center and Right) Human Wharton's Jelly cells after treatment with the induction protocol and culture in long-term induction media for 1.5 days have a neuron-like morphology (Center) with long process (100× magnification) and (Right) multiple neurites (200×).

Cultures from human umbilical cord matrix were established (FIG. 11). Initial studies to determine whether there were different populations of cells that arise from different regions of the umbilical cord indicate that the placental end can be a richer source of cells. At least some human Wharton's Jelly cells were positive for smooth muscle actin (data not shown). The cells were alkaline phosphatase positive.

Human Wharton's Jelly cells were induced to form neurons. FIG. 11 shows the changes observed in morphology of human Wharton's Jelly cells after treatment with bFGF, BHA and DMSO and after long-term induction media treatment for 1.5 days.

Figure 12:
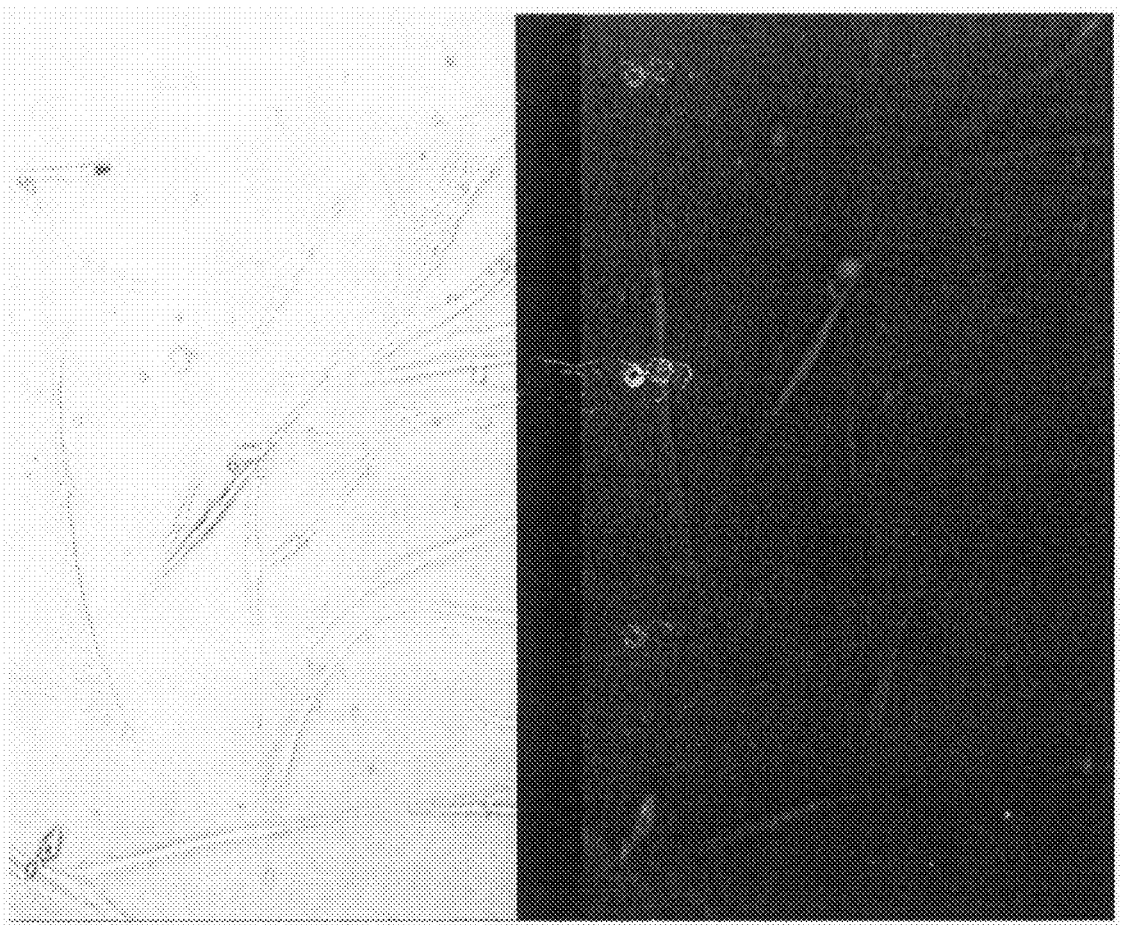
FIG. 12 illustrates that TUJ1 was expressed in induced clonal lines of human Wharton's Jelly cells.
Figure 13:
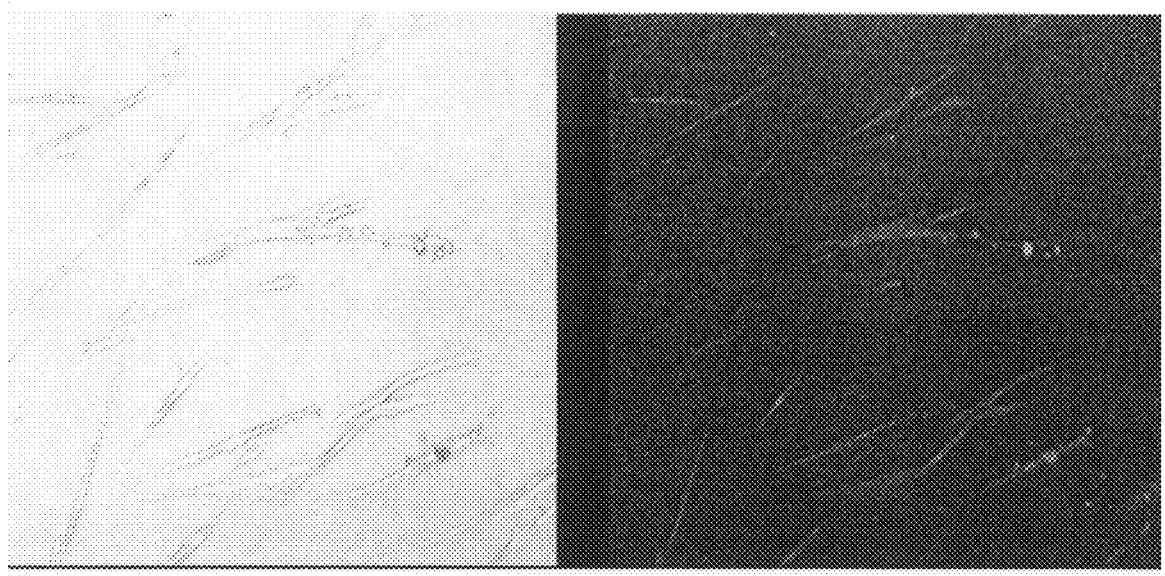
FIG. 13 illustrates that NFM was expressed in induced clonal lines of human Wharton's Jelly cells.
Figure 14:
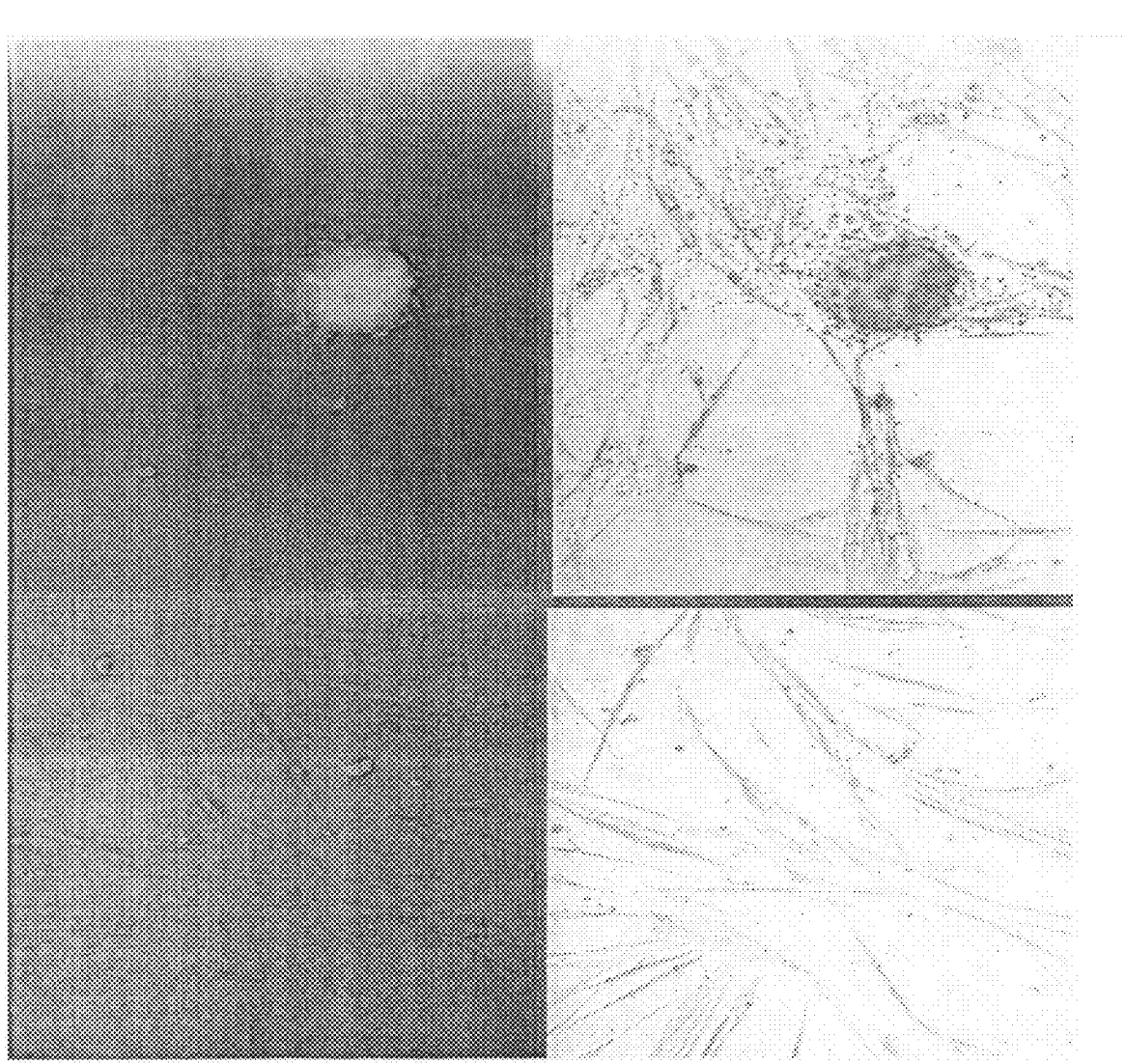
FIG. 14 illustrates that PSD-95 was expressed in induced clonal lines of human Wharton's Jelly cells.

Immunocytochemical analysis shows that induced human Wharton's Jelly cells were positive for TUJ1 (FIG. 12) and NFM (FIG. 13). Nearly 100% of the fully induced cells were positive for TUJ1 and NFM by immunocytochemistry. The induced cells also expressed post-synaptic density protein (PSD-95), a scaffolding protein at the synapse (FIG. 14).

Figure 15:
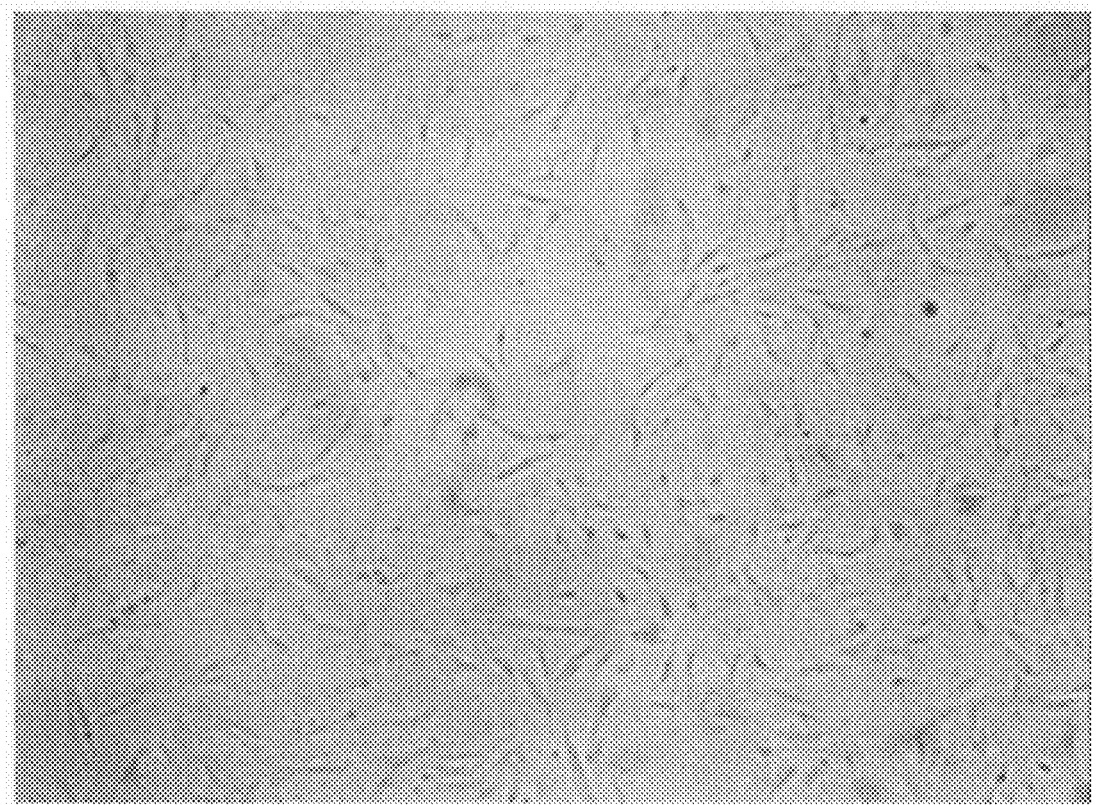
FIG. 15 illustrates un-induced cells in culture.

FIGS. 15A through 15C illustrate additional characteristics of human umbilical cord matrix in culture. FIGS. 15A and 15B illustrate cells that have been induced to differentiate into neurons. These cells exhibited a phase bright cell body, high nuclear to cytoplasmic ratio, and long varicose processes. FIG. 15C illustrates un-induced cells in culture. As these cells became confluent, the cells formed clusters that resembled neurospheres (dotted circles). The culture was sustained either by passaging clusters or adherent cells without apparent differences.

The induced human Wharton's Jelly cells were maintained in culture for up to 30 days by plating on fibronectin and adding NGF to the long term induction media.

Discussion And Conclusions

We have isolated cells from Wharton's Jelly, the gelatinous connective tissue from the umbilical cord. Wharton's Jelly cells have been cultured for more than 100 population doublings with no indications of senescence, changes in morphology, changes in growth rate, or changes in the ability of the cells to differentiate into neurons. Thus, Wharton's Jelly cells possess one of the defining characteristics of stem cells, the ability to self renew.

Wharton's Jelly cells share characteristics with other types of stem cells. Importantly, Wharton's Jelly cells have telomerase activity, which is found in human embryonic stem cells. In addition, certain Wharton's Jelly cells cultured from umbilical cord explants express the cKit receptor. In this study, we showed that Wharton's Jelly cells undergo changes in morphology and express neural specific proteins when induced. Therefore, cells from the gelatinous connective tissue of umbilical cord matrix can be an easily attainable source of stem cells that can be expanded in vitro, maintained in culture and induced to differentiate into neural cells.

We found that NSE, a marker for neural stem cells, was expressed at nearly equal levels in treated and untreated Wharton's Jelly cells. This result was surprising. The glial cell markers, GFAP and CNPase, were expressed at equivalent levels in treated and untreated Wharton's Jelly cells. These results indicate that UCMS cells express a number of neural proteins spontaneously and are primed to differentiate along a neural program.

Colonies of Wharton's Jelly cells also express NSE, cKit and even more intriguing, TH, a marker for catecholaminergic neurons. This indicates that the colonies that arise spontaneously after Wharton's Jelly cells grow past confluency can be neurosphere-like masses of cells.

In summary, these studies demonstrate that cells from Wharton's Jelly are a rich source of primitive cells that can be readily expanded in culture and that can be induced to form neurons and glia.

Example 6

Clones from Wharton's Jelly Cells

Cells from human, rat, and porcine umbilical cords have been isolated and cloned using limiting dilution methods. Certain of the clones are very fast growing. The fast growing cells exhibit round, small, blast-like morphology.

Example 7

Electrophysiology of Cells from Wharton's Jelly Cells

Figure 16:
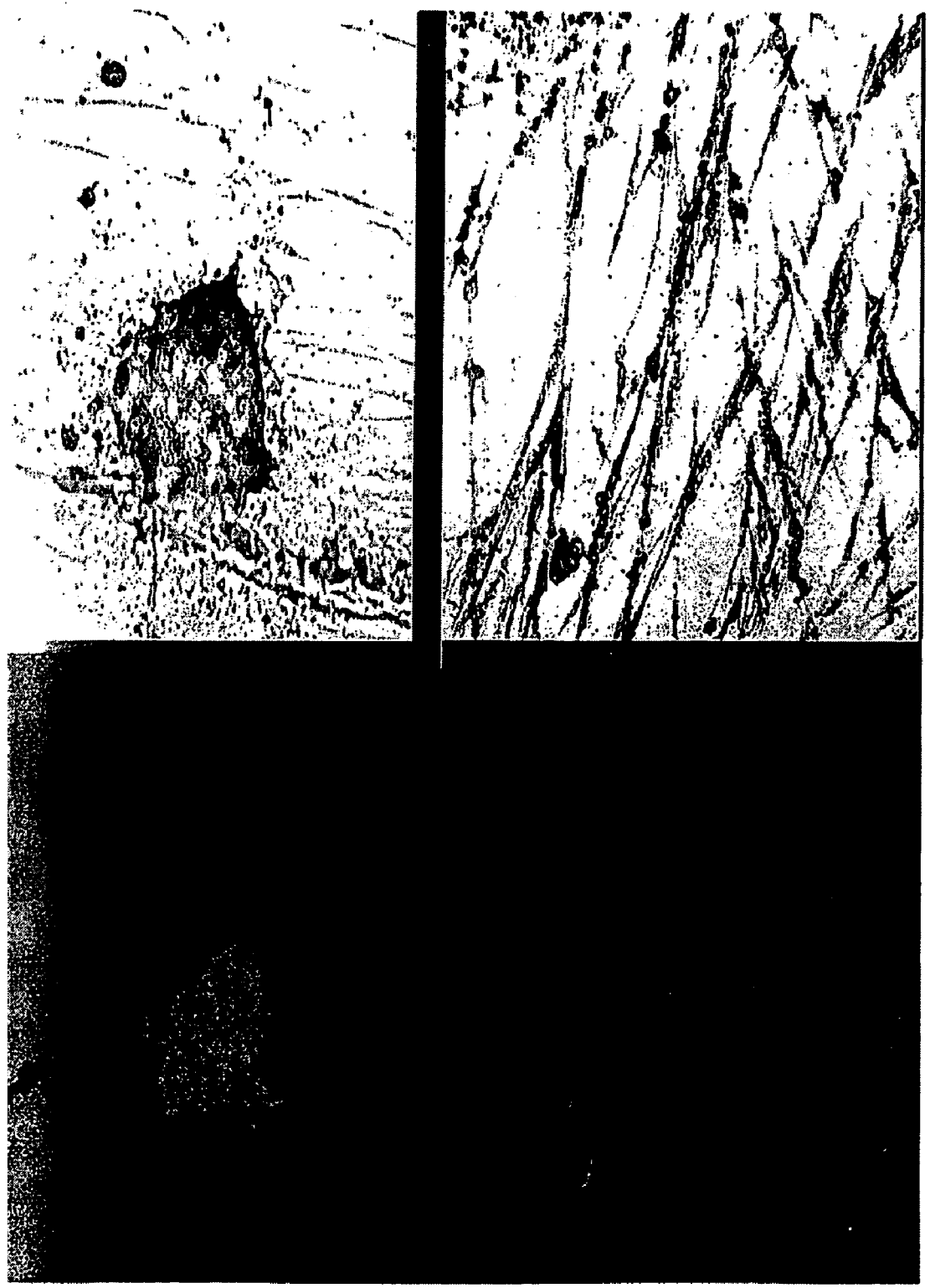
FIG. 16 illustrates that Kv1.4 was expressed in induced clonal lines of human Wharton's Jelly cells.

Upon induction, Wharton's Jelly cells have been demonstrated to have characteristics of neurons. These characteristics have been demonstrated to include rapidly activating, slowly inactivating voltage-gated current. The whole cell current from the induced Wharton's Jelly cells resembled that of early neurons. These cells exhibited characteristics of Kv1.1 ion channels. They were blocked approximately 50% at +60 mV by 4-aminopyridine. Immunoblotting also showed Kv channels in the induced cells (FIG. 16).

Example 8

UCMS Cells can be Implanted

Materials and Methods

Stem Cell Culture

Figure 17:
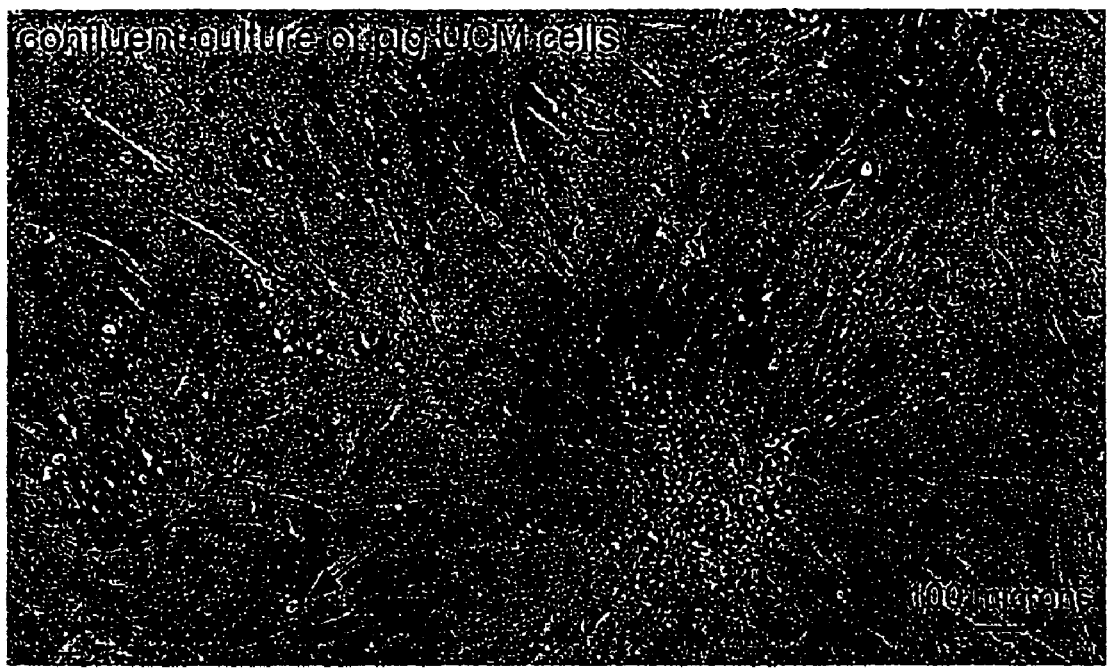
FIG. 17 illustrates a phase contrast micrograph of uninduced UCMS cells in culture. Two cell types are obvious: flat, fibroblast-like layer that adhered to the substrate with scattered small round cells (arrows). When the cells became confluent, rounded clusters of cells that float above the substrate started appearing (dotted circle). The culture was sustained by passaging either the clusters or the adherent cells without apparent differences.

Pig umbilical cords were aseptically collected from pre-term fetuses (approximately 60 day) at slaughter. Umbilical arteries and vein were stripped manually and discarded. The remaining tissue was minced finely in a sterile container in DMEM media with an antibiotic (Gentamycin, 20 µg/ml, Gibco BRL) and an antifungal agent (Amphotericin B 250 µg/µl, Sigma). The explants were transferred to 6 well plates containing the above media along with 20% fetal bovine serum (FBS) for culture. The primary cultures were left undisturbed for about 7 days to allow migration of cells from the explants, then re-fed. They were fed thereafter twice weekly and passaged as necessary (cells passaged at 80-90% confluency). These stem cell cultures have been maintained beyond 100 population doublings and continue to grow vigorously (FIG. 17).

Enhanced Green Fluorescent Protein (eGFP)-Expressing UCMS Cells

The UCMS cells were modified to incorporate the Sleeping Beauty Transposon system. The transposon system was modified as follows: The plasmid containing the transposon pT/HygR-eGFP was used as the template to generate a PCR product of the hygromycin resistance-eGFP insert. The neomycin resistance gene from the original transposon vector (pT/SVNeo) was removed using the blunt cutters Bsa BI and Nac I, and the hygromycin R/eGFP PCR product was ligated into the original vector. This plasmid along with the pCMV-SB plasmid containing the transposase gene driven by the CMV promoter using lipofection (Lipofectamine, BRL) were cotransfected. Hygromycin was added to the medium after three days at 200 or 250 µg/ml to select for transfected cells and stable transfection was attained after three weeks in selection media. The eGFP-expressing UCMS cells were maintained in hygromycin containing medium for 2-3 passages prior to transplantation.

Transplantation Procedure

UCMS cells that had been in culture for 17, 40, 57, 58, or 60 passages were used for the transplantation experiments. There were no apparent differences in the results that could be attributed to using one passage or another. In some cases, the UCMS cells were labeled with the lipophilic dye PKH 26 red (Sigma, St. Louis, Mo.) prior to transplantation. PKH 26 is non-toxic and a permanent fluorescent marker. In preparation for transplanting, the preconfluent cells were lifted with trypsin (7-8 minutes). The trypsin was inactivated by the addition of an equal volume of DMEM and 20% fetal bovine serum. The cells from several plates were pooled and the number of cells was estimated by counting on a hemocytometer. The final concentration was adjusted to about 1000 cells per microliter.

The UCMS cells were transplanted into the periphery of anesthetized Lewis or Sprague-Dawley rats (2% halothane in oxygen) via tail vein injection (approx. $10^6$ cells in 0.5 ml flushed with 0.5 ml sterile saline) and intramuscular injection (approx. $10^6$ cells in 0.4 ml); or via intramuscular injection alone (approx. $10^6$ cells in 0.5 ml).

The UCMS cells were transplanted into anesthetized Lewis or Sprague-Dawley rats (2% halothane in oxygen) centrally via stereotaxic injection (approximately 10,000 cells in 10 microliter). For stereotaxic injection, a glass micropipette was lowered into the striatum (Bregma +0.5, Lateral 3.4; D-V 5.0) and a 1 µl bolus of graft cells delivered over 1 minute. After 1 minute interval, the micropipette was raised approximately 200 µm and a second 1 µl injection made. In this way, multiple injections were distributed along an injection tract until the entire 10 µl volume was delivered. In other cases, the animals had a guide cannula implanted in a previous surgical session prior to delivering the cells via an injection cannula (Plastics One).

Control transplants (sterile saline alone, Con rats) were performed in age-matched animals. In a separate control experiment, two rats were transplanted with PKH 26 loaded UCMS cells that had been previously lysed by sonic disruption in phosphate buffer saline (for approximately 1 minute). The disruption of the cells was confirmed by flow cytometry: The first round of sonic disruption resulted in 99.7% of the cells being broken into smaller fragments. To confirm that as many of the cells as possible were destroyed, the cell suspension was subjected to a second round of sonic disruption. After this second round of sonic disruption, about 99.8% of the cells were broken into smaller fragments. Finally, an aliquot of the disrupted cells was plated in growth media to confirm that no living cells remained. Control rats and normal animals with no-treatment served as specificity and background controls for immunocytochemistry.

Immunocytochemistry (IC)

Equithesin-anesthetized rats were sacrificed by transcardial perfusion with heparinized isotonic saline rinse followed by 10% buffered neutral formalin. The brains were removed, postfixed 2 hr, and cryoprotected in 20% sucrose. Frozen sections were cut at 30-40 µm coronally and sections were collected into three sets of adjacent sections, one set consisting of every third serial section. One set of sections was processed for immunocytochemistry and the adjacent sets were held in reserve in a cryoprotectant solution. Free floating tissue sections were immunocytochemically stained for GFP (Chemicon), pig-specific NF70 (Chemicon), TuJ1 (Covalence Research Products), NFM (Chemicon), and CNPase (Chemicon) and localized either with immunofluorescence or with peroxidase using a commercially available ABC kit (VectaStain). The monoclonal NF70 antibody was particularly valuable because it does not recognize rodent neurofilaments. When using this antibody, it was necessary to substitute previously adsorbed secondary antibody (adsorbed for rat antigens, Jackson Labs) for the secondary provided in the Vectastain kit.

The tissue was incubated in the following reagents: endogenous peroxidase elimination, 5% blocking serum, followed by the primary anti-serum, fluorophore-labeled (Jackson Immuno, fluorescein isothiocyanate or Molecular Probes, Alexafluor 480) or biotin-labeled (from the VectaStain kit) secondary antibody. The tissue was triple rinsed with PBS-0.2% Triton X-100 between each incubation.

For immunofluorescence detection, the tissue were mounted on gelatin-chromium potassium sulfate coated microscope slides and air dried. The stained sections were examined using epi-fluorescence microscopy after clearing and coverslipping with glycerol containing N-propyl gallate to prevent fading. For immunoperoxidase detection, the antigen was localized with diaminobenzidine (DAB, Sigma) and hydrogen peroxide. Immunocytochemical labeling was considered positive if: the signal was distinctly above background and the signal was above that seen in the negative controls (omission of primary antibody, or labeling found in Control or normal rats). To be considered double-labeled, the morphology and location of the cell must appear identical in both bright field (DAB) and fluorescence (PKH 26 or eGFP).

Results

Pig UCMS Cells in Culture

When UCMS cells initially grew outward from explants two morphologically distinct populations of cells were present: spherical or flat mesenchymal cells. When the cells become confluent, they form spherical colonies that remain attached to cells below (FIG. 17). These colonies resemble "neurospheres". UCMS cell culture can be maintained by either harvesting the neurosphere-like cell clusters or by passage of pre-confluent flat and spherical cells without apparent differences. The present UCMS cell cultures were maintained for more than 100 population doublings and they continue to grow vigorously.

Three cellular characteristics indicate that undifferentiated UCMS cells are a type of stem cell: 1. the number of passages that they have been maintained in culture, 2. these UCMS cells are telomerase-positive, and 3. these UCMS cells make the receptor for stem cell factor, c-kit. UCMS cells have been characterized in vitro by immunocytochemistry and Western blotting.

UCMS cells can be induced to differentiate into neurons and glia following a known procedure for differentiation of stem cells (FIGS. 18A through 18G). A small percentage of untreated UCMS cells and a larger percentage of differentiated UCMS cells exhibited positive staining for neural proteins. Within one hour of induction treatment, multiple "neurites" were seen extending from many cells, and the cell bodies became rounded and refractile in phase contrast. FIGS. 18A through 18G show how UCMS cells responded to induction using the established protocol and examples of differentiated UCMS cells that were immunocytochemically positive for TuJ1, tau and NFM.

Transplantation of Pig UCMS Cells into Rat Brain

The present example included transplantation of undifferentiated, preconfluent pig UCMS cells into adult rats. Two injection methods were used with differing results. In the animals injected with the Hamilton syringe, the graft cells were located along the injection tract and no gross brain damage was found four weeks after injection despite the large volume (4 µl). Many UCMS cells were found along the injection tract (FIGS. 19A through 19D). In contrast, the guide cannula animals had damage to the brain associated with the larger diameter guide cannula (data not shown). Apparently the brain tissue adjacent to the implanted cannula had withdrawn slightly because the transplanted cells were found distributed adjacent to the guide cannula tract, as well as at the tip.

Following recovery from surgery, no complications were observed. No animals died subsequent to transplantation and no unusual behaviors were noted. There was no sign of brain tumor or teratoma, immunological response, or glioma in transplant recipients; all animals increased bodyweight. Four weeks after transplantation, there was no apparent glial scar. Large injection volumes and guide cannula implantation caused obvious tissue damage, as one would expect. Multiple nuclei, indicative of fusion with host cells, were not observed in the transplanted cells and there was no evidence of uncontrolled replication of UCMS cells after transplantation.

After tissue processing, pig UCMS cells were identified either by the PKH 26 fluorescent staining of dye loaded cells or by pig-specific NF70 immunocytochemical staining (FIGS. 19A through 21B). PKH 26 fluorescent staining was found throughout the cytoplasm and membrane. NF70 immunocytochemical staining was spread throughout the cell cytoplasm (FIGS. 19A through 21B). No NF70 or PKH 26 staining was found in control animals. There was no evidence of immunological response in the 2-8 week period after grafting, i.e., there was no perivascular cuffing, no extracellular debris, no phagocytosis, etc. A subset of the UCMS cells had migrated into the parenchyma of the brain away from the injection site. At 2-4 weeks post-transplantation, most UCMS cells appeared as simple spherical cells 10-15 microns in diameter with a granulated cytoplasm. A small subset of the UCMS cells had single short processes extending from the cell body at this time. Post-transplantation, many UCMS cells were found along the injection tract (FIGS. 18A through 18G).

At six weeks, UCMS cells were also found ipsilateral to the transplantation site adjacent to the corpus callosum. Thus, a subset of UCMS cells had apparently migrated from the injection site into the parenchyma (data not shown).

At 2-6 weeks post transplantation, a subset of the PKH 26-labeled UCMS cells were immunocytochemically stained for neural markers such as TuJ1 and MAP2 (FIGS. 20A through 20D). Positive staining for CNPase in some PKH 26 cells was also detected, suggesting that some of the UCMS cells may differentiate into oligodendrocytes (data not shown). It was interesting to note that TuJ1, CNPase and MAP2 staining was found in PKH 26-negative cells that may not be part of the grafted material (indicated by asterisks in FIGS. 20A through 20D).

Transplantation of eGFP-Expressing UCMS Cells into the Brain

At 4 weeks post-transplantation, eGFP expressing UCMS cells were detected in the brain spread along the cannula tract. The cytoplasm of these cells had a granular appearance and a large percentage of the cell stain positively for NF70 (FIGS. 20A through 20D). The graft cells can be identified by eGFP fluorescence or by using an anti-GFP antibody 2-8 weeks post-transplantation (data not shown). With either detection method, GFP staining found throughout the cell cytoplasm and thus the morphology of the grafted cells was revealed.

The morphology of GFP stained cells was simple spherical or fusiform with zero, one or two processes. The exogenous nature of the eGFP-expressing cells was confirmed by double staining for pig-specific NF70 (FIGS. 20A through 20D). Extracellular GFP staining was never observed. There was no evidence of phagocytosis or extracellular debris in the 2-8 week survival period. In control animals, no eGFP staining was observed around the injection site.

Peripheral Injection of Pig UCMS Cells

UCMS cells were injected into the periphery, intramuscularly (N=3) or both intramuscularly and intravenously (N=1), in a group of rats. Three weeks after IM injection, PKH 26-labeled UCMS cells were recovered from the injection site (FIGS. 21A and 21B). Three weeks after IM and IV injection, PKH 26-labeled UCMS cells were engrafted in the parenchyma of the kidney (FIGS. 21A and 21B). No immunocytochemical characterization was performed in these cases.

Brain Injection of Disrupted Pig UCMS Cells

About 99.8% of the PKH 26 dye loaded UCMS cells were disrupted by repeatedly sonic disruption prior to transplantation (FIG. 22A). No living cells were found in tissue culture. An aliquot of lysed cells equivalent to 10,000 lysed cells was injected into two rats. One rat survived one week, the other survived two weeks after injection before they were sacrificed and their tissue was processed. In both cases, cellular debris or red blood cells were found along the injection tract (FIG. 22B), but no fluorescent labeling was found within neurons or glia. On occasion, fluorescent blood cells were observed along the injection tract (e.g., arrows in FIG. 22B). The red blood cells were easily distinguished from the PKH 26-labeled UCMS cells by their smaller size and smooth, round or doughnut-like appearance.

Discussion

These experiments provided several lines of evidence indicating that pig UCMS cells are stem cells that do not stimulate immune rejection when transplanted into the adult rat. First, pig UCMS cells survived 2-6 weeks after transplantation into the rat without immune suppression therapy. Second, pig UCMS cells responded to differentiation cues and modified their morphology and neurochemical phenotype to resemble neural cells both in cell culture and after transplantation into the rat brain. At two and four weeks after injection, most pig UCMS cells found in the rat brain were simple spherical cells with a granular cytoplasm. At six weeks, some UCMS cells had migrated from the injection site to a site adjacent to the corpus callosum and had short processes. Third, pig UCMS cells that were injected into the periphery were recovered in the injection site and the kidney three weeks later. Fourth, after injection of disrupted UCMS cells, no cells labeled by PKH 26 were found. Together these results indicate that pig UCMS cells are relatively non-immunogenic, that they respond to local cues found in the adult rat, and that these cells engraft without stimulating significant immune rejection.

Transplantation and Recovery of UCMS Cells

After tissue processing, the transplanted cells were identified in three different ways. First, the UCMS cells that were loaded with PKH 26 prior to transplantation were recovered by observing fluorescent cells, and not fluorescent debris, along the injection track and elsewhere in the brain. Red blood cells (RBCs) also fluoresce and were found in the brains of transplanted and control animals but RBCs were easily differentiated from the transplanted UCMS cells based upon their size and shape (FIGS. 22A and B). Injection of disrupted PKH 26 labeled UCMS cells did not label host neurons or glia. This indicates that the lysed PKH 26 labeled UCMS cells did not stain host cells following phagocytosis.

Second, many, but not all, transplanted UCMS cells were identified by their staining for the pig-specific neurofilament 70 (NF70) immunocytochemical staining 2-6 weeks after introduction. The NF70 antibody does not recognize rodent epitopes, and in these experiments NF70 immunocytochemical staining was never found in normal or control animals. In contrast, NF70 staining was often co-localized with PKH 26 fluorescence. Importantly, NF70 staining was not found in debris, phagocytic cells or lysosomal vesicles.

Third, the UCMS cells that were engineered to produce eGFP prior to transplantation were recovered either by observing eGFP using epifluorescence, or by immunocytochemical staining for the GFP protein and immunoperoxidase. Immunocytochemical staining for GFP would not be expected in the case of UCMS cell lysis because the released GFP protein and mRNA is likely to be degraded by phagocytic cells. In both cases, eGFP was found in transplanted animals, but not in either control group. All three of these recovery methods indicated that the transplanted cells were found in the rat brain 2-6 weeks after injection. Further, these results indicated that the transplanted cells do not form tumors.

Based on certain results, it is believed that transplantation of 150 eGFP expressing UCMS cells and a time series analysis indicated that UCMS cells can replicate between transplantation and a 2-8 week recovery period.

These experiments did not directly evaluate the infiltration of lymphocytes, macrophages, natural killer cells, microglia or astrocytes. Nonetheless, these results suggest that the grafted cells were not recognized or attacked. There was no indication of cellular lysis or cellular debris in animals transplanted with UCMS cells and there was not obvious signs of immunological response, such infiltration of immune cells, perivascular cuffing, extracellular debris, graft antigens within cells with glial morphology or size, etc. In contrast, when lysed cells were injected into the brain, debris and RBCs were found in the injection site. Further, UCMS cells were recovered in the kidney 3 weeks after peripheral injection or up to 6 weeks after injection into the brain. This suggests that UCMS cells avoid immune surveillance.

Fate of Transplanted Tissue

Implanted UCMS cells primarily developed into neural grafts as indicated by immunocytochemical staining for pig-specific NF70 at 2-6 weeks after transplantation and by the immunocytochemical staining for other neuron specific markers weeks after transplantation. For example, positive double-labeling of UCMS cells for two other cytoskeletal markers also identified the transplanted cells as neurons: class III neuron-specific β-tubulin (TuJ1), and microtubule-associated protein 2 (MAP2). In contrast, fewer oligodendrocytes originated from the grafted material, as indicated by the few cells that double stained for 2',3'-cyclic nucleotide-3'-phosphodiesterase (CNPase) and PKH 26. It was noted that associated with the grafted tissue, pig-specific NF70-stained cells were found that did not contain PHK 26 (these cells are indicated by asterisks in FIGS. 19 and 20). This indicates that not all the UCMS cells were labeled in vitro prior to transplantation.

Example 9

UCMS Cells Transplanted into Model Parkinsonian Rat

Materials and Methods
Cell Culture and Counting

Pig UCMS cells were cultured and maintained by known methods. Manipulation of pUCMS cells to express eGFP was conducted by known methods. Briefly, pUCMS cells that had been cultured in vitro 60 passages were transfected with enhanced green fluorescent protein (eGFP). After several selection passages, the eGFP expressing pUCMS cells were lifted by a trypsin solution. The cells were counted by a hemocytometer and were adjusted to a final concentration of approximately 150 cells per microliter. The number of cells in one microliter was verified by spreading a 1 microliter drop on a plastic petri dish and manually counting the cells at 10× in bright field of a light microscope. The cell concentration was confirmed before and after the injection to insure that approximately 150 cells were delivered.

Transplantation Procedure

A guide cannula was implanted in the brain of each anesthetized male Harlan Lewis rat via stereotaxic surgery. A guide cannula was implanted in the right striatum (Bregma +0.5, Lateral 3.4, Ventral 5.0 mm from the surface of the brain) and attached to the skull with screws and dental acrylic. At least three days later, the dust cap was replaced with an injection cannula and the striatum was lesioned by a single injection of 3 ul of 7 mg/ml 6-hydroxydopamine (6-OHDA, Sigma Chemical Co). At least one week after 6-OHDA lesion, approximately 150 eGFP-pUCMS cells in 1 ul of the sterile medium were injected in the same site. Each injection was performed over 5 min. At 2, 4, 6, and 8 weeks post-transplantation, two rats were randomly selected, anesthetized and sacrificed by transcardial perfusion with heparinized isotonic saline rinse followed by 10% buffered neutral formalin. The brains were removed, postfixed, and cryoprotected in 20% sucrose overnight.

Tissue Processing and Immunocytochemical Processing:

Frozen sections of the brains were cut at 40 μm coronally and the sections were collected into three sets of adjacent sections, each set consisting of every third serial section. Immunocytochemical detection of a single antigen was performed on one set of sections by known methods and the adjacent sets were held in reserve in a known cryoprotectant solution. Briefly, free-floating tissue sections were stained with primary antibodies for GFP (rabbit host, 1:1000, Santa Cruz Biotechnology, Inc) or TH (rabbit host, 1:2000, East Acres Biologicals). The antigens were localized either with diaminobenzidine and hydrogen peroxide using a commercially available ABC kit (Vectastain) or with immunofluorescence. For immunofluorescence localization, 7-amino-4-methylcoumarine-3-acetic acid (AMCA)-Avidin D (Vector Laboratories) was used to localize the biotinylated secondary antibody.

The immunocytochemically-stained sections were mounted on subbed microscope slides, air-dried, and rinsed with distilled water. For viewing the immunofluorescence and eGFP staining, the sections were observed on a Leica DMRD microscope after clearing and coverslipping with glycerol containing N-propyl gallate to prevent fading. Immunocytochemically-stained cells were considered positive if the signal in the cytoplasm above background and if the signal was absent in tissues in which the primary antibody had been omitted. To be considered double-labeled, the morphology and location of the cells must appear identical in both bright field (DAB) and fluorescence (eGFP) for immunoperoxidase detected cells, or in both filter combinations for immunofluorescence (UV filter set for AMCA versus FITC filter set for eGFP).

Evaluation of the Size and Number of the Cells

To measure cell size and number, the brain sections were stained with anti-GFP antibody and visualized with DAB. The stained sections were evaluated microscopically using bright field illumination. Individual cells were measured using a Bioquant image analysis system (R&M Biometrics). The cells that appeared in both bright field (DAB) and epifluorescence (FITC filter set for eGFP) were considered positive. In a blind fashion, the area of at least 75 complete cells was measured and the cell-size distribution was analyzed for normality (StatView 5.0) and plotted on a frequency histogram. In all cases, the distribution was normal and an average cell size was calculated. To estimate the number of transplanted cells, the image analysis software was used to measure the area of dark pixels in sections containing graft cells. This represented the total area of the graft. The total dark pixel area was divide by the average cell area to yield an estimate of the number of graft cells per set of sections. Because there are 3 sets of frozen brain sections per each animal, the estimate of the total number of graft cells in the respective animal was three times the total number of graft cells in one set of sections.

Assessment of TH-Positive Cells

The second set of brain sections was immunocytochemically-stained for tyrosine hydroxylase (TH) and visualized by AMCA. To avoid experimental bias, the identity of the slides was covered by an opaque tape and all the slides were coded by a different person prior to analysis. The TH-positive graft cells appeared in both the FITC filter set (eGFP) and the UV filters set (AMCA). To obtain an estimate of the percentage of graft cells that stained for TH, a minimum of ten fields per animal were selected for counting based upon the distribution of cells in the field (fields were selected that did not have clumps of graft cells). In each field, the number of eGFP cells (FITC) and the eGFP-TH positive cells (AMCA and FITC) were counted. The percentage of TH-positive graft cells in the ten fields was calculated and averaged to yield an estimate of the percentage of TH-positive graft cells in each animal at each survival period. After the analysis was completed, the slides were decoded.

Statistical Analysis

All tissue manipulations were conducted without knowledge of the survival period after grafting. The graft neurons were identified using bright field microscopy (following immunocytochemical staining and DAB localization) or by the eGFP fluorescence in epifluorescence. The number of graft cells was determine in sections where individual graft cell boundaries could be seen. After cell size measurement and pixel area determination, the survival status was decoded for statistical analysis. The histogram of the cell size was inspected for outliers. When no outliers were observed, the Komogorov-Smirnov test was used to compare the distribution of measured cells size to an idealized normal distribution (Statview 5.0). When outliers were observed, the Mann-Whitney U test was used to compare the distributions.

All distributions were found to be normal. Thus, ANOVA was used to test interactions between the independent variable (survival period after grafting) and the dependent variables (cell size, graft cell area, percentage of TH graft cells and number of TH graft cells). Significance for ANOVA was set at $p<0.05$ (two tailed). Following significant ANOVA, post hoc analysis using Scheffe's F test was used to examine planned comparisons. Significance for post hoc testing was set at $p<0.05$ (two tailed). Mean plus or minus one standard error are presented on graphs.

Results

Cannula Placement

In one out of eight animals, the guide cannula was misplaced. This animal was excluded from further analysis (six week survival). Because the six week survival period had only one animal with a good injection, we did not include those data in the results. Thus, the results presented here from the 2, 4 and 8 week survival periods are averaged from two animals at each survival period.

Behavioral Findings

None of the animals showed any behavioral abnormalities following the implantation of cannula. In the initial recovery period following 6-OHDA lesion, the animals demonstrated rotation toward the damaged hemisphere. No attempt was made to quantify rotational behavior. The animals did not show any behavioral signs or changes in their health. After the transplantation with eGFP-pUCMS cells, the animals acted normally and appeared in robust health throughout the 2-8 week survival period (there was no indication of sickness behavior, weight-loss, etc).

Histological Findings

In the two week survival period, the morphology and distribution of the pUCMS cells were distinguishable from rat cells: the graft cells were small, spherical and had a granular cytoplasm. In bright field, the unstained graft cells had a faint brown appearance. There was no gross or histological evidence of immune rejection in the brain of any of the animals, e.g., there was not vacuolization, perivascular cuffing, or cellular infiltrate. Furthermore, there was no evidence of tumor, teratoma or scar formation in the transplant recipients. Host tissue withdrew surrounding the guide cannula implantation site.

After histological processing, the pUCMS cells expressing eGFP could be identified by their endogenous candy apple green fluorescence under blue excitation (FITC filter cube, see FIG. 23A). To control for the possibility of autofluorescence by host cells, the sections were immunocytochemically-stained using an antibody to GFP and visualized with AMCA using the UV excitation. These results are shown in FIG. 23B. The graft cells exhibited green fluorescence using blue excitation due to the GFP; these same cells showed blue fluorescence due to staining by the anti-GFP antibody and localization with AMCA using UV excitation. When the primary antibody was omitted, the graft cells were not seen with UV excitation (FIGS. 23C and 23D).

Figure 25:
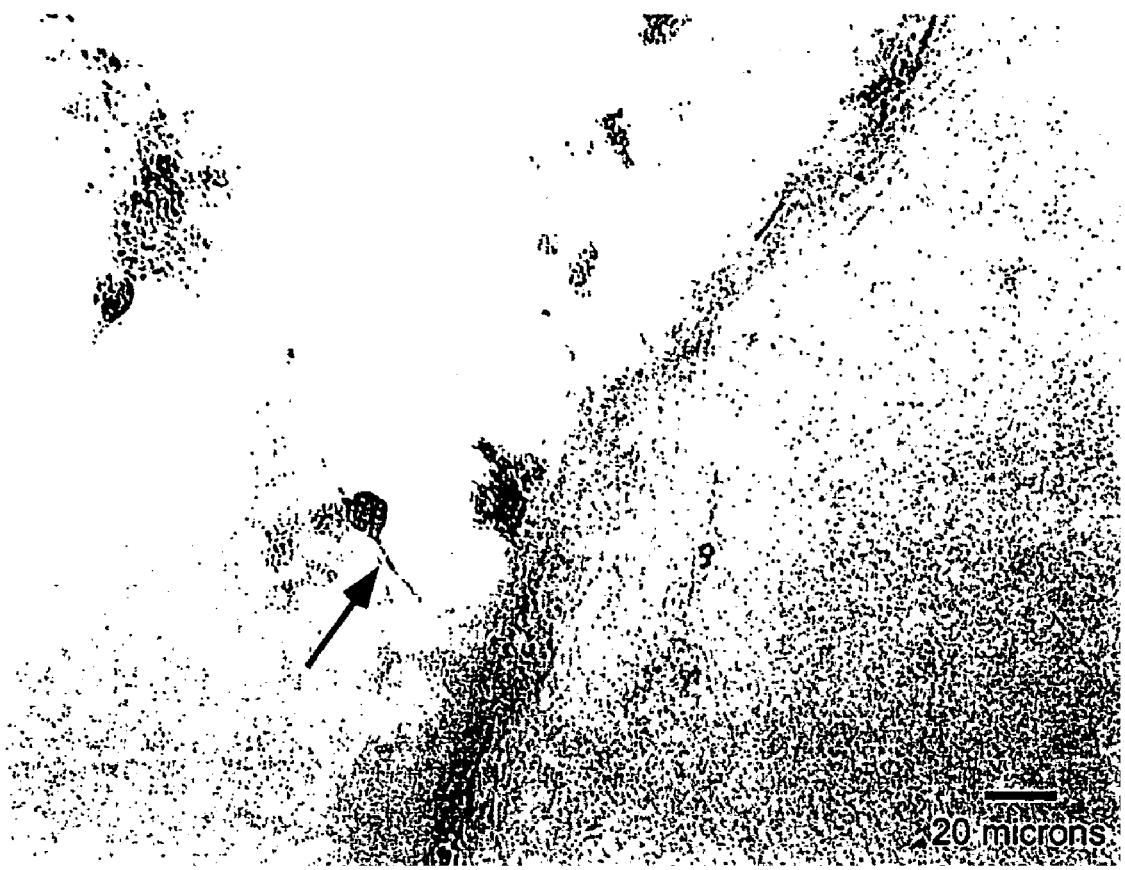
FIG. 25 illustrates results showing that pig UCMS-eGFP cells extended processes, like neurons, after they were transplanted into rats with a previous unilateral 6-OHDA striatal lesion. Occasionally, eGFP-pUCMS graft cells were seen extending processes (black arrow) into the rat brain tissue. This indicates that pig UCMS cells responded to local cues and differentiated into a neural phenotype.
Figure 26:
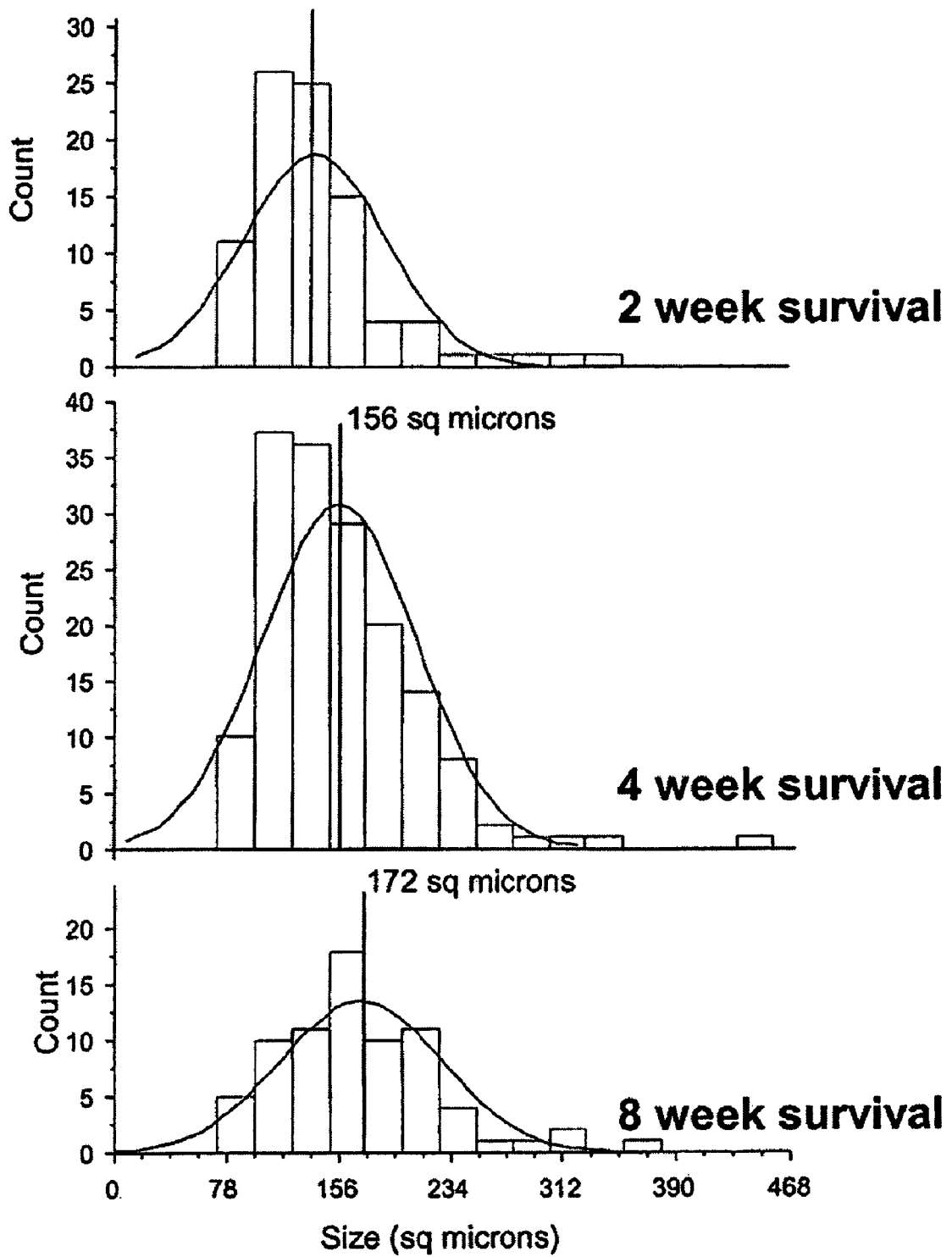
FIG. 26 illustrates results of assessment of transplanted pig UCMS graft cell size over time after transplantation. The size distribution of 75-100 individual graft cells was determined for each animal and analyzed. The distributions were found to be unimodal and normal.

At 2, 4 and 8 weeks post-transplantation, the eGFP-pUCMS cells were localized by immunocytochemical staining for GFP. Two weeks after transplantation, the graft cells were found in a restricted area along the sides and at the tip of the guide cannula tract. At this time, most of the cells were clustered. Occasionally, individual cells were observed; these cells appeared small and round with a granular cytoplasm (FIG. 24A). Four weeks after transplantation, the graft cells were found further from the guide cannula tract in the surrounding host brain tissue. At this time, more of the cells were dispersed and a greater percentage of the graft cells were elongated or bipolar in appearance. A low percentage of the graft cells possessed short, primary processes attached to the cell body (FIGS. 24B and 25). Eight weeks after transplantation, the GFP staining was more diffuse and less intense in the regions surrounding the guide cannula. At this survival time, the graft cells were significantly larger in size when compared to the graft cells recovered 2 weeks post-transplantation (FIGS. 24C and 26).

Cell Size

The sections were immunocytochemically-stained for GFP and visualized with DAB.

To be considered for analysis, the graft cells were localized by DAB and epifluorescence. For each animal, the cell size histogram was inspected for outliers and the normality test revealed the data to be unimodal and normally distributed (FIG. 26). At each survival period, the cell size distributions from the two animals was compared and the distributions were not significantly different.

Thus, the cell size data from each survival period was pooled and shown in FIGS. 27A and 27B. At 2 weeks post transplantation, the average size of the graft cells was 140.0±3.7 sq. microns. At 4 weeks post transplantation, the average size of the graft cells was 160.2±12.1 sq. microns. At 8 weeks post transplantation, the average size of the graft cells was 171.9±2.3 sq. microns. The average size of each survival period is shown in FIGS. 27A and 27B. The size of graft cells is significantly larger in the 8 week survival animals.

Graft Cell Number

At 2 weeks after transplantation, the estimated number of graft cells in set A was 1825±163 (yields a total of 5475 graft cells per animal). At 4 weeks after transplantation, the estimated number of graft cells in set A was 5758±400 (yields a total of 17274 graft cells per animal). At 8 weeks after transplantation, the number of graft cells in set A was estimated to be 6904±1000 (yields an estimated total of 20712 graft cells per animal). As shown in FIGS. 27A and 27B, the number of graft cells increases significantly from 2 to 4 weeks and 2 to 8 weeks.

TH-Positive Graft Cells

The sections in set B were immunocytochemically-stained using anti-TH antibody and visualized using AMCA. The graft cells that co-localized green fluorescence (GFP) and blue fluorescence (AMCA) are considered to be TH-positive graft cells (FIGS. 28A and 28B). The sections stained without the TH primary antibody were used as a control. In this case, none of the graft cells showed a positive staining for TH (FIGS. 28C and D).

The percentage of TH-positive graft cells increased over the 2-8 week survival period (FIGS. 29A and 29B). At two weeks post-transplantation, 1.0±0.6% of the graft cells were positive for TH. At four weeks post-transplantation, 3.4±0.6% of the total graft cells were positive for TH. At eight weeks post-transplantation 6.0±0.3% of the total graft cells were positive for TH. To estimate the total number of TH-positive graft cells at each survival period, the total number of graft cells previously calculated was multiplied by the percentage of TH-positive graft cells. The estimated number of TH-positive graft cells is shown in FIGS. 29A and 29B. A total of 54 TH-graft cells were estimated to be found in the two week survival animals, 587 TH-positive graft cells per animal in the four week survival animals, and approximately 1242 TH-positive graft cells per animal in the 8 week survival animals.

Behavioral Changes

Figure 30:
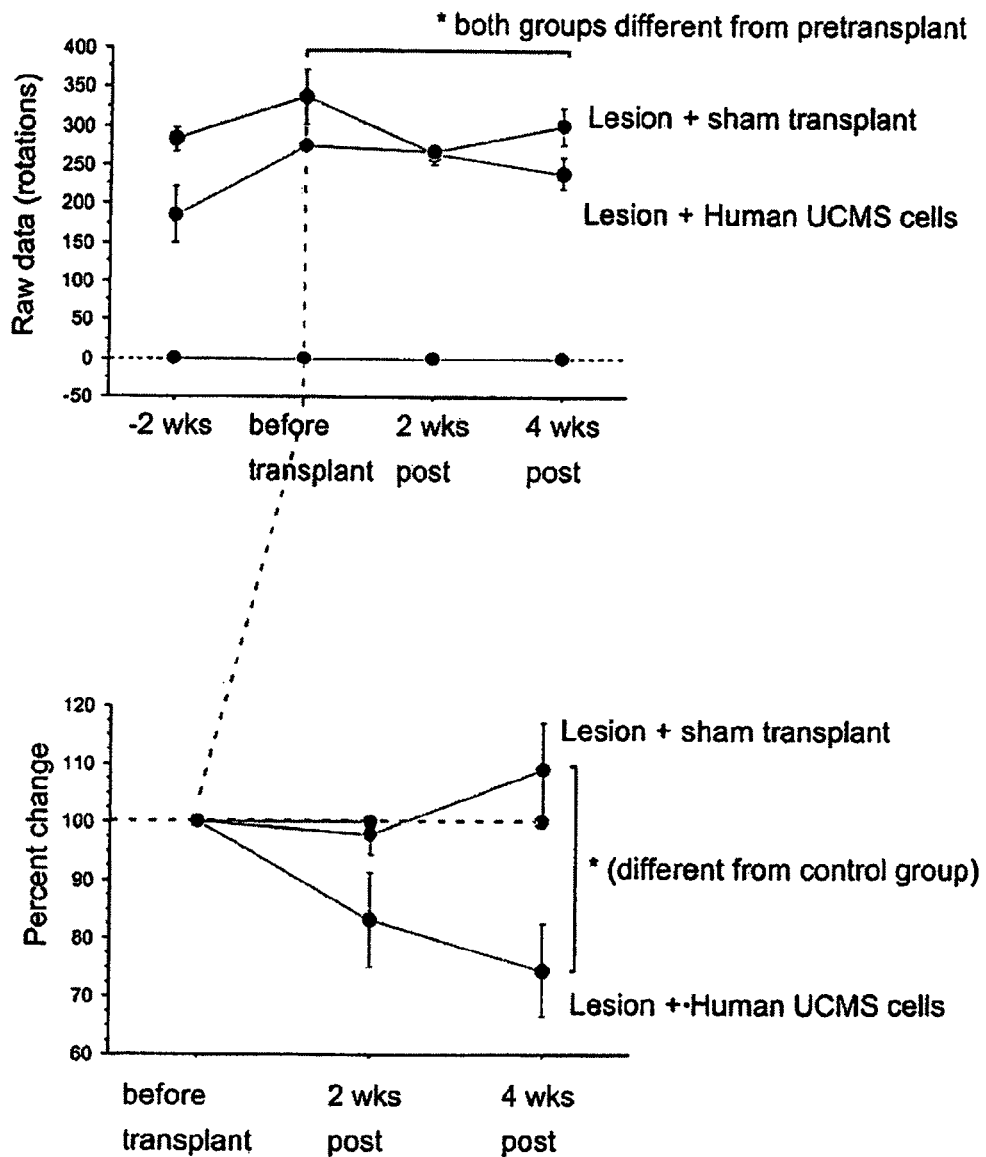
FIG. 30 illustrates results of behavioral studies of Parkinsonian rats that received either a sham transplant or an actual transplant of human UCMS cells. The rats receiving the transplanted UCMS cells showed a significant decrease in behavior indicative of Parkinson's disease.

Rats were evaluated for behavior indicative of Parkinson's disease before and after actual and sham transplantation. Rotational behavior was induced and evaluated by known methods. Decreased rotation indicates a beneficial effect on reducing signs of Parkinson's disease. The beneficial results of grafted UCMS cells are illustrated in FIG. 30. Lesioned rats that were sham transplanted exhibited an increase in rotational behavior after the sham operation. In marked contrast, rats receiving a transplant of human UCMS cells rotated far less, about a 25% decrease in rotations. This indicates a substantial effect of the transplanted UCMS cells in this model of Parkinson's disease.

Discussion

These results indicate that pig UCMS cells replicated after transplantation into the 6-OHDA lesioned rat brain. The transplantation of 150 cells resulted in 20,000 cells at 8 weeks. The pig UCMS cells appeared to be not dividing or dividing more slowly 8 weeks after transplantation. The data suggest that after rapid division in the initial 2-4 weeks, many cells dropped out of the cell cycle and differentiated into neural cells. The fact that pUCMS cells differentiated into TH staining cells indicates that pUCMS cells responded to the special environment found in the lesioned rat brain and replaced TH positive cells that were destroyed by the lesion.

Transplantation of 150 pUCMS cells produced an estimated 1200 TH-stained pUCMS cells at 8 weeks. Previous work has indicated that the therapeutic threshold in the rat to treat or reverse the Parkinsonian phenotype was 1000 TH cells. Transplantation of 10000 pUCMS cells into rat brain was well-tolerated and did not stimulate an apparent immune rejection response. Therefore, we conclude that the "dose" of pUCMS cells needed to reverse Parkinsonian symptoms can be delivered without an apparent rejection response.

The transplanted UCMS cells had substantial benefit on the behavior of the rat. The rats exhibited about a 25% decrease in drug induced rotation after receiving a transplant of human UCMS cells.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The specification, experimental section and description of the UCMS cell isolation, growth, transformation and use provide a basis for understanding the invention. The invention however should not be limited to the disclosure set forth above since a variety of embodiments can be obtained without departing from the spirit and scope of the invention. The invention resides in the claims hereinafter appended.

We claim:

1. A method of reducing motor dysfunction associated with Parkinson's disease in a patient with Parkinson's disease comprising:
    a) enzymatically dispersing umbilical cord matrix to provide enzymatically dispersed umbilical cord matrix cells;
    b) culturing the enzymatically dispersed umbilical cord matrix cells in the presence of epidermal growth factor (EGF) and platelet derived growth factor (PDGF) to proliferate the umbilical cord matrix cells;
    c) culturing the enzymatically dispersed umbilical cord matrix cells on a substrate surface and removing non-adherent cells;
    d) culturing adherent cells from (c) to select for a population of umbilical cord matrix cells that comprise cells that are negative for CD34 and CD45, positive for telomerase activity, can be expanded in vitro, and maintained in culture through repeated passages;
    e) isolating the adherent cells from d);
    f) introducing the isolated adherent cells from e) into the substantia nigra region of the midbrain striatum in a patient with Parkinson's disease, and
    g) allowing the cells to integrate into the substantia nigra region of the midbrain striatum of the patient whereby motor dysfunction associated with Parkinson's disease in the patient is reduced.

2. The method of claim 1, wherein the umbilical cord matrix cells comprise a foreign gene.

* * * * *